(12) United States Patent
Milliman

(10) Patent No.: US 7,431,191 B2
(45) Date of Patent: Oct. 7, 2008

(54) SURGICAL STAPLING DEVICE WITH TILTABLE ANVIL HEAD

(75) Inventor: Keith L. Milliman, Bethel, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 11/788,671

(22) Filed: Apr. 20, 2007

(65) Prior Publication Data

US 2007/0257082 A1 Nov. 8, 2007

Related U.S. Application Data

(63) Continuation of application No. 10/968,722, filed on Jan. 27, 2005, now Pat. No. 7,364,060.

(60) Provisional application No. 60/512,482, filed on Oct. 17, 2003, provisional application No. 60/512,405, filed on Oct. 17, 2003, provisional application No. 60/617,007, filed on Oct. 8, 2004, provisional application No. 60/616,982, filed on Oct. 8, 2004.

(51) Int. Cl.
*A61B 17/068* (2006.01)

(52) U.S. Cl. .................. 227/179.1; 227/181.1; 227/19; 227/178.1

(58) Field of Classification Search .................. 227/19, 227/175.1, 177.1, 179.1; 606/8, 144
See application file for complete search history.

(56) References Cited

U.S. PATENT DOCUMENTS

| 3,388,847 A | 6/1968 | Kasulin et al. |
| 3,552,626 A | 1/1971 | Astafiev |
| 3,638,652 A | 2/1972 | Kelley |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,467,863 A | 8/1984 | Montana |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |

(Continued)

FOREIGN PATENT DOCUMENTS

CA 908529 8/1972

(Continued)

*Primary Examiner*—Brian D. Nash

(57) ABSTRACT

A surgical stapling device including a self-righting anvil assembly is disclosed. The anvil assembly includes an anvil center rod and a pivotable anvil head. The surgical stapling device includes an anvil retainer assembly having a locking member in the form of a trocar for moving the anvil head from its tilted position to its operative position upon attachment of the anvil assembly to the stapling device. A cam member is provided to retain the locking member in a first or locked position and, thus, the anvil head in the operative position until after the stapling device has been fired.

19 Claims, 67 Drawing Sheets

U.S. PATENT DOCUMENTS

| | | |
|---|---|---|
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,662 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,285,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,455,644 A | 10/1995 | Pietrafitta et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,775 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B2 | 7/2003 | Geitz |
| 6,595,887 B2 | 7/2003 | Thoma |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |

| | | | | | |
|---|---|---|---|---|---|
| 6,632,237 B2 | 10/2003 | Ben-David et al. | DE | 3301713 | 11/1989 |
| 6,659,327 B2 | 12/2003 | Heck et al. | EP | 0152382 | 8/1985 |
| 6,676,671 B2 | 1/2004 | Robertson et al. | EP | 0173451 | 3/1986 |
| 6,681,979 B2 | 1/2004 | Whitman | EP | 0190022 | 8/1986 |
| 6,685,079 B2 | 2/2004 | Sharma et al. | EP | 282157 | 9/1988 |
| 6,695,198 B2 | 2/2004 | Adams et al. | EP | 0503689 | 9/1992 |
| 6,695,199 B2 | 2/2004 | Whitman | FR | 1461464 | 12/1966 |
| 6,716,222 B2 | 4/2004 | McAlister et al. | FR | 1588250 | 4/1970 |
| 6,716,233 B1 | 4/2004 | Whitman | FR | 1136020 | 12/1979 |
| 6,742,692 B2 | 6/2004 | Hartwick | FR | 2443239 | 12/1979 |
| 6,763,993 B2 | 7/2004 | Bolduc et al. | GB | 1185292 | 3/1970 |
| 6,769,590 B2 | 8/2004 | Vresh et al. | GB | 2016991 | 9/1979 |

FOREIGN PATENT DOCUMENTS

| | | | | | |
|---|---|---|---|---|---|
| | | | GB | 2070499 | 9/1981 |
| | | | NL | 7711347 | 10/1977 |
| CA | 1136020 | 1/1982 | WO | 8706448 | 11/1987 |
| DE | 1057729 | 5/1959 | WO | 8900406 | 1/1989 |
| DE | 18355500 | 4/1961 | WO | 9006085 | 6/1990 |

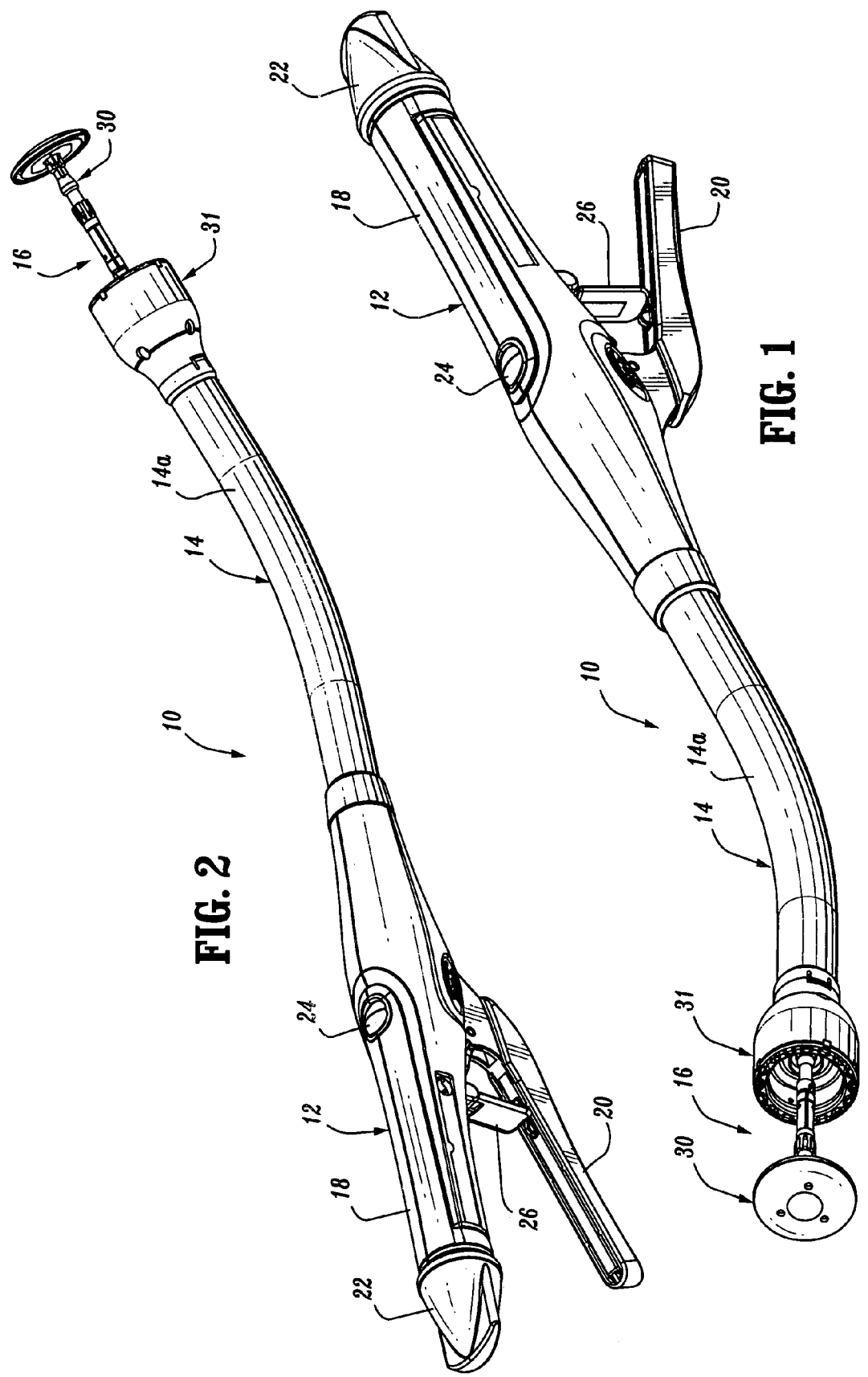

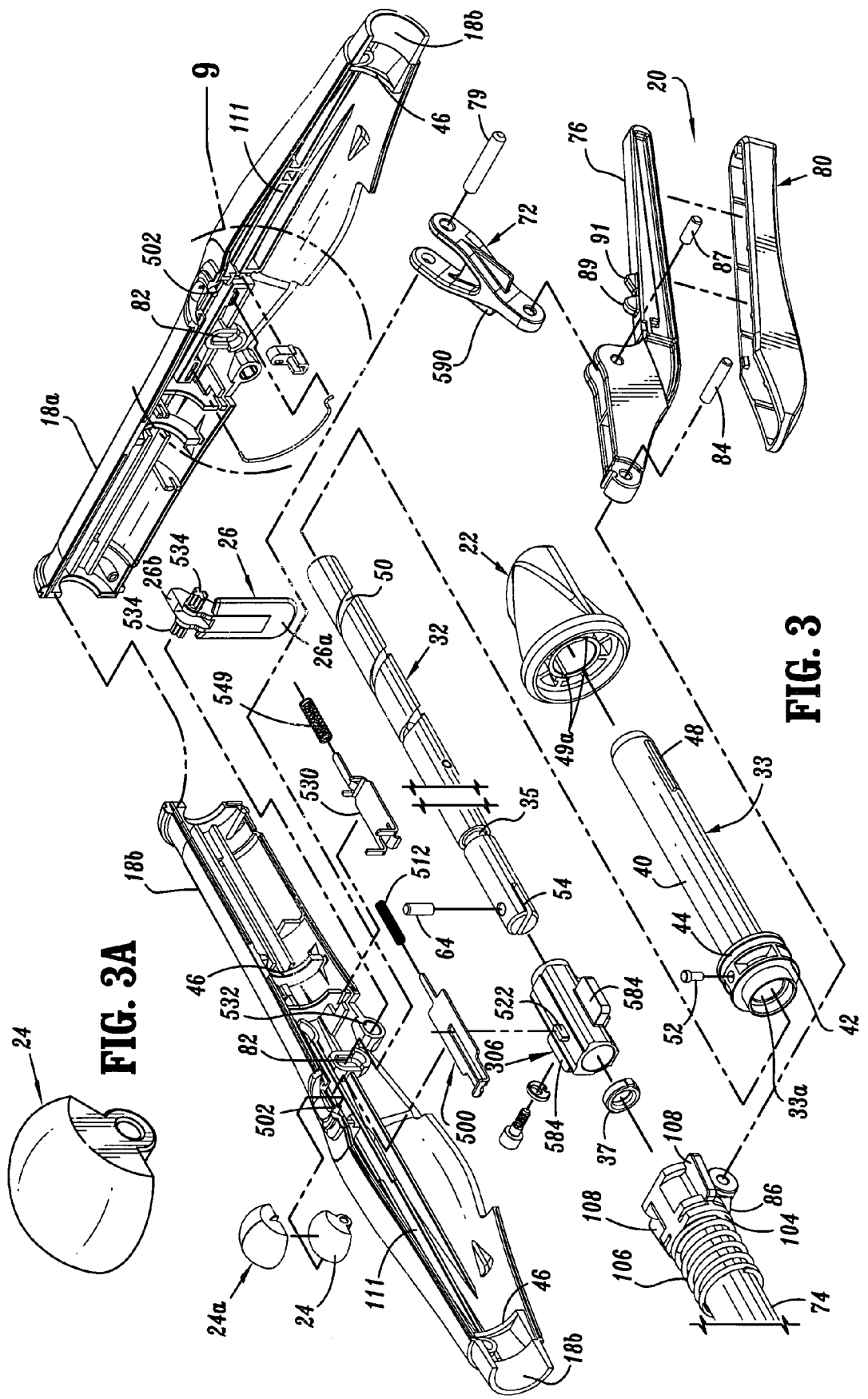

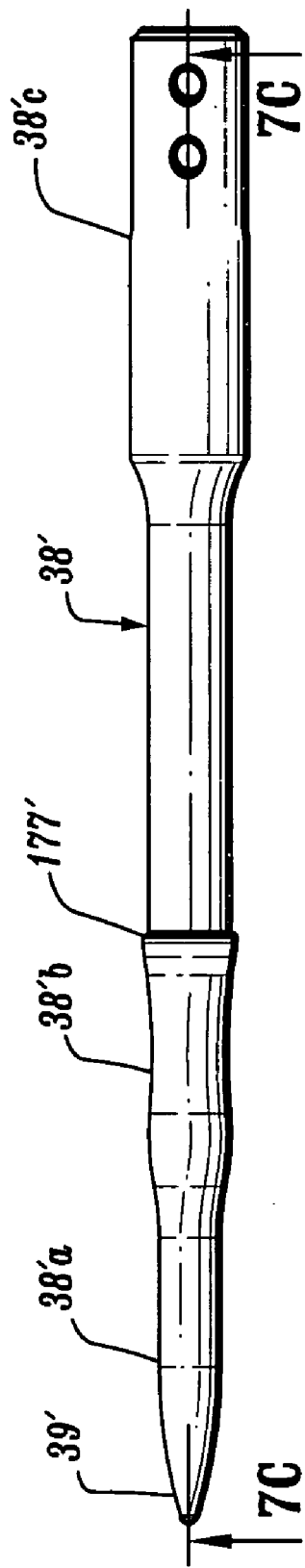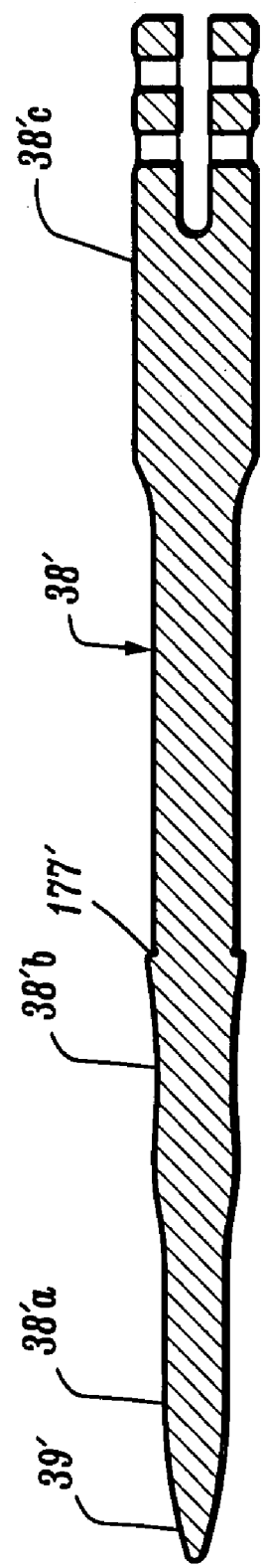
FIG. 7B
FIG. 7C

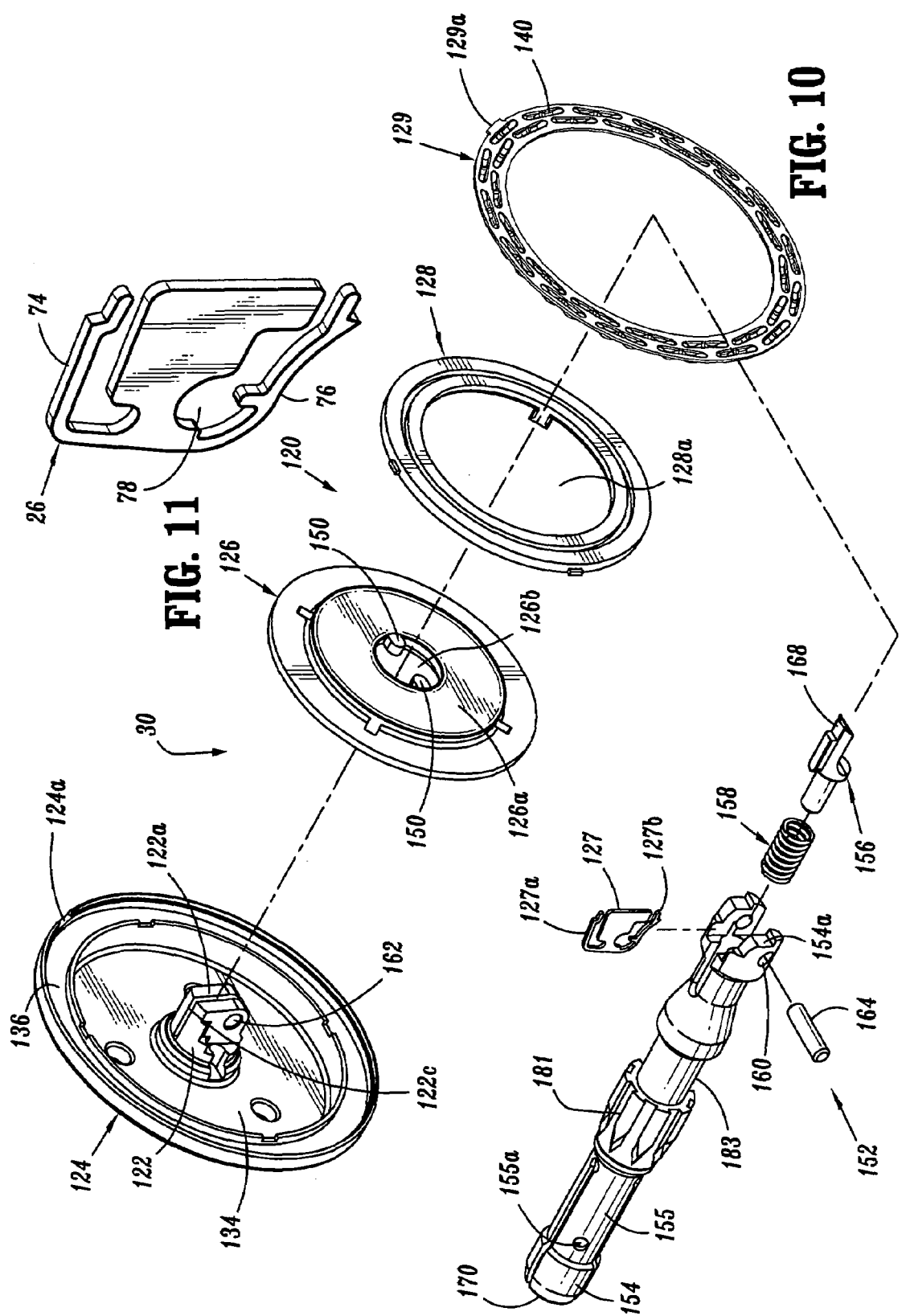

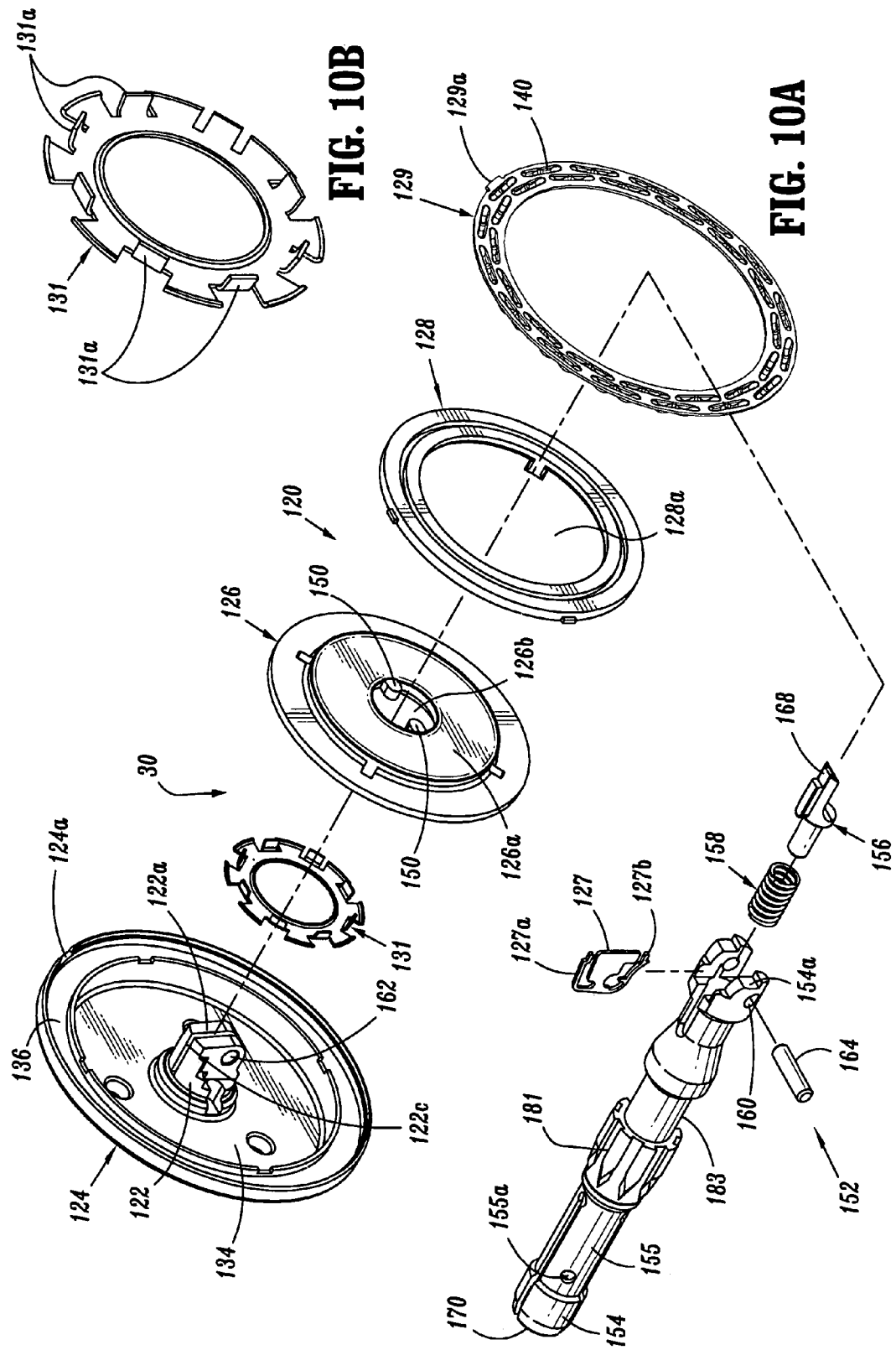

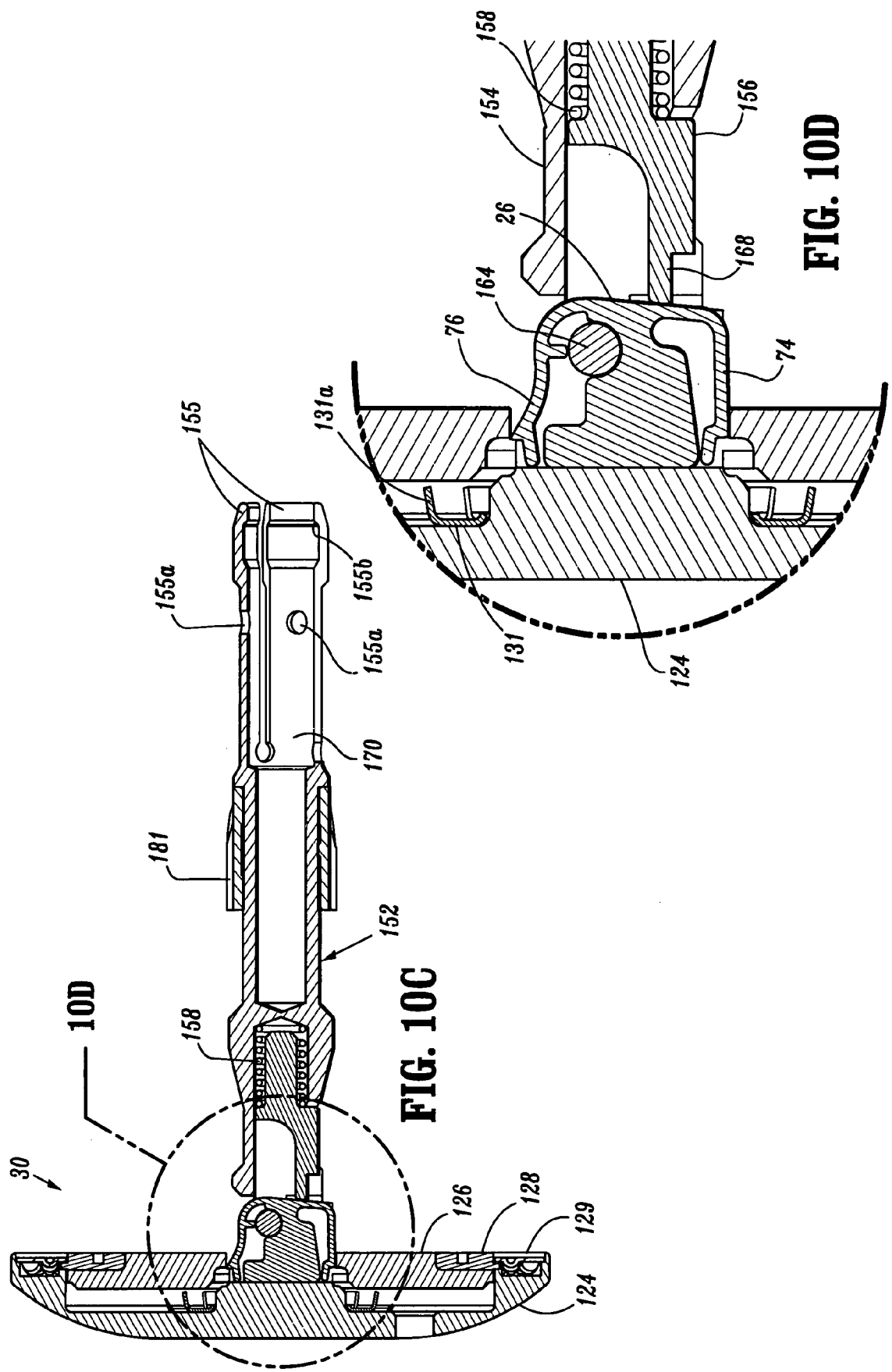

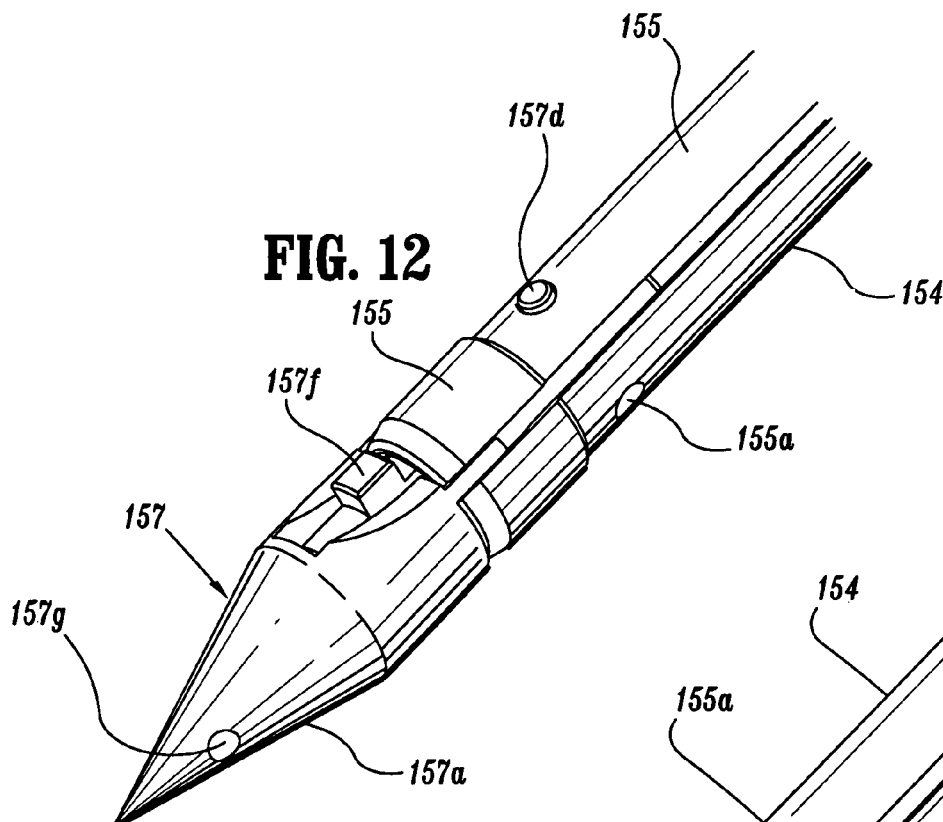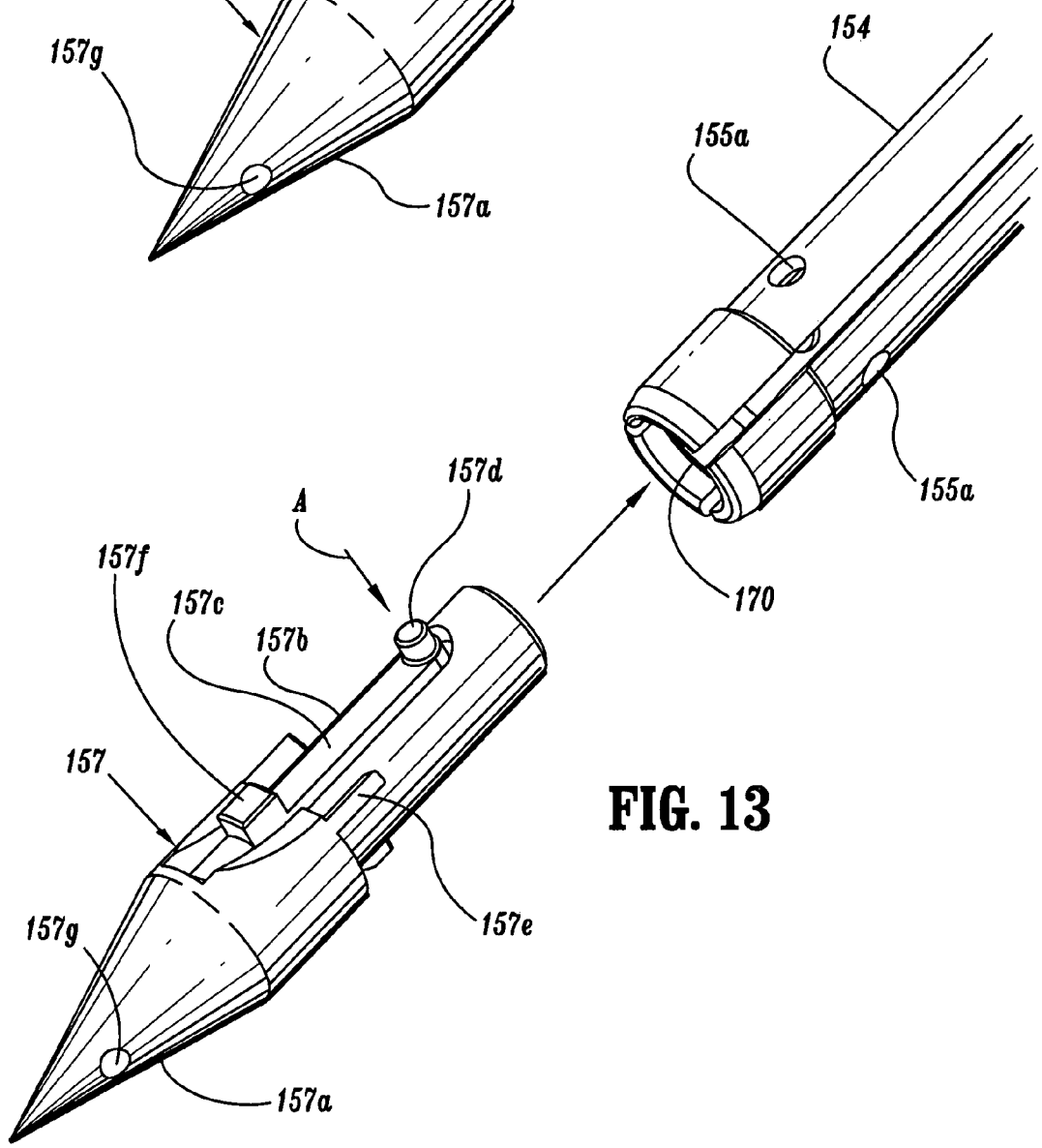

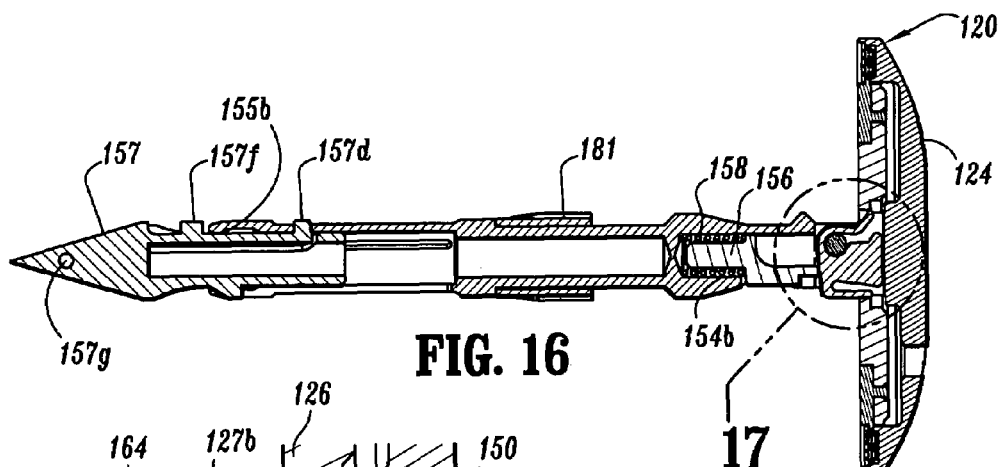
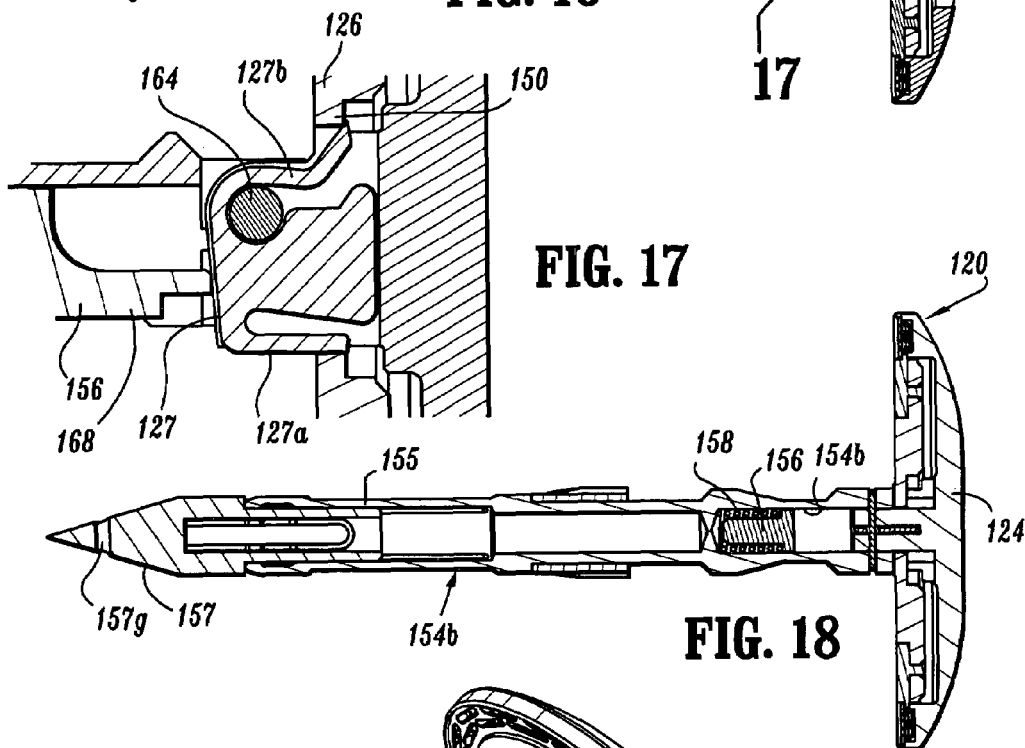
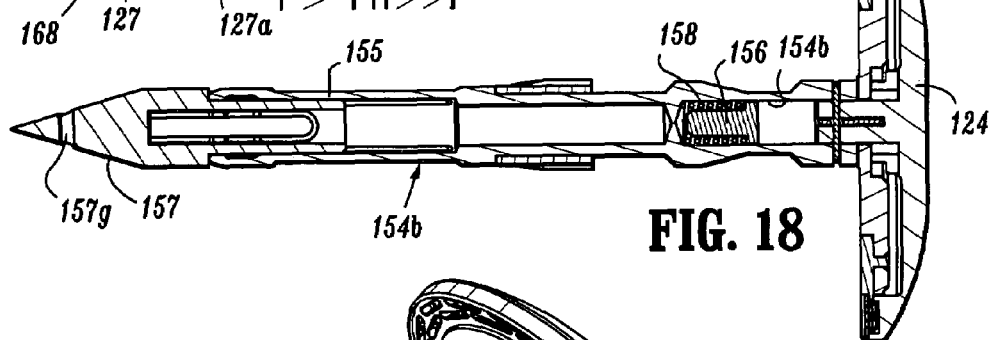
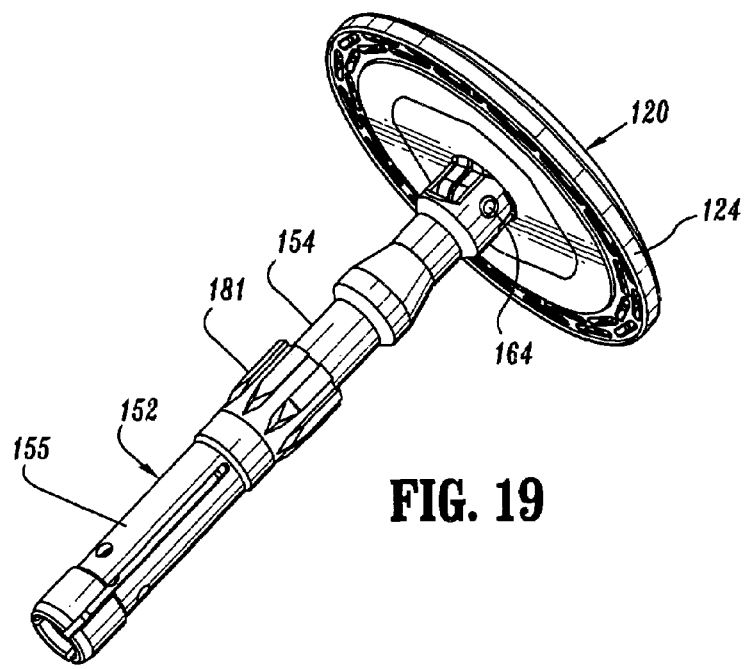

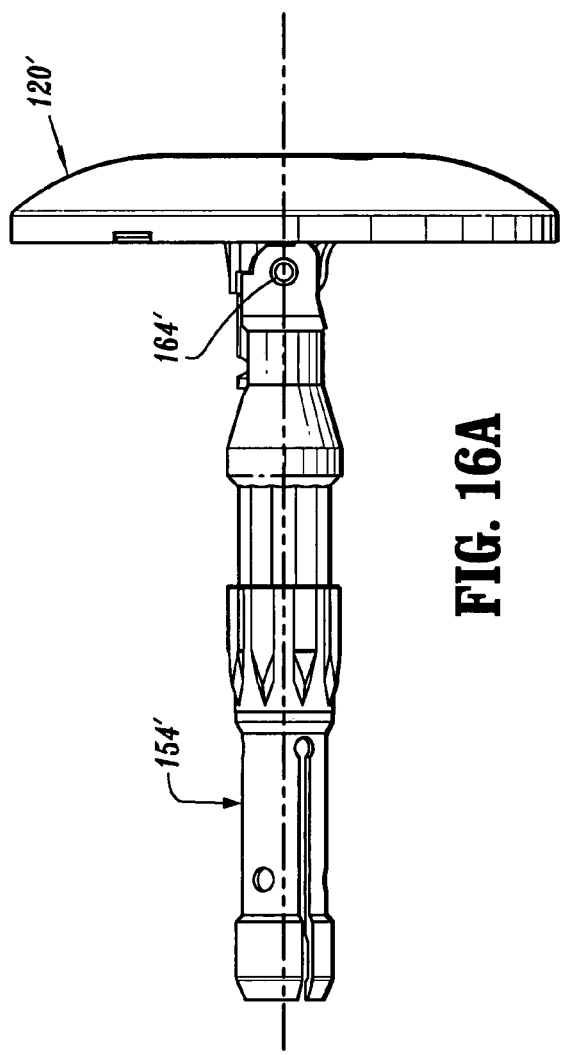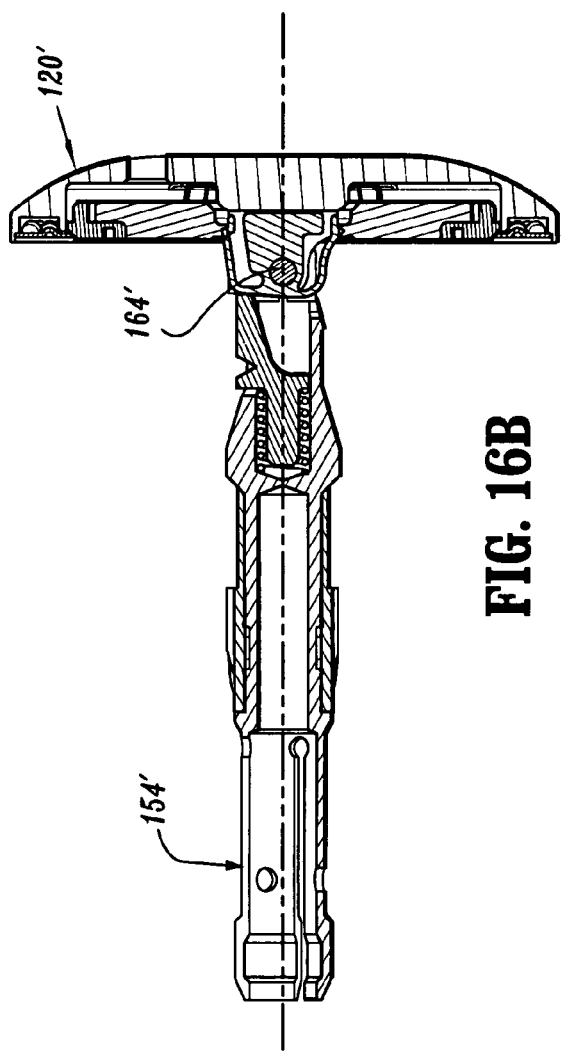

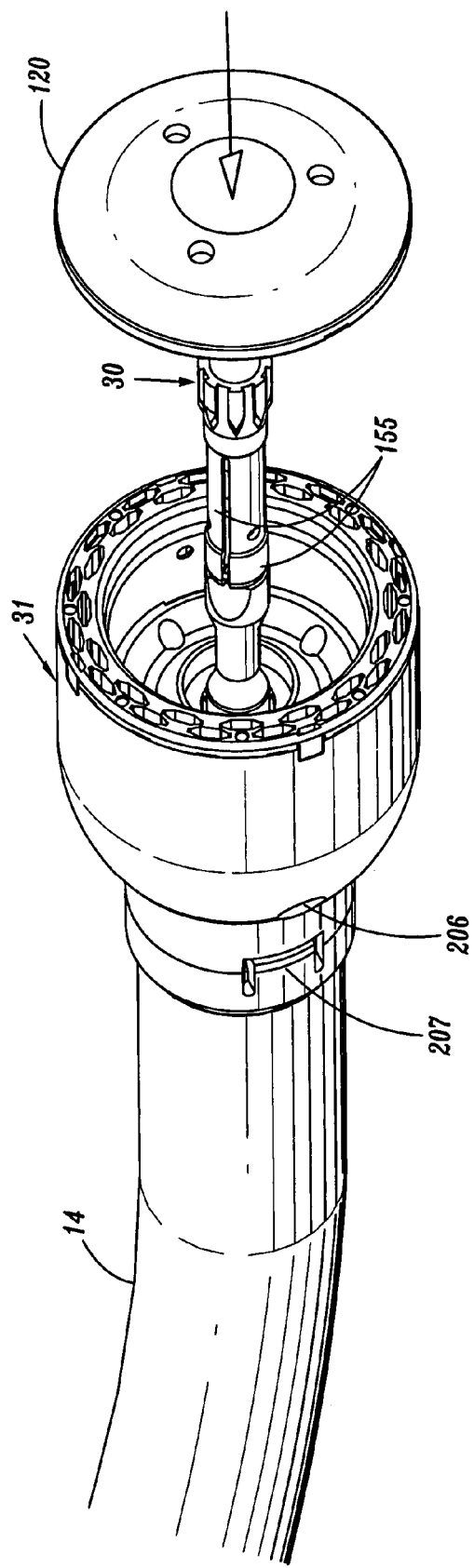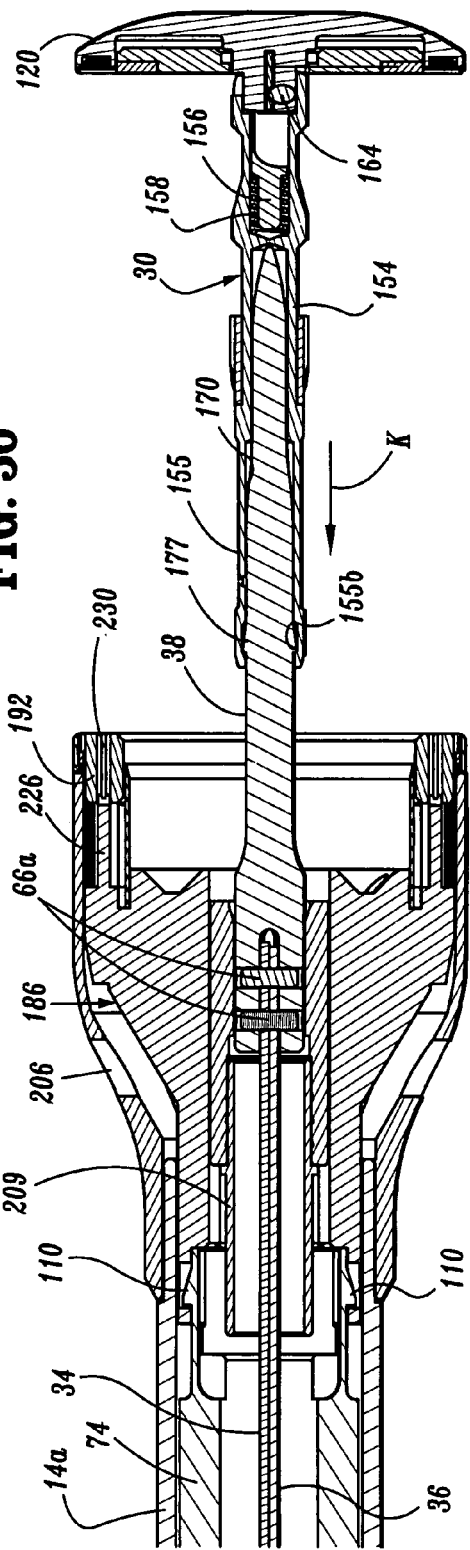
FIG. 36
FIG. 37

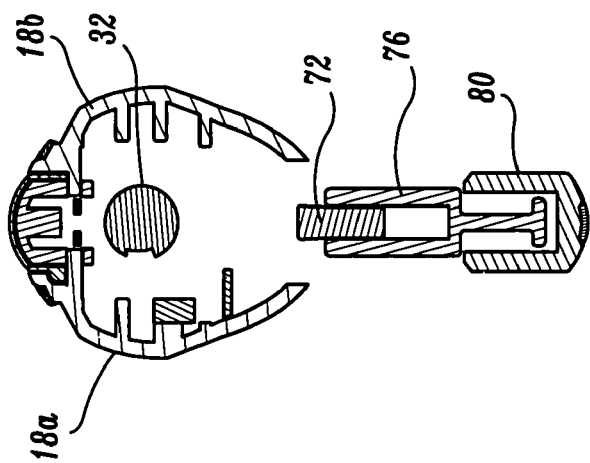
FIG. 41
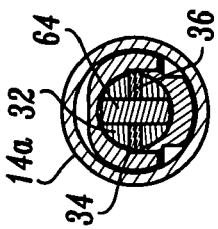
FIG. 44
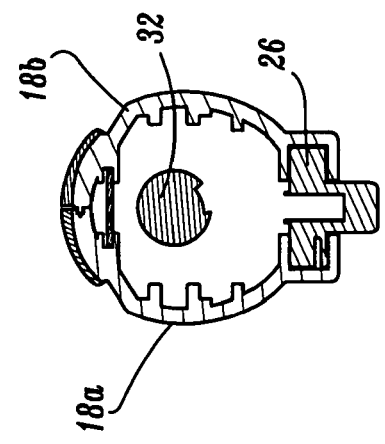
FIG. 40
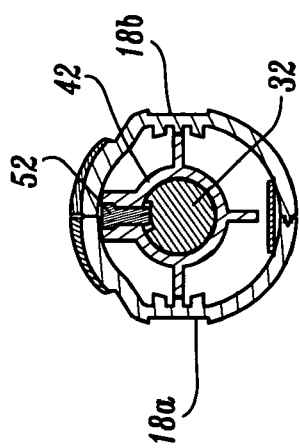
FIG. 43
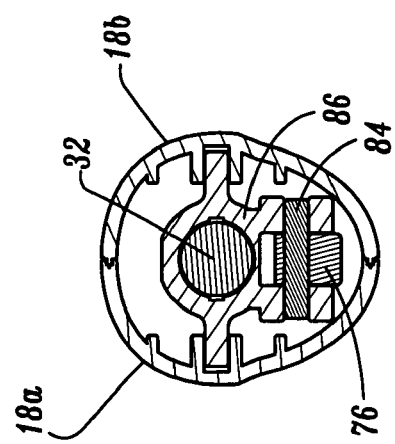
FIG. 39
FIG. 42

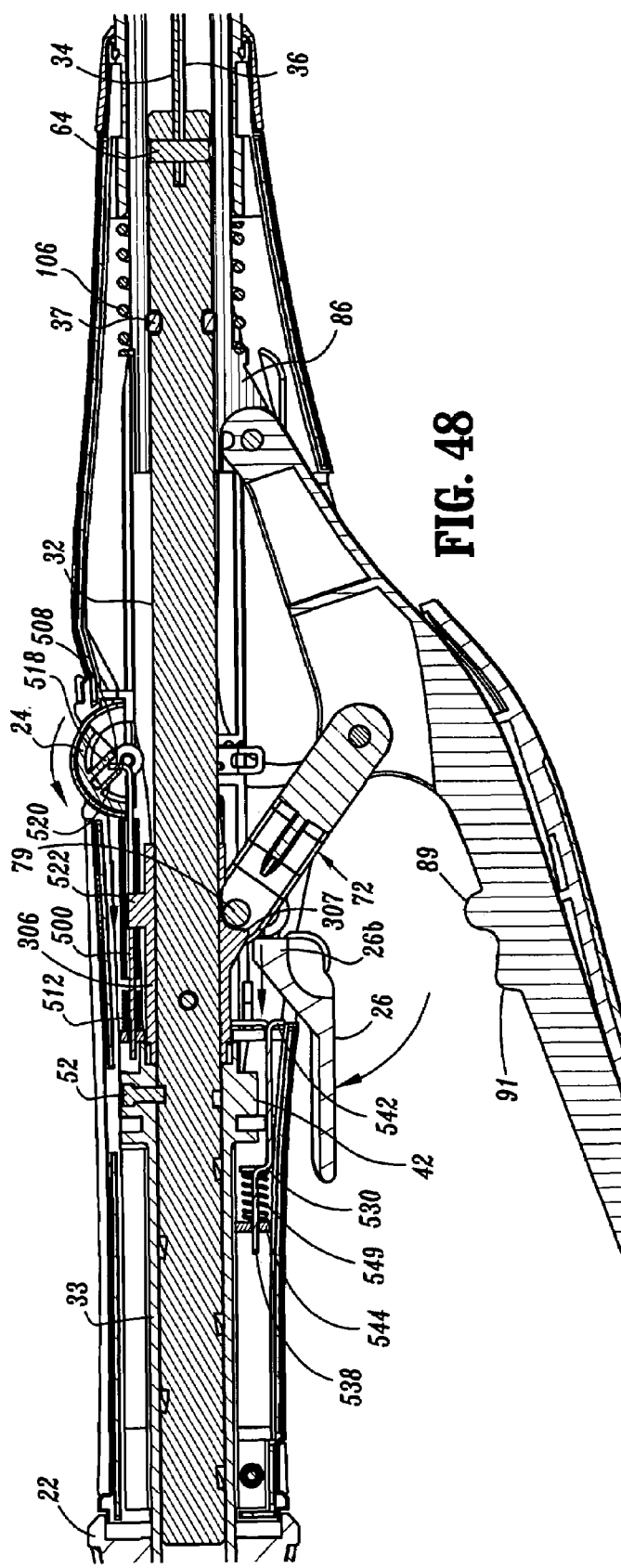
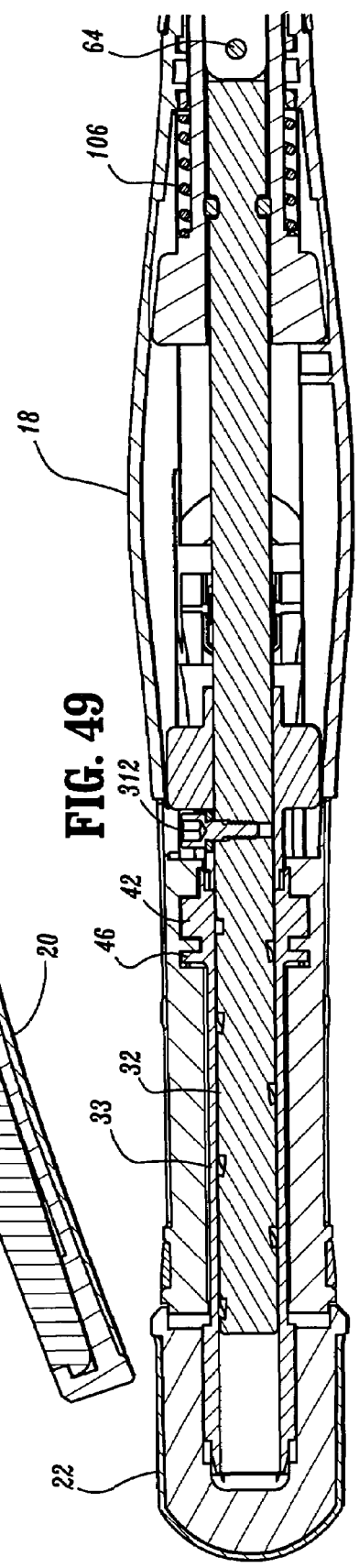
FIG. 48
FIG. 49

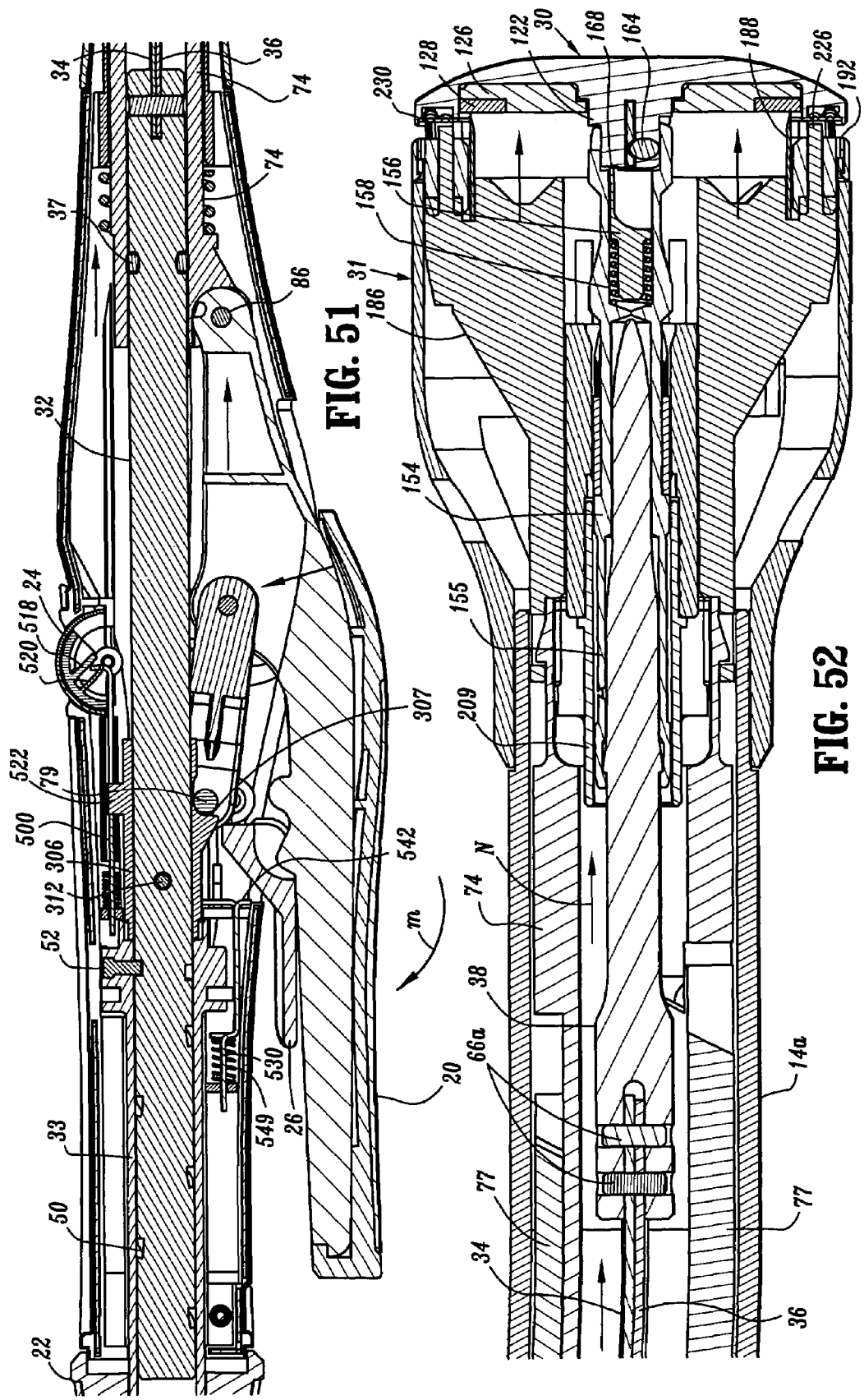

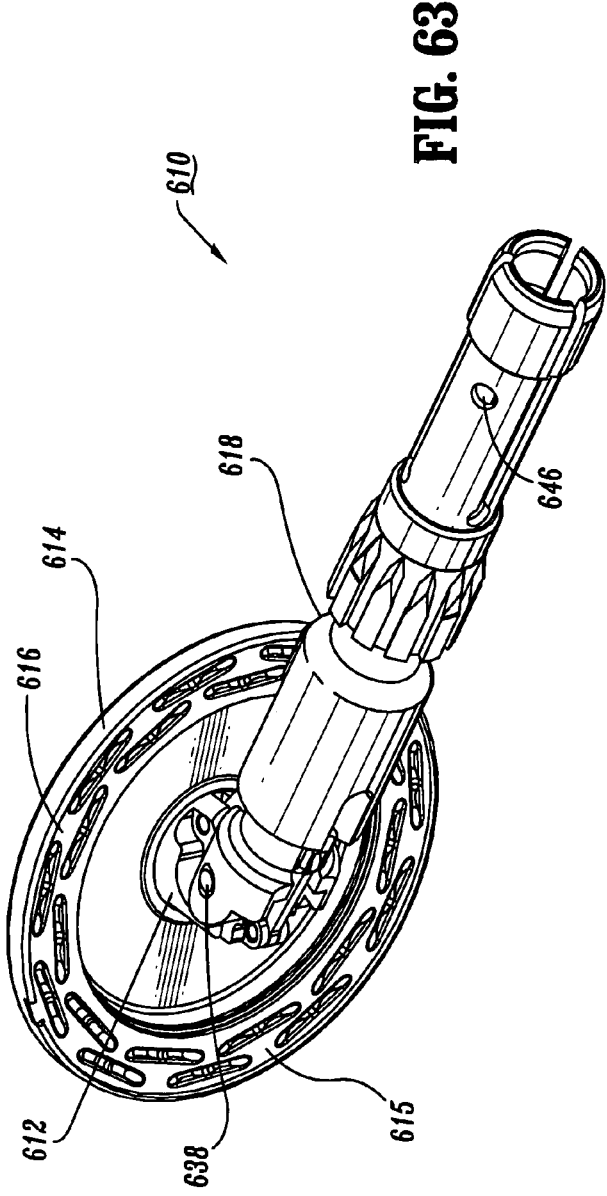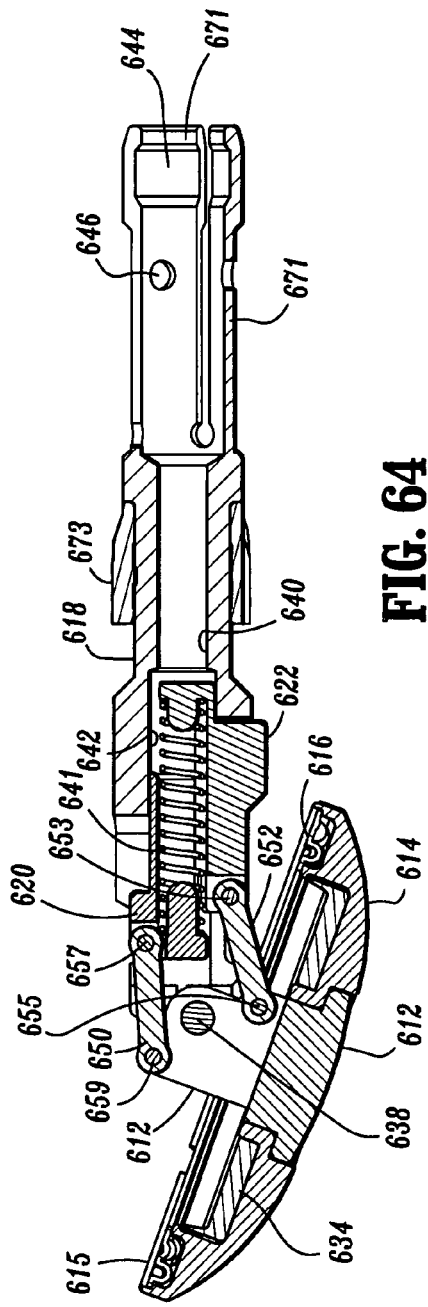

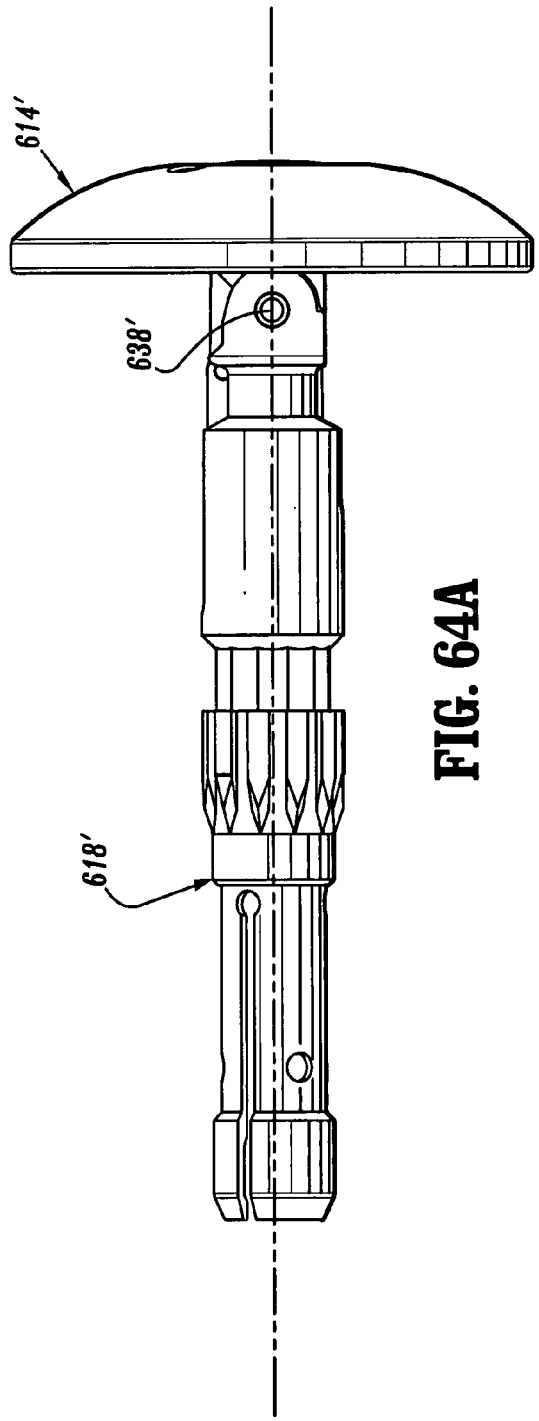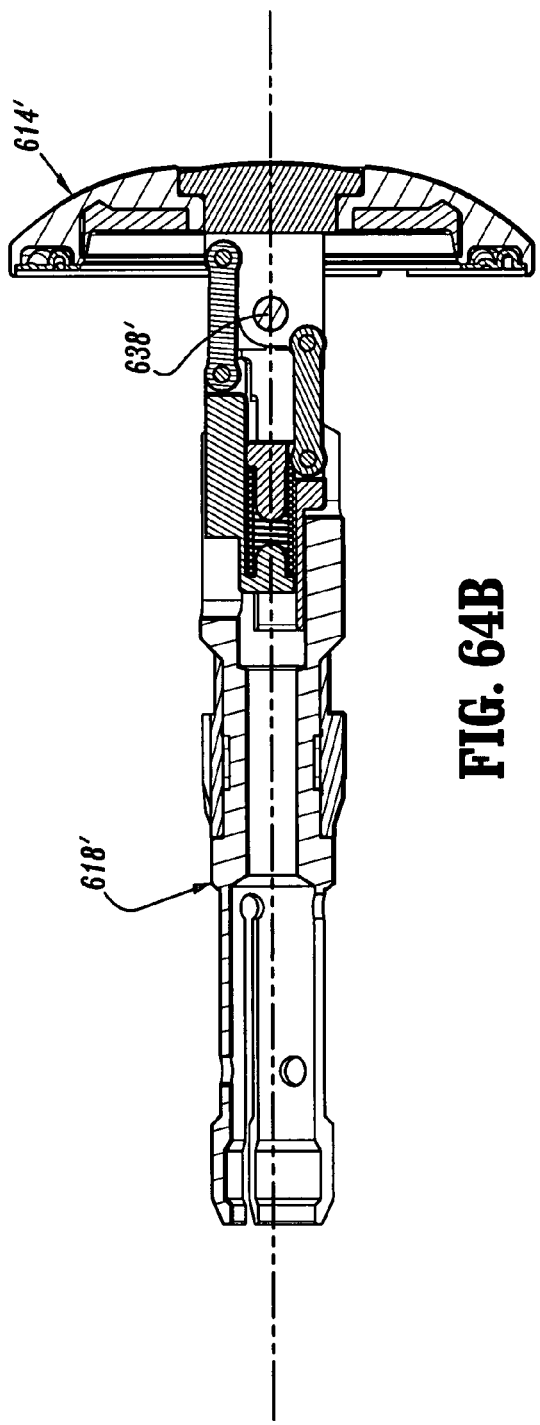

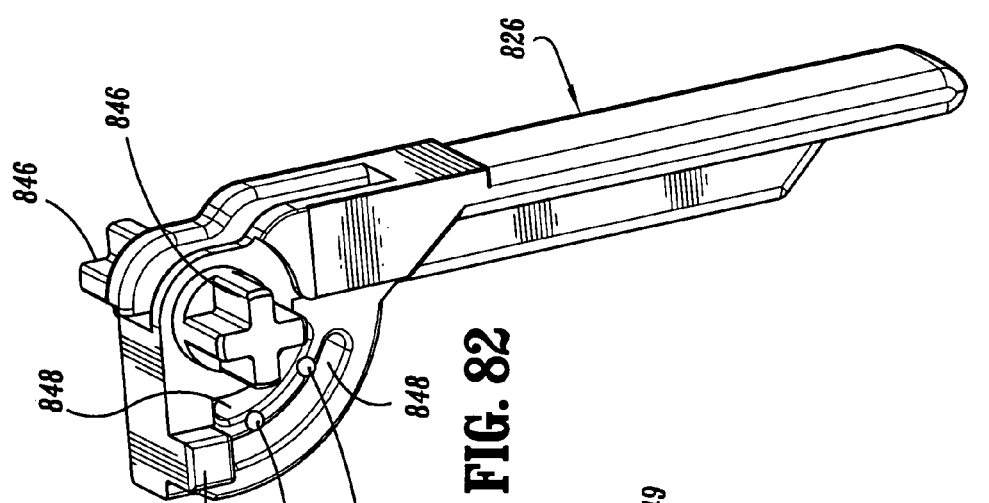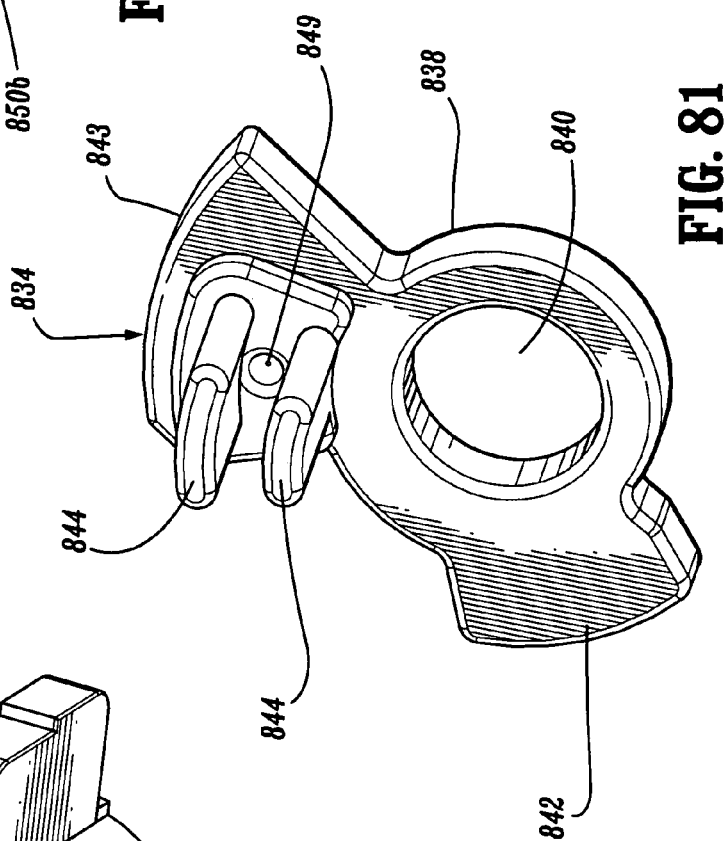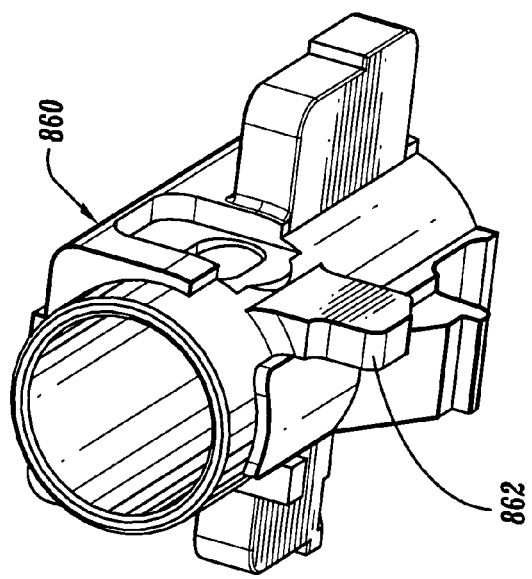

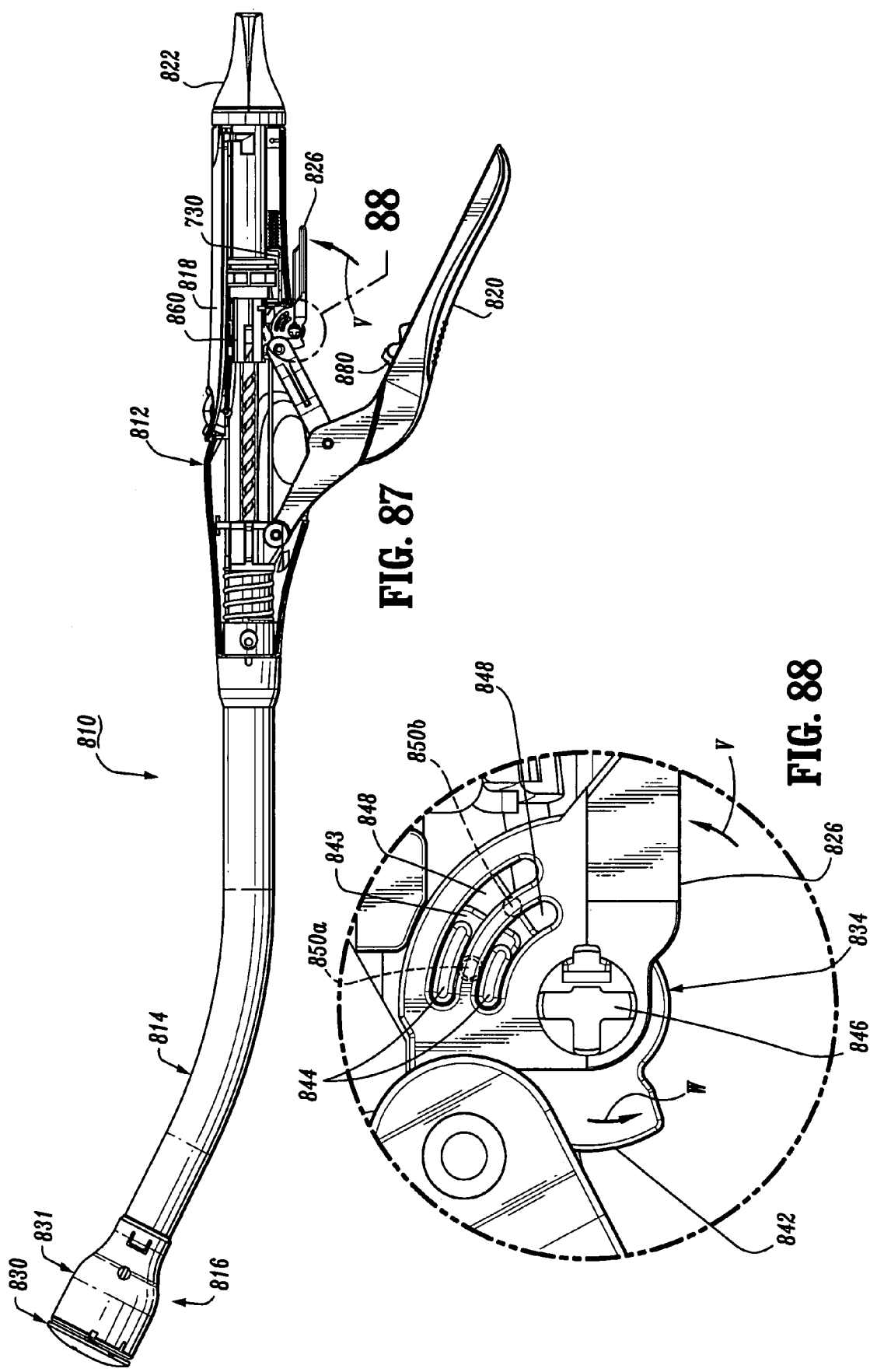

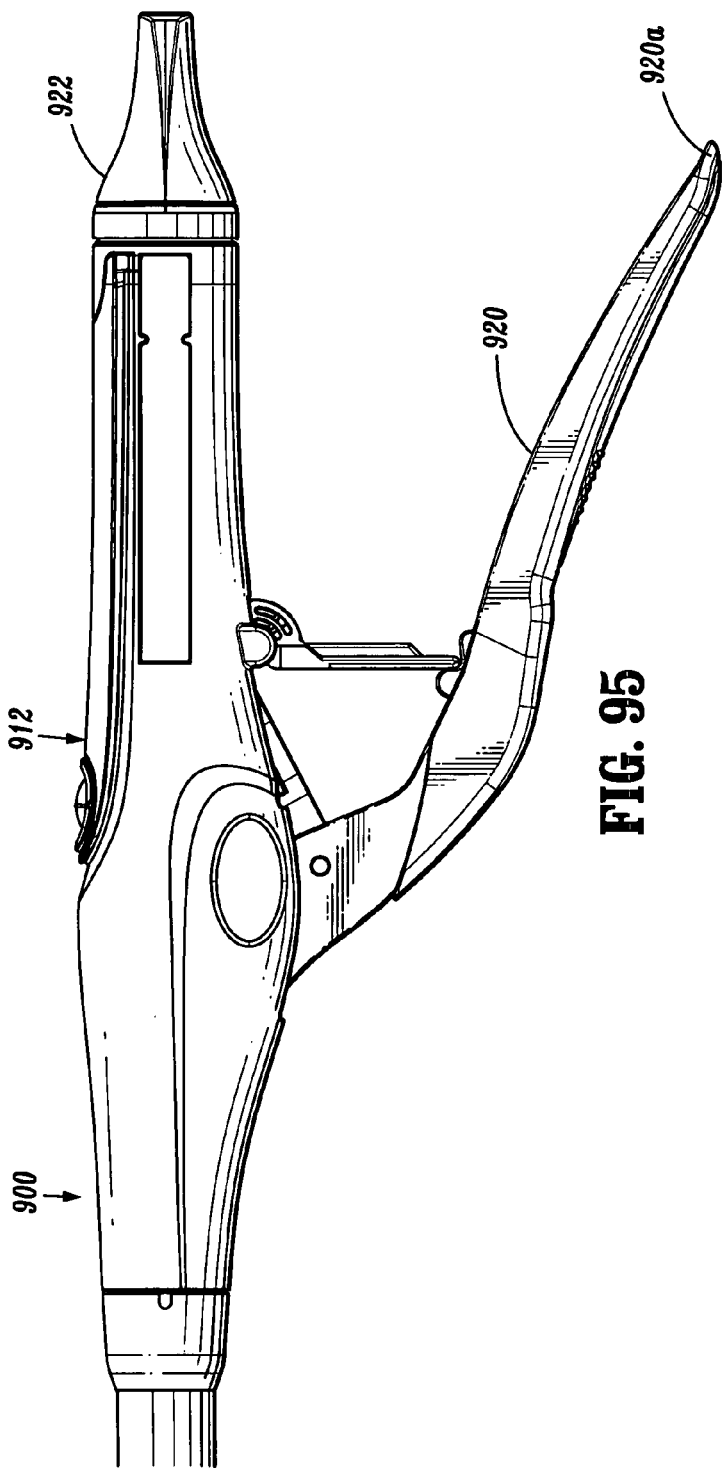
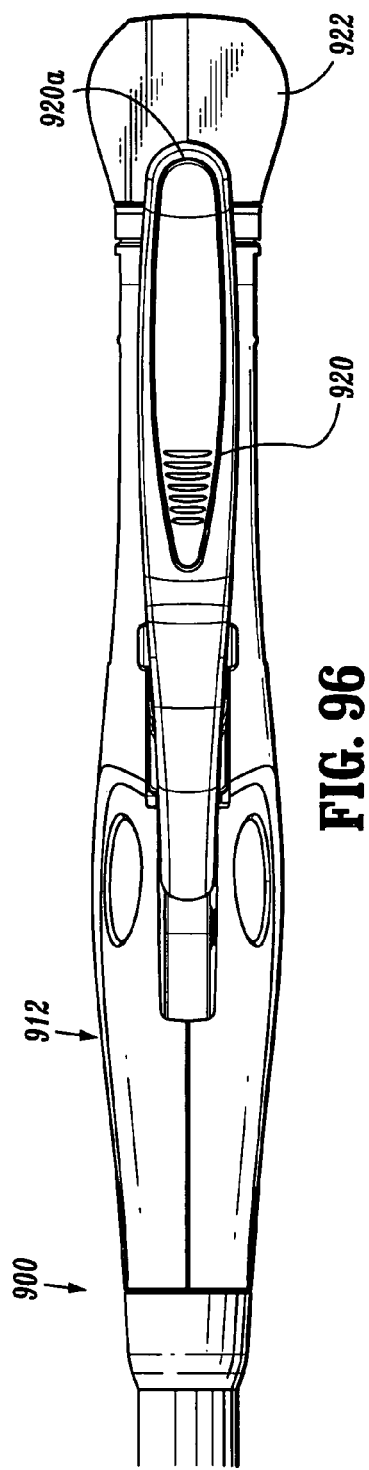
FIG. 95
FIG. 96

SURGICAL STAPLING DEVICE WITH TILTABLE ANVIL HEAD

This application is a continuation of U.S. application Ser. No. 10/968,722, filed Jan. 27, 2005, which claims priority from U.S. provisional Application Ser. No. 60/616,982, filed on Oct. 8, 2004, U.S. provisional Application Ser. No. 60/617,007, filed Oct. 8, 2004, U.S. provisional Application Ser. No. 60/512,482, filed Oct. 17, 2003, and U.S. provisional Application Ser. No. 60/512,405 filed Oct. 17, 2003, the entirety of each of which is incorporated herein by reference.

BACKGROUND

1. Technical Field

The present disclosure relates generally to a surgical stapling device for applying surgical staples to body tissue. More particularly, the present disclosure relates to a surgical stapling device suitable for performing circular anastomosis of hollow tissue organs.

2. Background to Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end of the elongated body to actuate the instrument and a staple holding component disposed at a distal end of the elongated body. An anvil assembly including an anvil rod with attached anvil head is mounted to the distal end adjacent the staple holding component. Opposed end portions of tissue of the organs to be stapled are clamped between the anvil head and the staple holding component. The clamped tissue is stapled by driving one or more staples from the staple holding component so that the ends of the staples pass through the tissue and are deformed by the anvil head.

Instruments for performing circular anastomosis procedures having anvil assemblies which are pivotable from an operative position to a tilted or non-operative position are known in the art. Such pivotable anvil assemblies lessen the trauma to a patient during insertion and/or removal of the anvil assembly into or from a body lumen.

During some procedures using such instruments, it is desirable to insert the anvil assembly of the instrument into a body lumen in the tilted position, return the anvil assembly to the operative position to perform the anastomosis procedure, and thereafter return the anvil assembly to its tilted position for removal of the anvil assembly and/or instrument from the body lumen. During other procedures, it is desirable to insert the anvil assembly into a body lumen in its operative position and move the anvil assembly to its tilted position prior to removal from the body lumen. In each of these procedures, it would be desirable for the anvil assembly to move automatically to its desired position.

Accordingly, a continuing need exists in the art for an improved stapling device having a tiltable anvil assembly which can achieve the above-mentioned objectives.

SUMMARY

In accordance with the present disclosure, a surgical stapling device is disclosed for performing circular anastomosis. The surgical stapling device includes a handle portion or assembly, a body portion and a head portion including an anvil assembly and a shell assembly. The handle portion can include a rotatable approximation knob for approximating the anvil and shell assemblies and a firing trigger for actuating a firing mechanism for ejecting staples positioned within the shell assembly from the shell assembly. In one embodiment, the firing trigger forms one link of a two bar linkage provided to actuate the firing mechanism. The two bar linkage provides the device with an improved mechanical advantage to reduce the firing forces required to fire the device.

In one embodiment, the head portion includes an anvil assembly which is normally in a tilted position and will automatically pivot to an operative position when the anvil assembly is attached to the surgical stapling device and return to the tilted position after the device has been fired and unapproximated. The tiltable anvil provides a reduced anvil profile to reduce trauma during insertion and removal of the device from a body lumen. The anvil assembly includes an anvil head and an anvil center rod. The anvil head is pivotally attached to the anvil center rod and is pivotable between the operative position and the tilted position. A biasing member is provided to urge the anvil head to its tilted position. The surgical stapling device includes an anvil retainer assembly having a locking member which is movable from a first position to a second position. In its first position, the locking member is positioned to move the anvil head to its operative upon attachment of the anvil head to the surgical stapling device. In its second position, the locking member is positioned to permit the anvil head to pivot to its tilted position. In one embodiment, the anvil retainer assembly includes a body portion defining a longitudinal bore and a trocar extending from a distal end of the longitudinal bore. The trocar forms the locking member and is movable from an advanced position to a retracted position by a biasing member, e.g., a coil spring. In its advanced or first position, the distal end of the trocar is positioned to engage a first slide member supported within the anvil center rod to urge the anvil head against the urging of the biasing member from its tilted position to its operative position. In its second position, the trocar is positioned to permit the anvil head to move from the operative position to the tilted position.

In one embodiment, the trocar includes an annular flange and the longitudinal bore defined by the body portion defines an internal shoulder. The biasing member is positioned between the annular flange and the shoulder to urge the trocar to its second or proximal position. A pivotable cam member is supported within a slot in the body portion. The cam member is pivotable from a first position to a second position. In the first position of the cam member, a distal finger of the cam member engages a proximal end of the trocar to retain the trocar in its first or distal position. In the second position, the cam member allows the trocar to move to its second or proximal position. In one embodiment, the distal finger includes an angled face such that engagement between the distal finger of the cam member and the proximal end of the trocar urges the cam member to its second position. A bushing supported within the shell assembly of the stapling device and a pair of arms provided on a pusher of the stapling device may be provided to prevent the cam member from moving to its second position until after the surgical stapling device has been fired.

In another embodiment, the head portion includes an anvil assembly having a head assembly including a housing, a post, an anvil plate and a backup member. The anvil head assembly is pivotally secured to an anvil center rod and movable between an operative position and a tilted position. The backup member is slidably positioned about the post and is movable from a first position to a second position. In its first position, the backup member prevents pivotal movement of the head assembly from the operative position to the tilted position. A retainer member is positioned between the head assembly housing and the backup member to prevent movement of the backup member to its second position until a predetermined force has been applied to the backup member. The retainer member can include an annular member having a plurality of deformable tabs. The deformable tabs are positioned to engage the backup member such that upon movement of the backup member from its first position to its second position, the tabs are deformed. Other deformable, compressible, crushable or movement restricting retaining members are envisioned.

The surgical stapling device may also include a firing lockout mechanism which prevents actuation of the firing trigger until the device has been approximated. In one embodiment, the firing lockout mechanism includes a trigger lock and a lockout member which is movably positioned in the handle assembly. The lockout member prevents movement of the trigger lock from a locked to an unlocked position until the device has been approximated.

In another embodiment, the surgical stapling device includes a passive lockout mechanism which prevents movement of the anvil assembly in relation to the shell assembly after the surgical stapling device has been approximated and the trigger lock has been moved to its unlocked position. The passive lockout mechanism includes an locking plate and a biasing member. The locking plate is releasably coupled to the trigger lock and includes a locking tab and a release tab. Movement of the trigger lock from its locked position to its unlocked position effects movement of the locking plate to a position in which the locking tab prevents unapproximation of the anvil assembly in relation to the shell assembly. The locking tab is moved to a position permitting unapproximation of the anvil assembly in relation to the shell assembly automatically upon actuation of the firing trigger.

BRIEF DESCRIPTION OF THE DRAWINGS

Various embodiments of the presently disclosed surgical stapling device are disclosed herein with reference to the drawings wherein:

FIG. 1 is a top side perspective view from the proximal end of the presently disclosed surgical stapling device in the unapproximated position;

FIG. 2 is a top side perspective view from the distal end of the surgical stapling device shown in FIG. 1;

FIG. 3 is a side perspective exploded view of the handle assembly of the surgical stapling device shown in FIG. 1;

FIG. 3A is a top perspective view of the indicator of the handle assembly shown in FIG. 3;

FIG. 7B is a side view of the anvil retainer shown in FIG. 7A;

FIG. 7C is a cross-sectional view taken along section lines 7C-7C of FIG. 7B;

FIG. 10 is a side perspective exploded view from the proximal end of the anvil assembly of the surgical stapling device shown in FIG. 1;

FIG. 10A is a side perspective exploded view of another embodiment of the anvil assembly;

FIG. 10B is a side perspective view from the distal end of the retainer member of the anvil assembly shown in FIG. 10A;

FIG. 10C is a side cross-sectional view of the anvil assembly shown in FIG. 10A with the anvil head in the operative position prior to deformation of the retainer member;

FIG. 10D is an enlarged view of the indicated area of detail shown in FIG. 10C;

FIG. 11 is a side perspective view of the retaining clip of the anvil assembly shown in FIG. 10;

FIG. 12 is a side perspective view of the distal end of the center rod of the anvil assembly shown in FIG. 10 with a removable trocar fastened thereto;

FIG. 13 is a side perspective view of the center rod and removable trocar shown in FIG. 11 separated one from the other;

FIG. 16 is a side cross-sectional view taken through the retaining clip of the anvil assembly and removable trocar of the anvil assembly shown in FIG. 15;

FIG. 16A is a side view of an alternate embodiment of the anvil assembly shown in FIG. 14;

FIG. 16B is a side cross-sectional view of the anvil assembly shown in FIG. 16A taken through the retaining clip;

FIG. 17 is an enlarged view of the indicated area of detail shown in FIG. 16;

FIG. 18 is a side cross-sectional view taken through the pivot member of the anvil head assembly of the anvil assembly shown in FIG. 15;

FIG. 19 is a side perspective view from the proximal end of the anvil assembly shown in FIG. 18 with the removable trocar removed;

FIG. 36 is a perspective view from the front of the distal end of the surgical stapling device shown in FIG. 35 with an anvil assembly attached thereto;

FIG. 37 is a side cross-sectional view of the distal end of the surgical stapling device shown in FIG. 36;

FIG. 39 is a cross-sectional view taken along section lines 39-39 of FIG. 38;

FIG. 40 is a cross-sectional view taken along section lines 40-40 of FIG. 38;

FIG. 41 is a cross-sectional view taken along section lines 41-41 of FIG. 38;

FIG. 42 is a cross-sectional view taken along section lines 42-42 of FIG. 38;

FIG. 43 is a cross-sectional view taken along section lines 43-43 of FIG. 38;

FIG. 44 is a cross-sectional view taken along section lines 44-44 of FIG. 38;

FIG. 48 is a side cross-sectional view of the handle assembly of the surgical stapling device shown in FIG. 45;

FIG. 49 is a top horizontal cross-sectional view of a portion of the handle assembly of the surgical stapling device shown in FIG. 45;

FIG. 51 is a side cross-sectional view of a portion of the handle assembly of the surgical stapling device shown in FIG. 45 after the firing trigger has been actuated;

FIG. 52 is a side cross-sectional view of the distal end of the surgical stapling device shown in FIG. 45 after the firing trigger has been actuated;

FIG. 63 is a side perspective view from the proximal end of another embodiment of the anvil assembly for use with the surgical stapling device shown in FIG. 62;

FIG. 64 is a side cross-sectional view of the anvil assembly shown in FIG. 63;

FIG. 64A is a side view of another embodiment of the anvil assembly shown in FIG. 63;

FIG. 64B is a side cross-sectional view of the anvil assembly shown in FIG. 64A;

FIG. 80 is a side perspective view from the proximal end of the screw stop of the surgical stapling device shown in FIG. 75;

FIG. 81 is a side perspective view of the interlock plate of the surgical stapling device shown in FIG. 75;

FIG. 82 is a side perspective view of the trigger lock of the surgical stapling device shown in FIG. 75;

FIG. 87 is a side view of the surgical stapling device shown in FIG. 83 with a handle half-section removed, the anvil head in an approximated position, and the trigger lock moved to its unlocked position;

FIG. 88 is an enlarged view of the indicated area of detail shown in FIG. 87;

FIG. 95 is a side view of the handle assembly of another embodiment of the presently disclosed surgical stapling device; and FIG. 96 is a bottom view of the handle assembly shown in FIG. 95.

DETAILED DESCRIPTION OF PREFERRED EMBODIMENTS

Figure 3B:
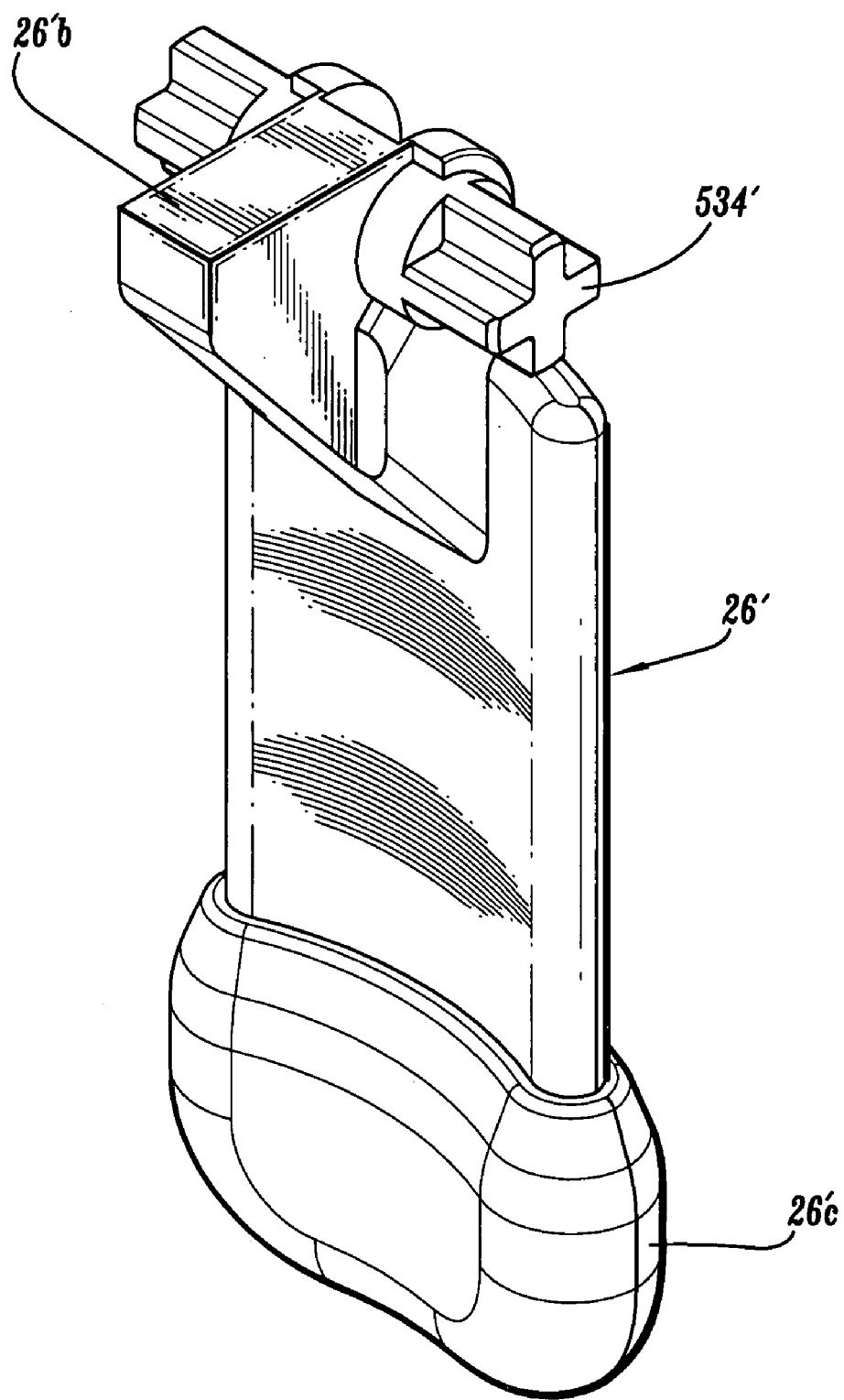
FIG. 3B is a side perspective view of an alternate embodiment of the trigger lock of the handle assembly shown in FIG. 3.

Embodiments of the presently disclosed surgical stapling device will now be described in detail with reference to the drawings in which like reference numerals designate identical or corresponding elements in each of the several views.

Throughout this description, the term "proximal" will refer to the portion of the instrument closest to the operator and the term "distal" will refer to the portion of the instrument furthest from the operator.

FIGS. 1 and 2 illustrate one embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. In one embodiment, stationary handle 18 is formed from thermoplastic handle sections 18a and 18b, e.g., polycarbonate, (FIG. 3) which together define a housing for the internal components of handle assembly 12. Handle sections 18a and 18b can be secured together by sonic welding. Alternately, other known securement techniques may be employed including screws, adhesives, snap-fit connectors, etc. The internal components of handle portion 12 will be discussed in detail below. In one embodiment, cushioned and/or resilient slip resistant portions such as a grip (not shown) can be fastened to or included as part of handle sections 18a and 18b and firing trigger 20. The slip resistant grip may be formed over handle sections 18a and 18b and firing trigger 20 using an overmolding procedure and may be formed from neoprene or rubber. Alternately, other suitable materials, e.g., elastomeric materials, and joining techniques may be employed. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. In one embodiment, indicator 24 has a bulbous or convex shape which extends outwardly from a top surface of handle sections 18a and 18b and is easily viewable by a surgeon from the top and sides of the stapling device. A magnification lens may be positioned over indicator 24 to further improve visualization of the indicia.

Head portion 16 includes an anvil assembly 30 and a shell assembly 31. Each of these assemblies will be discussed in detail below. Except where otherwise noted, the components of surgical device 10 are generally formed from thermoplastics including polycarbonates, and metals including stainless steel and aluminum. The particular material selected to form a particular component will depend upon the strength requirements of the particular component. For example, the anvil may be formed from a metal, such as stainless steel, and the stationary handle may be formed from a thermoplastic such as polycarbonate. Alternately, other materials not listed above, which can withstand sterilization procedures, may be used to form components of stapling device 10 provided the materials are suitable for surgical use and meet the strength requirements of the particular component.

Figure 4:
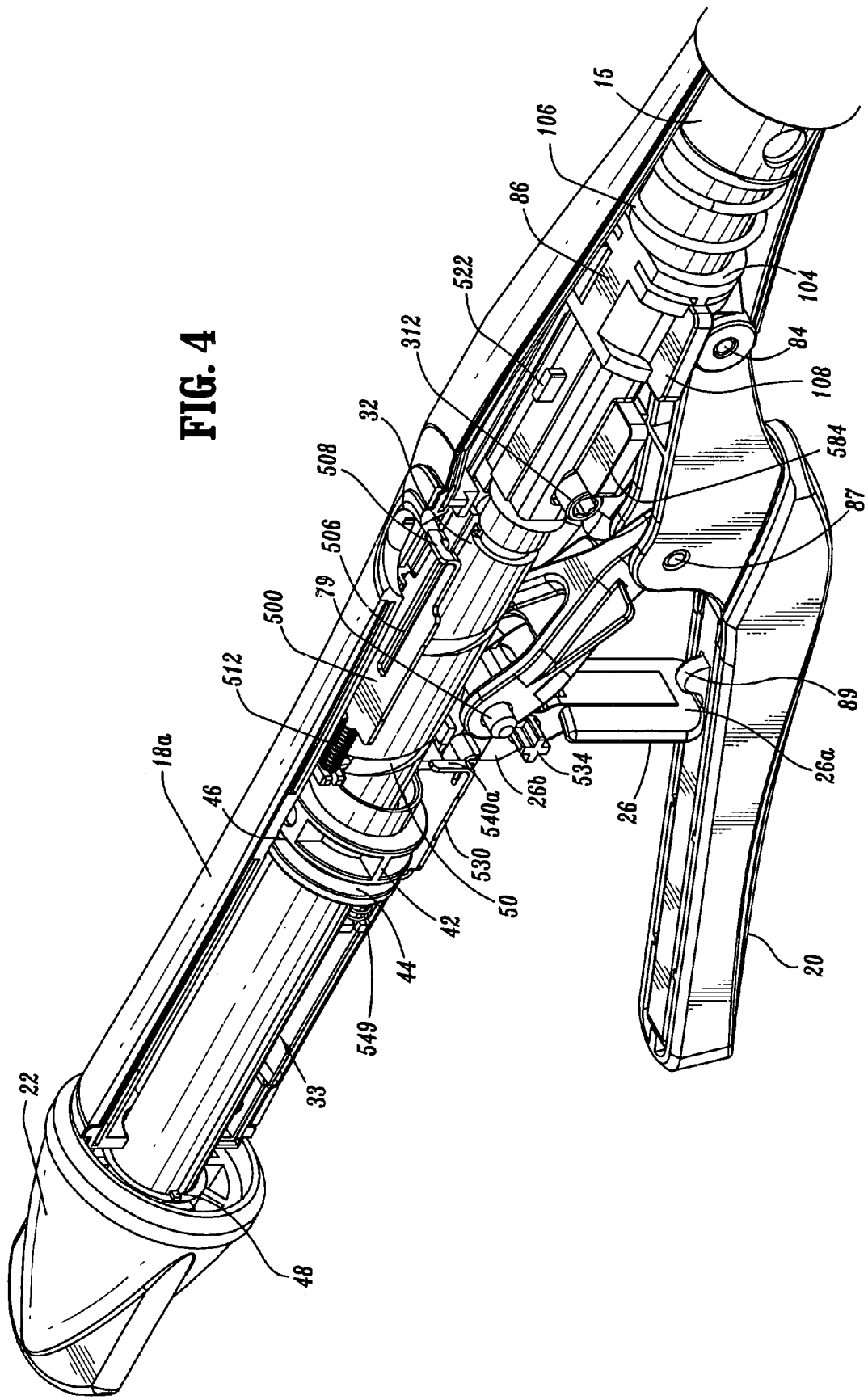
FIG. 4 is a side perspective view from the top of the handle assembly of the surgical stapling device shown in FIG. 1 with a handle section removed.
Figure 5:
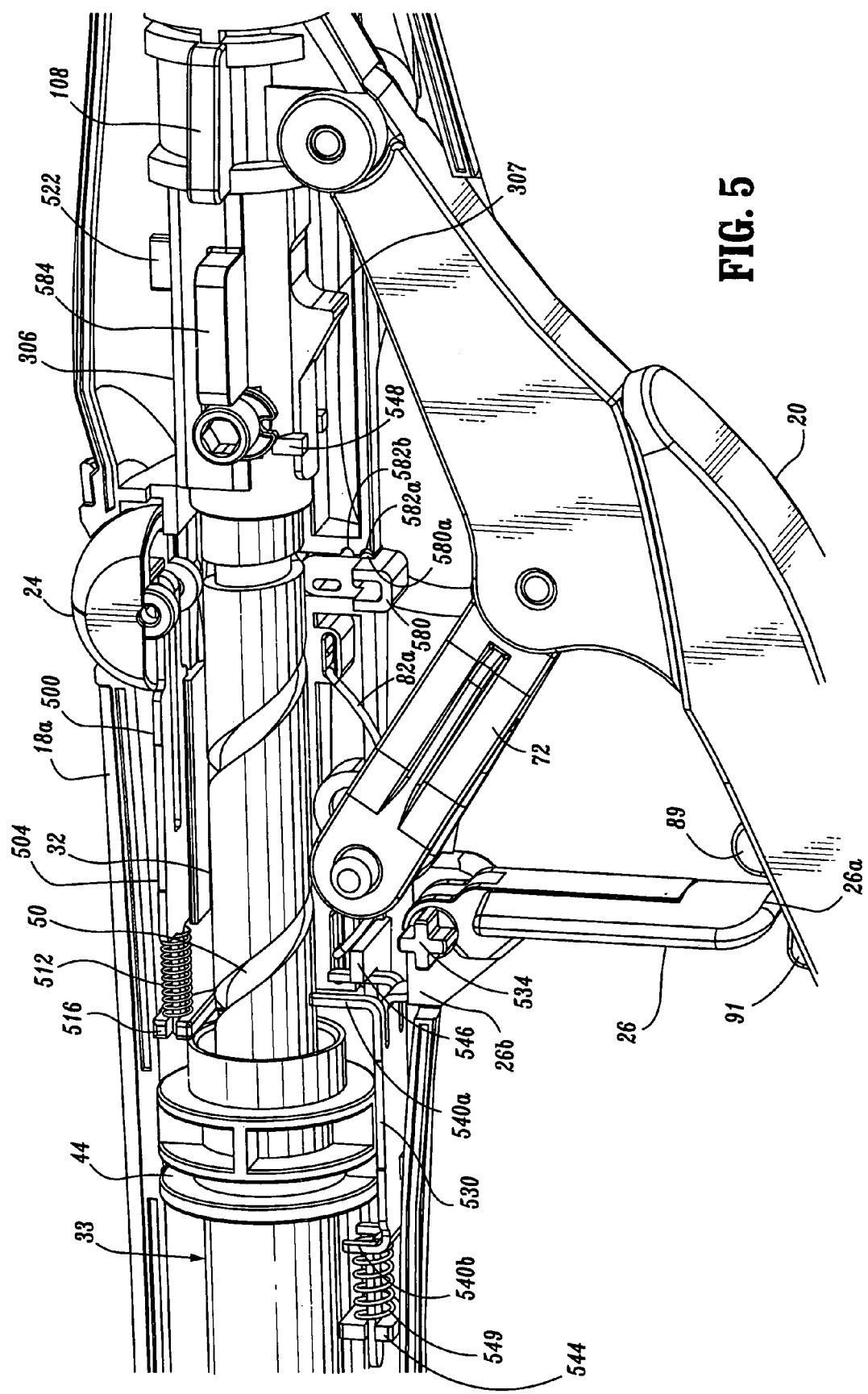
FIG. 5 is a side perspective view from the bottom of the handle assembly of the surgical stapling device shown in FIG. 4.
Figure 6:
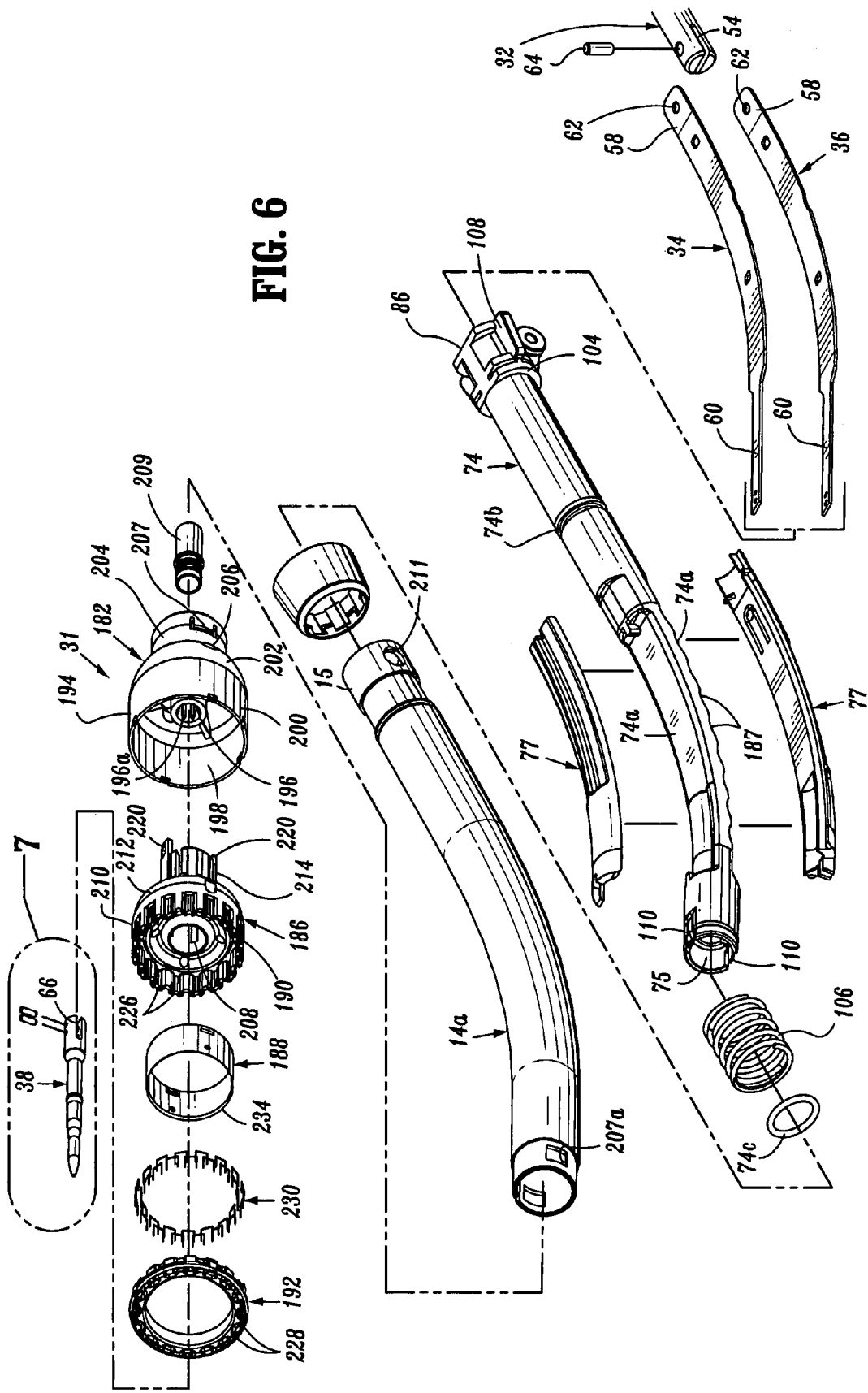
FIG. 6 is a side perspective exploded view of the central body portion and distal head portion of the surgical stapling device shown in FIG. 1.
Figure 7:
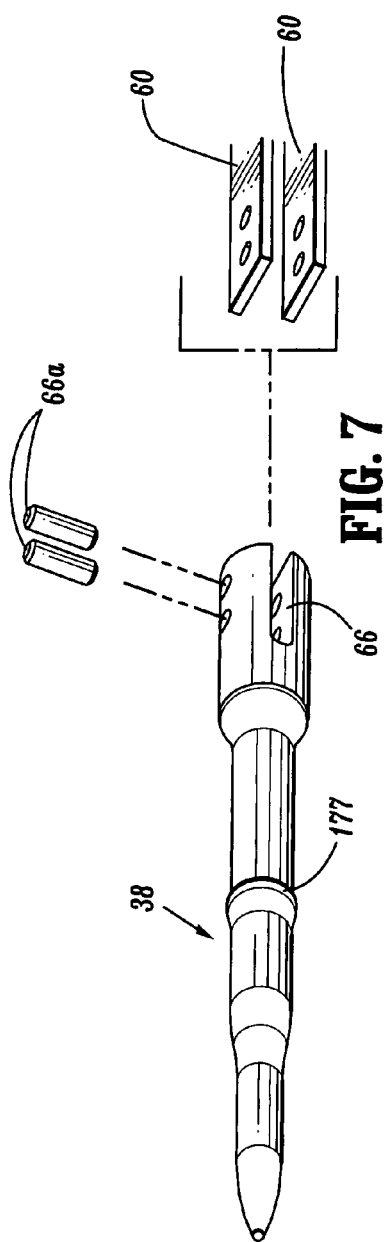
FIG. 7 is an enlarged side perspective of the anvil retainer and distal end of the band portions of the central body portion shown in FIG. 6.

FIGS. 3-5 illustrate the internal components of handle assembly 12. The internal components include the proximal components of approximation and firing mechanisms, a firing lockout mechanism and an indicator drive mechanism. FIGS. 6 and 7 illustrate the internal components of elongated body portion 14. These components include the distal components of the approximation and firing mechanisms. Each of these mechanisms will be disclosed in detail hereinbelow.

Approximation Mechanism

Referring to FIGS. 3-8, the approximation mechanism includes approximation knob 22, a drive screw 32, a rotatable sleeve 33, first and second screw extensions 34 and 36 (FIG. 6), respectively, and an anvil retainer 38. Rotatable sleeve 33 includes a substantially cylindrical hollow body portion 40 and a substantially cylindrical collar 42 which together define a central bore 33a. Collar 42 has an annular groove 44 formed thereabout which is dimensioned to receive an inwardly extending flange 46 formed on an inner wall of handle sections 18a and 18b. Engagement between groove 44 and flanges 46 axially fixes sleeve 33 within handle 18 while permitting rotation of sleeve 33 in relation to stationary handle 18. The proximal end of body portion 40 of rotatable sleeve 33 extends through an opening 18b in the proximal end of stationary handle 18. A pair of diametrically opposed elongated ribs 48 are positioned or formed on the outer surface of body portion 40. Approximation knob 22 includes a pair of internal slots 49a positioned to receive ribs 48 of sleeve 33 to rotatably fix sleeve 33 to knob 22, such that rotation of knob 22 causes concurrent rotation of sleeve 33.

The proximal portion of screw 32 includes a helical channel 50 and is dimensioned to be slidably positioned within central bore 33a of rotatable sleeve 33. The distal end of screw 32 includes an annular recess 35 dimensioned to receive a seal member 37 (FIG. 3) for providing a fluid tight seal between the outer surface of screw 32 and the inner surface of pusher link 74. A pin 52 (FIG. 3) extends radially through cylindrical collar 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18.

Figure 8:
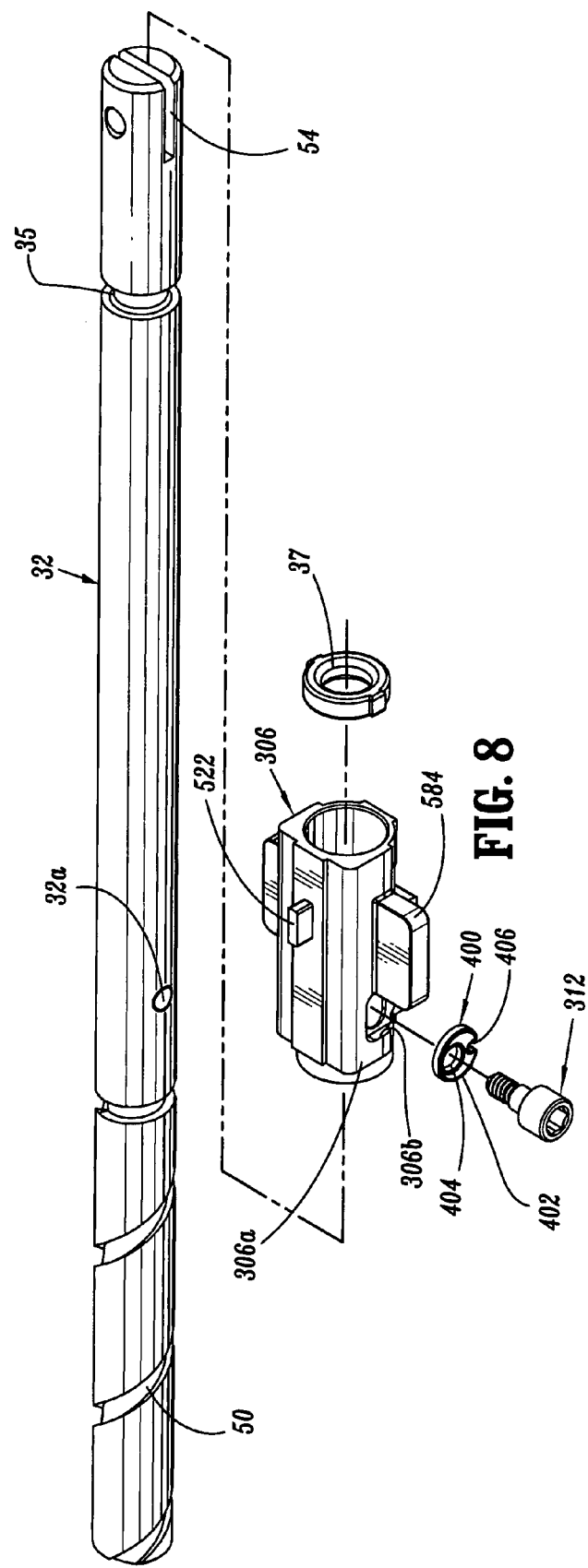
FIG. 8 is a side perspective view of the screw and screw stop of the approximation mechanism of the handle assembly shown in FIG. 5.

Referring to FIGS. 6-8, the distal end of screw 32 includes a transverse slot 54. Top and bottom screw extensions 34 and 36 (FIG. 6) each include a proximally located flexible flat band portion 58 and a distally located flat band portion 60. Alternately, it is envisioned that screw extensions 34 and 36 may have other than a band configuration. For example, screw extensions 34 and 36 may be semi-circular or circular in cross-section. The flexibility of top and bottom screw extensions 34 and 36 permits movement of screw extensions 34 and 36 through curved elongated body portion 14. The proximal end of each band portion 58 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 7) to fasten anvil retainer 38 to the distal end of screw extensions 34 and 36. In one embodiment, a pair of pins 66a which extend through the proximal end of anvil retainer 38 and band portions 60 are used to secure screw extensions 34 and 36 to anvil retainer 38. Alternately, band portions 60 can be brazed or welded within slot 66 or other fastening techniques may be used to secure band portions 60 of screw extensions 34 and 36 to anvil retainer 38, e.g., screws, crimping, etc.

Anvil retainer 38 includes a trocar portion 38a, a body portion 38b and an attachment portion 38c. Trocar portion 38a includes a blunt trocar tip 39. Body portion 38b is substantially cylindrical and has a diameter which is larger than the diameter of trocar portion 38a. An annular protrusion 177 (FIG. 7) which is configured to engage the anvil assembly in a manner to be discussed in detail below is positioned about body portion 38b of anvil retainer 38 at a location spaced from trocar portion 38a.

Figure 7A:
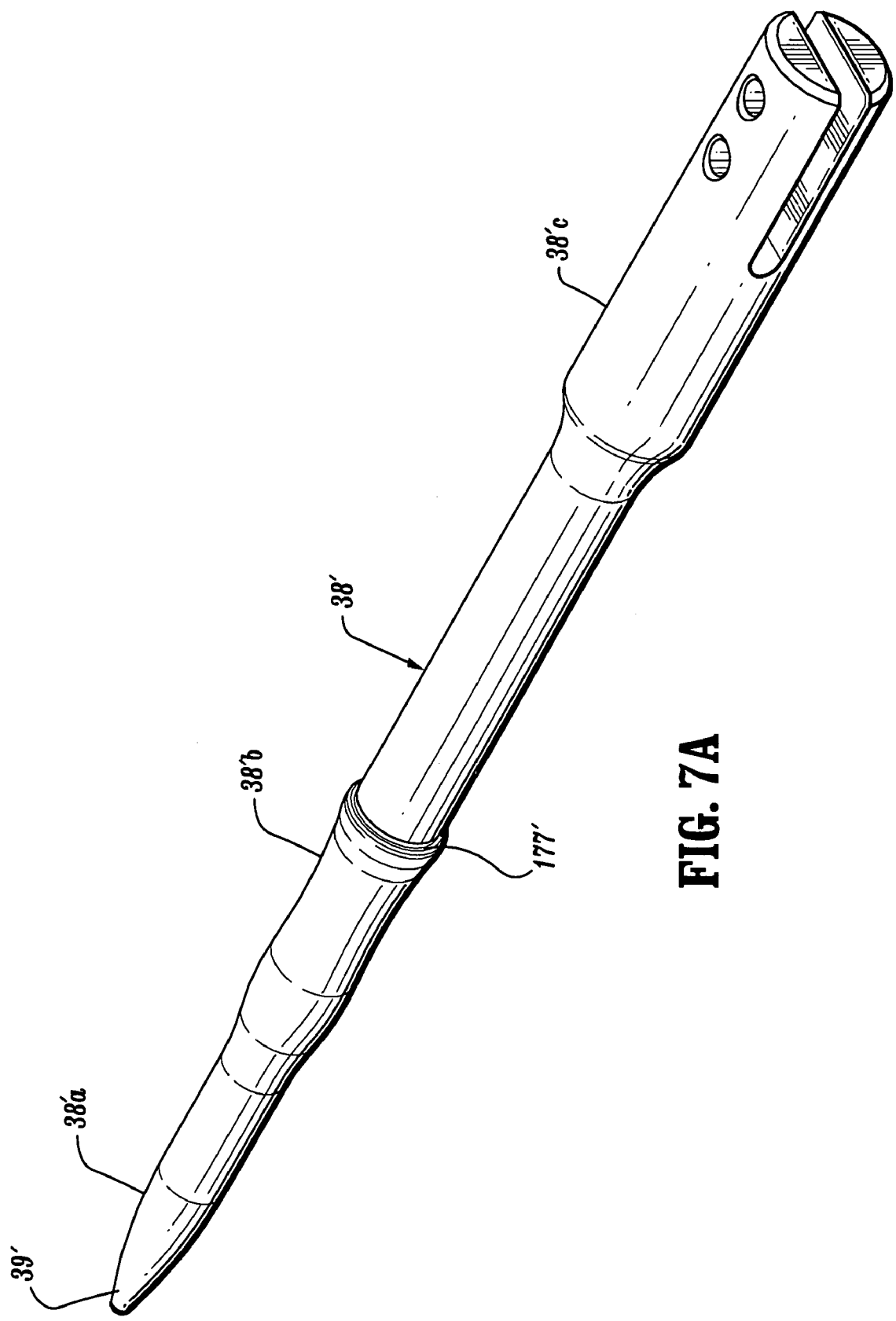
FIG. 7A is a side perspective view from the proximal end of an alternate embodiment of the anvil retainer shown in FIG. 7.
Figure 9A:
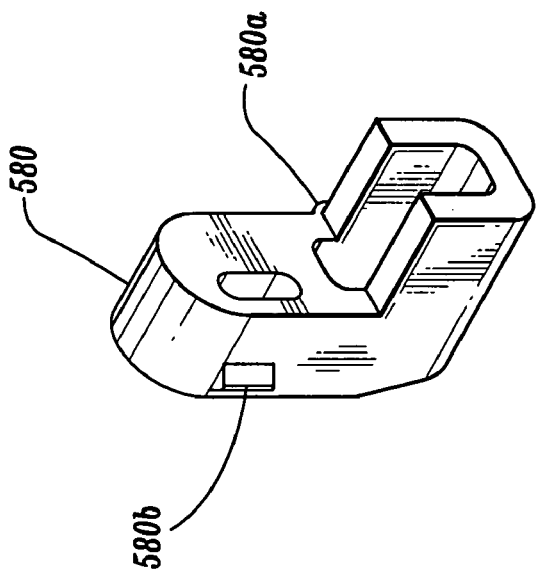
FIG. 9A is a side perspective view from the top of the abutment member of the handle assembly shown in FIG. 3.
Figure 9:
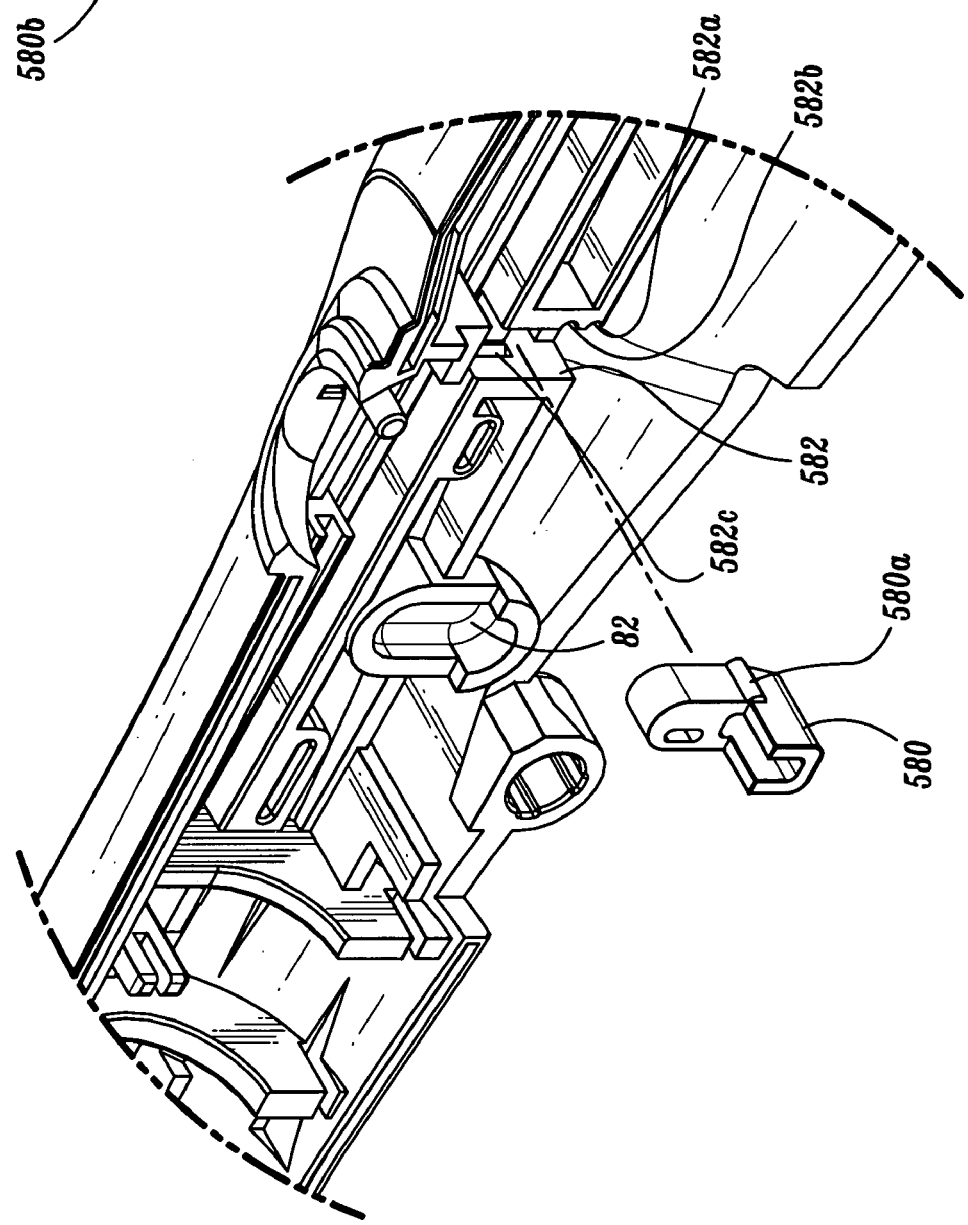
FIG. 9 is an enlarged view of the indicated area of detail shown in FIG. 3.

FIGS. 7A-7C illustrate an alternate embodiment of anvil retainer 38 shown generally as 38'. Anvil retainer 38' includes a trocar portion 38'a, a body portion 38'b and an attachment portion 38'c. Attachment portion 38'c is substantially the same as attachment portion 38c above and will not be discussed in further detail. Trocar portion 38' includes a blunt trocar tip 39'. A protrusion 177' is formed about body portion 38'b at a location spaced proximally of trocar portion 38a to facilitate engagement with an anvil assembly. Body portion 38'b between trocar portion 38'a and protrusion 177' defines a smooth concavity or coke-bottle shape. The shape permits tissue to slide over the anvil retainer prior to attachment to an anvil assembly. Alternately, protrusion 177 need not be annular or may include different attachment structure, e.g., recesses, grooves, etc.

Referring again to FIGS. 3-7, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18. As a result, top and bottom screw extensions 34 and 36, which are fastened to the distal end of screw 32, and anvil retainer 38, which is fastened to the distal end of screw extensions 34 and 36, are moved axially within elongated body portion 14. Since anvil assembly 30 is secured to the distal end of anvil retainer 38, rotation of approximation knob 22 will effect movement of anvil assembly 30 in relation to shell assembly 31 between spaced and approximated positions.

Firing Mechanism

Referring to FIG. 3-6 and 9, the firing mechanism includes firing trigger 20, a firing link 72 and an elongated pusher link 74 (FIG. 6). Firing trigger 20 includes a body portion 76 and a trigger cover 80. A cushioned gripping surface (not shown) which may be formed of neoprene or rubber may be provided on trigger cover 80. The cushioned gripping surface provides a non-slip and/or cushioned surface to make actuation of device 10 more comfortable to a surgeon. The distal end of body portion 76 of trigger 20 is pivotally connected to a coupling member 86 by a pivot member 84. Coupling member 86 is secured to the proximal end of pusher link 74 and may be formed integrally with pusher link 74 or as a separate element fastened thereto. Firing link 72 has a distal end pivotally secured to body portion 76 of trigger 20 by a pivot member 87 and a second end pivotally secured within a vertical slot 82 formed between stationary handle half-sections 18a and 18b of stationary handle 18 by pivot member 79. Pivot member 79 is free to move vertically within slot 82. A spring 82a (FIG. 9) is supported within handle 18 to urge pivot member 79 downwardly towards the bottom of slot 82. Body portion 76 of trigger 20 further includes a pair of abutments including an abutment 89 and an abutment 91 which are positioned to engage the distal end 26a (FIG. 4) of trigger lock 26 in a manner to be described in greater detail below to prevent actuation of trigger 20 prior to approximation of device 10.

Coupling member 86 which is supported on the proximal end of elongated pusher link 74 includes a flange 104 (FIG. 6). A spring 106 is positioned between a proximal end 15 of outer tube 14a and flange 104 (FIG. 4) to bias pusher link 74 proximally to a retracted, non-fired position. A pair of wings 108 extend radially outwardly from coupling member 86. Wings 108 are dimensioned to slide along channels 111 (FIG. 3) formed along the internal walls of stationary handle 18 to maintain proper alignment of pusher link 74 within stationary handle 18 during firing of device 10.

Referring to FIG. 6, the distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 can be formed from a flexible plastic material and includes a plurality of notches 187 which allow the pusher link to bend more easily as it moves through body 14. Pusher link 74 defines a hollow channel 75 for slidably receiving the approximation mechanism. A flat surface or cutout 74a (FIG. 6) is formed in both sides of pusher link 74 and on one side slidably supports screw extensions 34 and 36 which are positioned in juxtaposed alignment. Spacers 77 are positioned within outer tube 14a adjacent cutout 74a to provide additional support for screw extensions 34 and 36 and pusher link 74 to prevent each component from buckling during actuation. An annular channel 74b is formed about pusher link 74 to receive an O-ring seal 74c. Pusher link 74 is slidably positioned within body portion 14 such that O-ring 74c seals the space between pusher link 74 and an internal wall of outer tube 14a. Operation of the firing mechanism of the device will be described in detail below.

Referring again to FIGS. 3-6 and 9, when firing trigger 20 is actuated, i.e., pivoted about pivot member 84, firing link 72 is moved proximally until pivot member 79 engages an abutment surface 307 (FIG. 25A-D) formed on screw stop 306 (FIG. 3). Screw stop 306 is axially fixed to screw 32 in a manner to be described in detail below. Thereafter, firing trigger 20 is pushed distally to advance pusher link 74 distally against the bias of spring 106. Since the distal end of pusher link 74 is connected to pusher back 186, actuation of firing trigger 20 effects advancement of pusher back 186 within shell assembly 31 to eject staples from shell assembly 31 in a manner to be described below.

Anvil Assembly

Referring to FIGS. 10-21, anvil assembly 30 includes an anvil head assembly 120 and an anvil center rod assembly 152. Anvil head assembly 120 includes a post 122, an anvil head 124, a backup plate 126, a cutting ring 128, a retaining clip 127 and an anvil 129. Post 122 is centrally positioned through a bore in anvil head 124. Alternately, post 122 may be integrally formed with anvil head 124. Anvil 129 is supported on anvil head 124 in an outer annular recess 136 and includes a plurality of pockets 140 for receiving and deforming staples. At least one tab 129a extends radially outwardly from anvil 129 and is dimensioned to be received within a cutout 124a formed in anvil head 124. Tab 129a and cutout 124a function to align anvil 129 within annular recess 136.

Backup plate 126 includes a central opening 126b which is positioned about post 122 within an inner recess 134 of anvil head 124 between post 122 and annular recess 136. Backup plate 126 includes a raised platform 126a. Cutting ring 128 includes an opening 128a having a configuration substantially the same as platform 126a. Although platform 126a is illustrated as having a circular shape, other platform configurations are envisioned. Alternately, a platform need not be provided. In one embodiment, cutting ring 128 is formed from polyethylene and is fixedly secured to backup plate 126 using, for example, an adhesive. Backup ring 126 can be formed from metal and provides support to cutting ring 128 to enhance the cutting of tissue. Alternately other materials of construction may be used to construct plate 126 and ring 128. Cutting ring 128 and backup plate 126 are slidably mounted about post 122. Backup plate 126 includes a pair of inwardly extending tabs 150 which will be described in further detail below.

Anvil center rod assembly 152 includes anvil center rod 154, a plunger 156 and plunger spring 158. A first end of center rod 154 includes a transverse throughbore 160 which is offset from the central longitudinal axis of center rod 154. Post 122 of anvil head assembly 120 also includes a transverse throughbore 162. A pivot member 164 pivotably secures post 122 to center rod 154 such that anvil head assembly 120 is pivotably mounted to anvil center rod assembly 152. Plunger 156 is slidably positioned in a bore 154b (FIG. 16) formed in the first end of center rod 154. Plunger 156 includes an engagement finger 168 which is offset from the pivot axis of anvil head assembly 120 and biased into engagement with base 122a of post 122 by plunger spring 158 to urge anvil head assembly 120 to a pivoted position at an angle to center rod 154. In a preferred untilted position, tabs 150 formed on backup plate 126 engage a top surface 154a (FIG. 20) of center rod 154 to prevent anvil head assembly 120 from pivoting about pivot member 164. As device 10 is fired, backup plate 126 and cutting ring 128 are moved or slide deeper into anvil recess 134 of anvil head 124 about post 122 (FIG. 21) by knife 188 (FIG. 6) in a manner to be described in further detail below to move tabs 150 out of engagement with top surface 154a of center rod 154 to permit plunger 156 to pivot anvil head assembly 120 about pivot member 164.

Referring to FIGS. 1A-F, in an alternate embodiment of the anvil assembly shown generally as 30' a retainer member 131 is positioned in inner annular recess 134 between backup plate 126 and a back wall of anvil head 124. In one embodiment, retainer member 131 is annular and includes a plurality of deformable tabs 131a which engage a rear surface of backup plate 126. Retainer member 131 prevents backup plate 126 and cutting ring 128 from moving into annular recess 134 of anvil head 124 until a predetermined force sufficient to deform tabs 131a has been applied to the backup member. The predetermined force sufficient to deform tabs 131a has been applied to the backup member. The predetermined force can be close to but is less than the force applied by an annular cutting blade of a surgical stapling device when it engages the backup member of the anvil assembly device. In one embodiment, the predetermined force is between about ten pounds and about ninety pounds and can be about fifty pounds. When the predetermined force is reached, e.g., during cutting of tissue, backup plate 126 will move from a first position to a second position within inner annular recess 134 of anvil head 124 and compress retainer member 131. It is envisioned that other crushable, deformable, collapsible or movement restricting members may be used to retain the backup member in a fixed position until the predetermined force has been applied to the backup member.

A retainer clip 127 is positioned in a transverse slot 122c formed in post 122 and includes a pair of outwardly biased flexible arms 127a and 127b. Arm 127b includes a recess 127c dimensioned to receive pivot pin 164 (FIG. 17). Prior to firing device 10, arms 127a and 127b are deformed inwardly by backup plate 126 (FIG. 17). After device 10 has been fired and backup plate 126 has been pushed deeper into anvil head 124 by knife 188, flexible arms 127a and 127b spring outwardly to a position in front of backup plate 126. In this position, arms 127a and 127b prevent cutting ring 128 and backup plate 126 from sticking to knife 188 when anvil assembly 30 is unapproximated. It is envisioned that a retainer clip may be used in conjunction with non-pivotal anvil assemblies wherein the anvil head post and the anvil center rod are integrally formed.

A second end of center rod 154 includes a bore 170 defined by a plurality of flexible arms 155. Bore 170 is dimensioned to receive a removable trocar 157. At least one of flexible arms 155, and in one embodiment, a plurality of flexible arms 155, e.g., three, include an opening 155a dimensioned to receive a projection 157d formed on removable trocar 157 to releasably secure trocar 157 to center rod 154 (FIG. 13). The distal ends of each of flexible arms 155 include an internal shoulder 155b (FIG. 10) dimensioned to releasably engage anvil retainer 38 in a manner to be discussed in detail below. A plurality of splines 181 are formed about center rod 154 and are dimensioned to be received within grooves 196a (FIG. 6) in shell assembly 31 to align anvil assembly 30 within shell assembly 31 during approximation of the anvil and shell assemblies. Center rod 154 also includes an annular recessed portion 183 to facilitate grasping of anvil assembly 30 by a surgeon with a grasper.

Referring to FIGS. 12 and 13, removable trocar 157 includes a trocar tip 157a, a body portion 157b and a cantilevered arm 157c. A projection 157d is positioned on the free end of cantilevered arm 157c. Arm 157c is deflectable downwardly, i.e., radially inwardly, in the direction indicated by arrow "A" in FIG. 13, to facilitate insertion of body portion 157b into bore 170 of center rod 154. Splines 157e or the like, are provided on body portion 157b to properly align trocar 157 within bore 170. Arm 157c biases projection 157d outwardly such that when projection 157d passes beneath opening 155a in center rod 154, projection 157d snaps outwardly into opening 155a to releasably secure removable trocar 157 to center rod 154. A tab 157f is positioned on arm 157c and can be engaged to depress arm 157c and projection 157d to remove projection 157d from an opening 155a of arm 155 to facilitate removal of trocar 157 from center rod 154. Trocar tip 157a includes a throughbore 157g dimensioned to receive a suture (not shown) to facilitate locating and removal of trocar 157 and/or anvil assembly 30 within and from the human body. Although illustrated as having a sharpened tip, other trocar tip configurations are envisioned, e.g., a blunt tip.

Shell Assembly

Figure 10F:
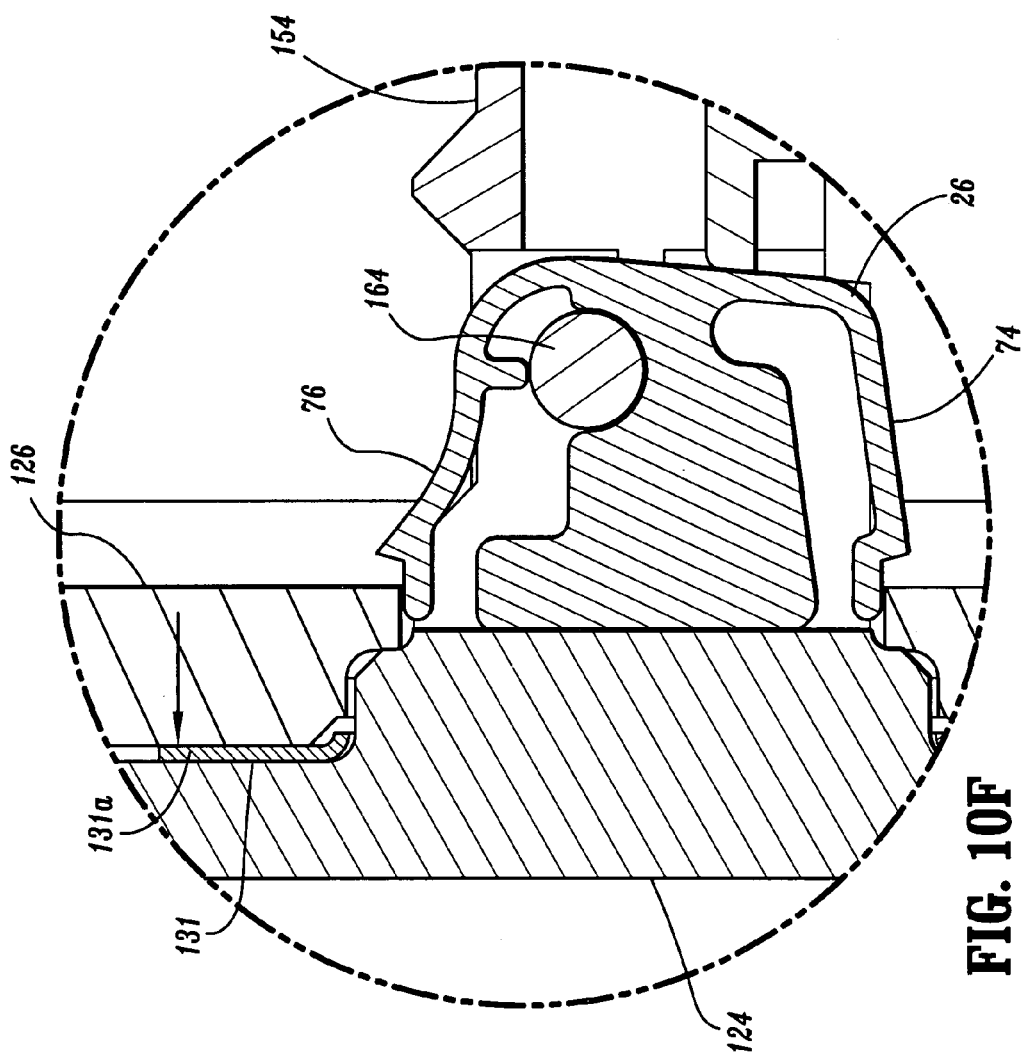
FIG. 10F is an enlarged view of the indicated area of detail shown in FIG. 10E.
Figure 10E:
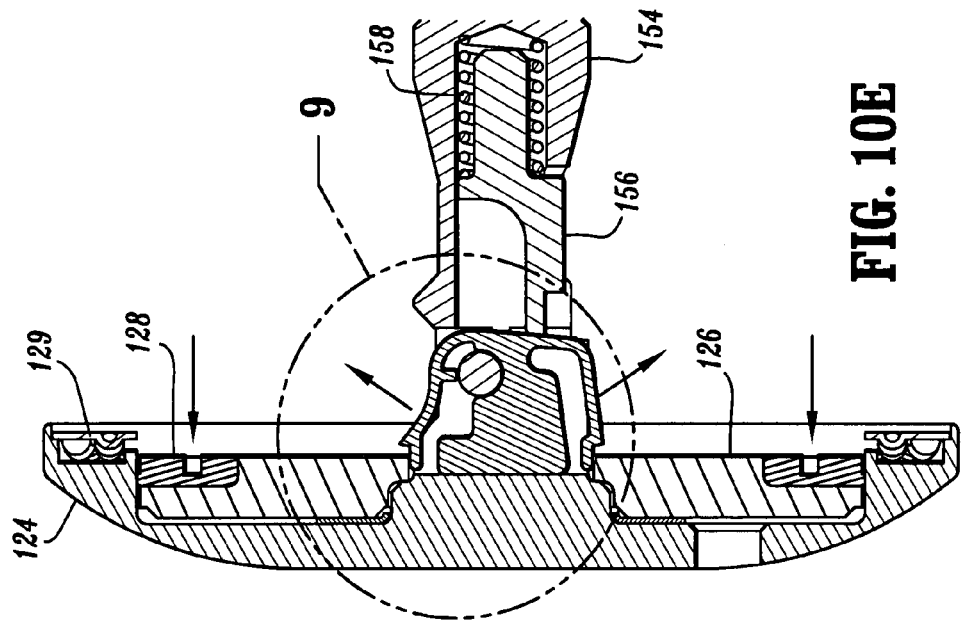
FIG. 10E is a side cross-sectional view of the anvil assembly shown in FIG. 10A with the anvil head in the operative position after deformation of the retainer member.

Referring to FIG. 6, shell assembly 31 includes a shell 182, a pusher back 186, a cylindrical knife 188, and a staple guide 192. Shell 182 includes an outer housing portion 194 and an inner guide portion 196 having grooves 196a for mating with splines 181 on anvil center rod 154 (FIG. 10). Outer housing portion 194 defines a throughbore 198 having a distal cylindrical section 200, a central conical section 202 and a proximal smaller diameter cylindrical section 204. A plurality of openings 206 are formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 207a formed on the distal end of outer tube 14a to secure shell 182 to elongated body 14. A pair of openings 211 formed in the proximal end of outer tube 14a are dimensioned to receive protrusions (not shown) formed on the internal wall of stationary handle 18 to facilitate attachment of tube 14a to handle portion 12.

Pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 includes a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and eject staples 230 from staple guide 192 into staple deforming pockets 140 of anvil 129. Since knife 188 is secured to pusher back 186, knife 188 is also advanced distally to core tissue as will be described in more detail below.

Figure 14:
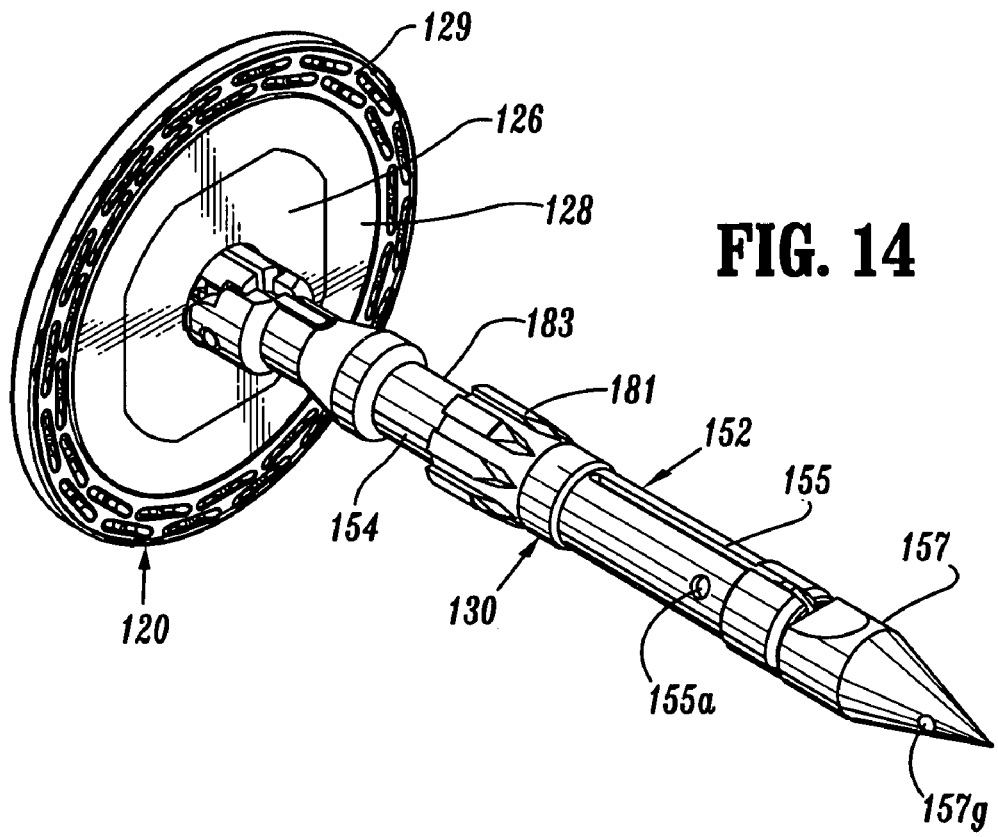
FIG. 14 is a side perspective view from the proximal end of the anvil assembly shown in FIG. 10 with the removable trocar attached thereto.
Figure 15:
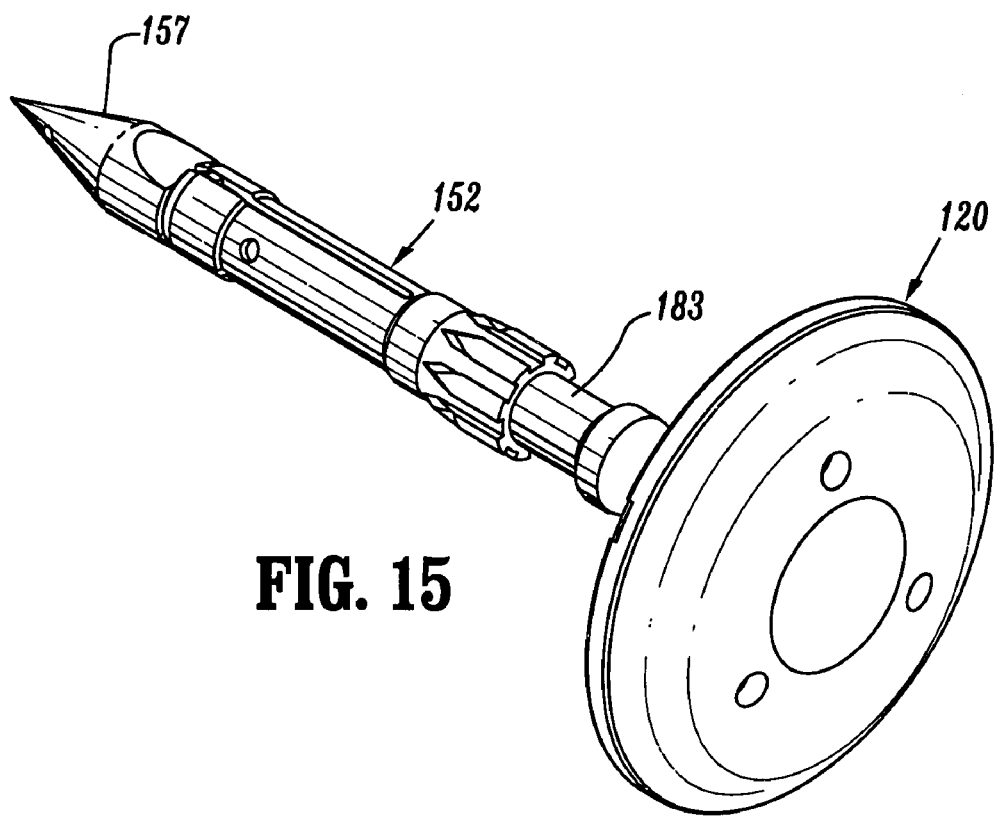
FIG. 15 is a side perspective view from the distal end of the anvil assembly shown in FIG. 14.
Figure 21:
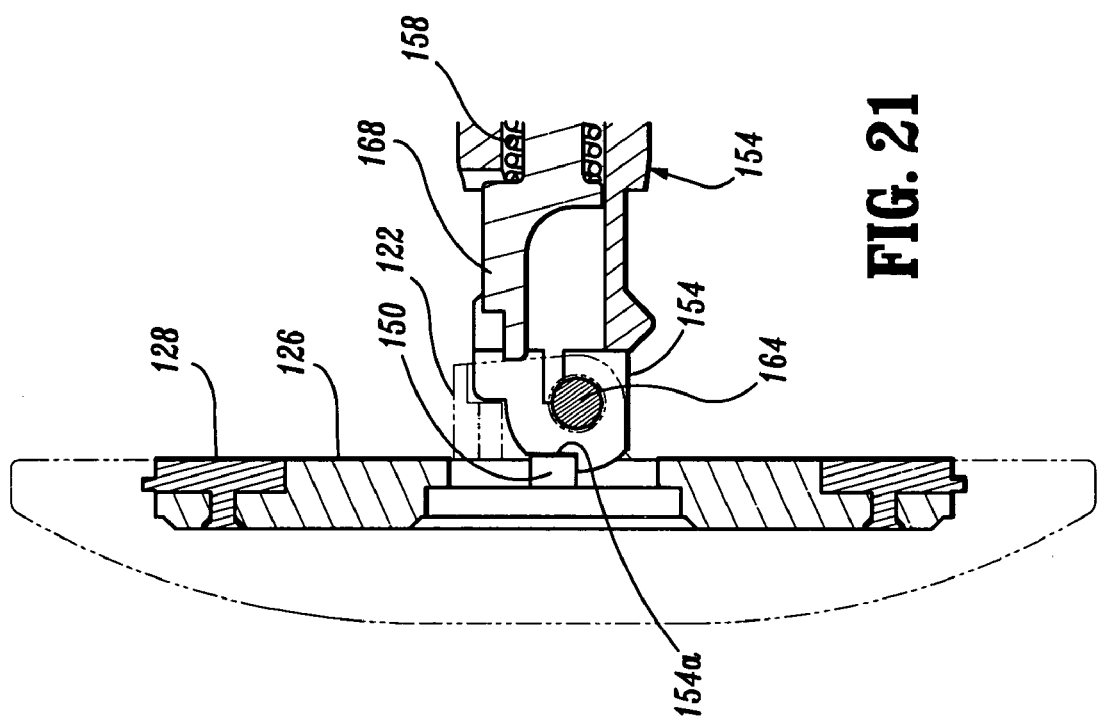
FIG. 21 is a side cross-sectional partial cutaway view of the distal portion of the anvil assembly shown in FIG. 19, with the anvil head shown in phantom.
Figure 20:
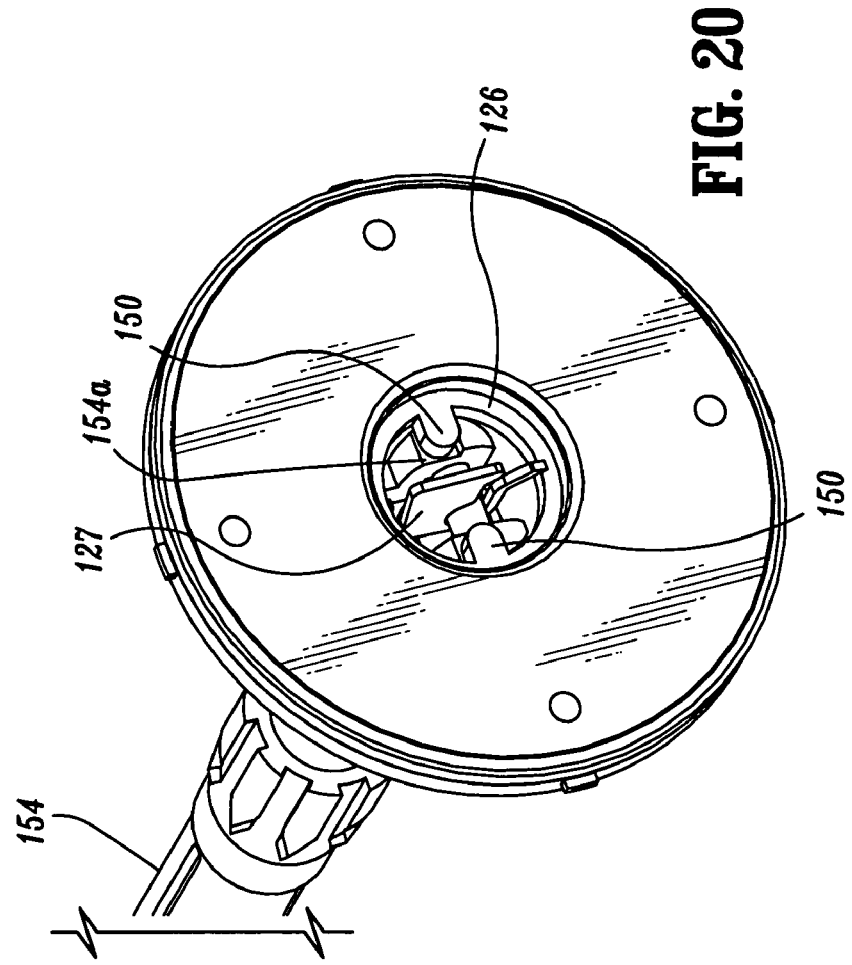
FIG. 20 is a perspective, partial cutaway view from the distal end of the anvil assembly shown in FIG. 19, with the anvil head removed.
Figure 22:
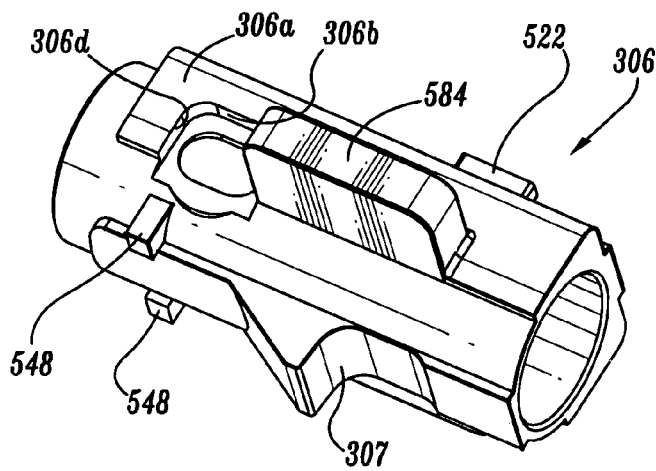
FIG. 22 is a side perspective view from the bottom of the screw stop of the handle assembly shown in FIG. 3.

A rigid bushing 209 is supported in the proximal end of inner guide portion 196 of shell 182. Bushing 209 defines a throughbore dimensioned to slidably receive anvil retainer 38 and center rod 154 of anvil assembly 30 (FIG. 14). Bushing 209 provides lateral support for flexible arms 155 of center rod 154 when the anvil assembly 30 has been approximated to prevent disengagement of anvil assembly 30 from anvil retainer 38. In the unapproximated position, flexible arms 155 of center rod 154 are positioned externally of bushing 209 to permit removal of anvil assembly 30 from retainer 38.

Cam Adjustment Mechanism

Referring to FIGS. 8 and 22-28, a cam adjustment member 400 is secured by set screw 312 onto a sidewall 306*a* of screw stop 306 within a recess 306*b* formed in sidewall 306*a*. Cam adjustment member 400 includes a circular disc 402 having a throughbore 404. Throughbore 404 is eccentrically formed through disc 402 and is dimensioned to receive set screw 312. A smaller notch or hole 406 is also formed in disc 402 and is dimensioned to receive the tip of an adjustment tool (not shown). Recess 306*b* (FIG. 22) includes a forward abutment shoulder or surface 306*c* and a rear abutment surface 306*d* and is dimensioned to receive disc 402 such that the outer edge of disc 402 abuts forward and rear abutment surfaces 306*c* and 306*d*.

Set screw 312 extends through disc 402 and screw stop 306 and is received in a threaded bore 32*a* (FIG. 6) in screw 32 to secure screw stop 306 in an axially fixed position on screw 32. Cam adjustment member 400 functions to adjust the axial position of screw stop 306 on screw 32. More specifically, set screw 312 can be loosened to allow disc 402 to rotate within recess 306*b* of screw stop 306. Since disc 402 is eccentrically mounted about screw 32 and engages forward and rear abutment surfaces 306*c* and 306*d* of recess 306*b*, rotation of disc 402 about fixed set screw 312 will urge screw stop 306 axially along screw 32 to adjust the axial position of screw stop 306 on screw 32. For example, when disc 402 is rotated in a clockwise direction (as viewed in FIG. 28) as indicated by arrow "B", screw stop 306 will be moved axially in relation to screw 32 in the direction indicated by arrow "C" in response to engagement between the outer edge of disc 402 and rear shoulder 306*d* of recess 306*b*. Conversely, when disc 402 is rotated in a counter-clockwise direction (as viewed in FIG. 27), as indicated by arrow "D", screw stop 306 will be moved axially in relation to screw 32 in the direction indicated by arrow "E" in response to engagement between the outer edge of disc 402 and forward shoulder 306*c* of recess 306*b*.

When stapling device 10 is in a fully approximated position, i.e., anvil assembly 30 and shell assembly 31 are brought into juxtaposed alignment to define a tissue receiving clearance (FIG. 46), screw stop 306 abuts against body portion 42 of the rotatable sleeve 33, i.e., sleeve 33 functions as a proximal stop for the approximation mechanism. See FIG. 48. In this position, anvil assembly 30 and shell assembly 31 are spaced slightly to define a tissue receiving clearance. By providing cam adjustment member 400, the tissue receiving clearance can be selectively adjusted to be within a desired range by adjusting the position of screw stop 306 on screw 32. In one embodiment, cam adjustment member 400 permits adjustment of the tissue receiving clearance of ±0.045 inches, although greater or lesser adjustment capabilities are also envisioned. Typically, adjustments to the tissue receiving clearance will be made by the device manufacturer. Alternately, a hole or opening may be provided in handle portion 12 (FIG. 1) to provide direct access to adjustment member 400 to allow for on-site adjustment of the tissue receiving clearance by a surgeon or other medical professional.

Indicator Mechanism

Figure 32:
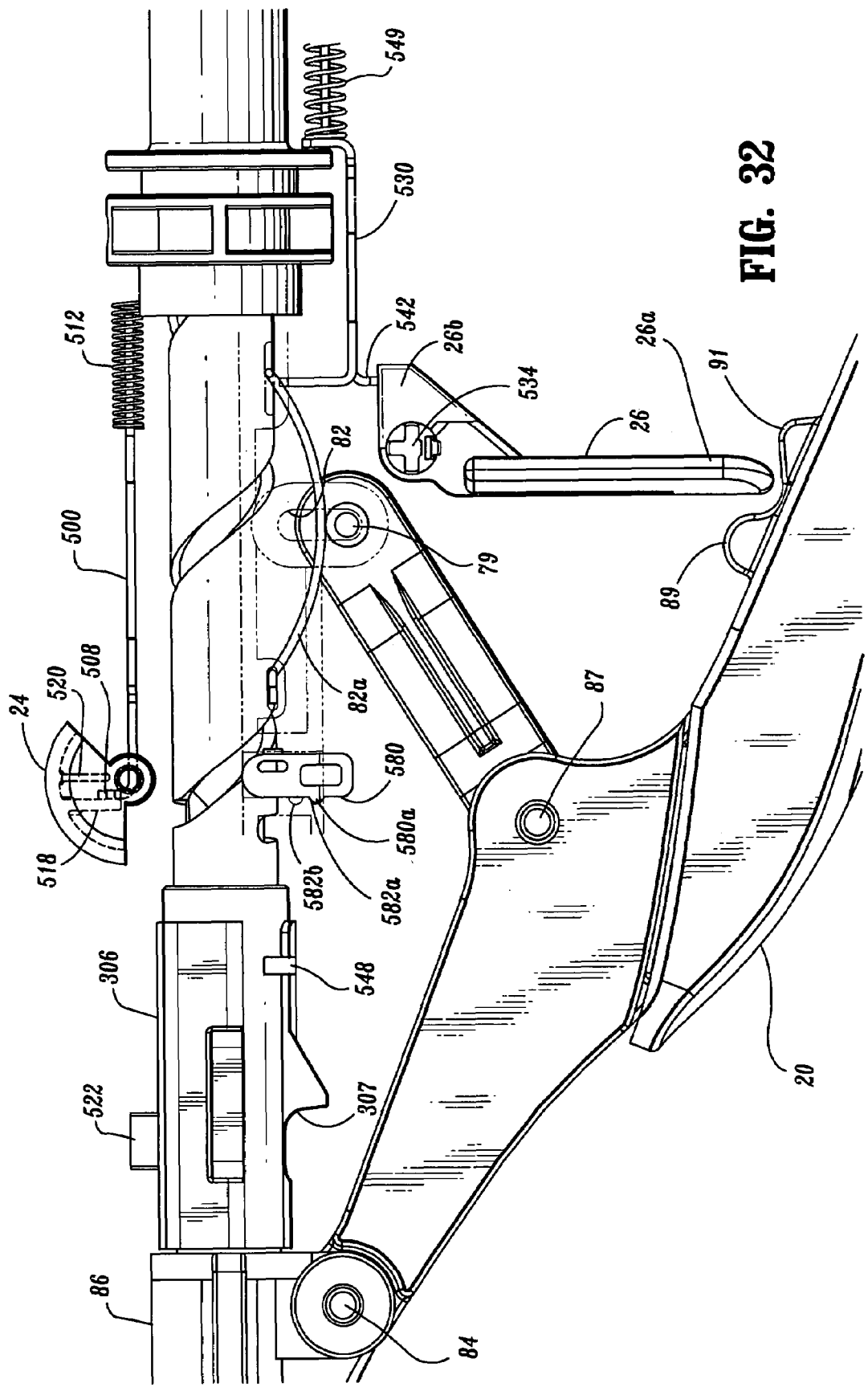
FIG. 32 is a side enlarged view of the handle assembly of the surgical stapling device shown in FIG. 31 with the handle sections removed.

Referring to FIGS. 3-5 and 29, the indicator mechanism includes bulbous indicator 24, lens cover 24*a* and slide member 500. Indicator 24 is pivotally supported about a pivot member 502 which can be formed monolithically with handle sections 18*a* and 18*b*. Lens cover 24*a* is positioned above indicator 24 and, in one embodiment, is formed of magnification material to facilitate easy visualization of indicator 24. Slide member 500 includes a body portion 504 having an elongated slot 506 formed therein, a distal abutment member or upturned lip portion 508, and a proximal extension 510. Slide member 500 is slidably positioned between handle sections 18*a* and 18*b*. Proximal extension 510 is slidably supported within stationary handle 18 by support structure 516 (FIG. 5) which may be integrally formed with handle sections 18*a* and 18*b*. A biasing member, e.g., a coil spring 512, is positioned in compression about proximal extension 510 between support structure 516 and body portion 504 of slide member 500 to urge slide member 500 distally within stationary handle 18. Indicator 24 includes a pair of downwardly extending projections 518 and 520 (FIG. 32). Upturned lip portion 508 of slide member 500 is positioned between projections 518 and 520 and is positioned to engage projections 518 and 520 as it moves within stationary handle 18. In the unfired position of device 10, biasing member 512 urges slide member 500 distally to move lip portion 508 into engagement with projection 518 to pivot indicator 24 to a first position, which provides indication to a surgeon that the device has not been approximated and is not in a fire-ready condition.

Figure 33:
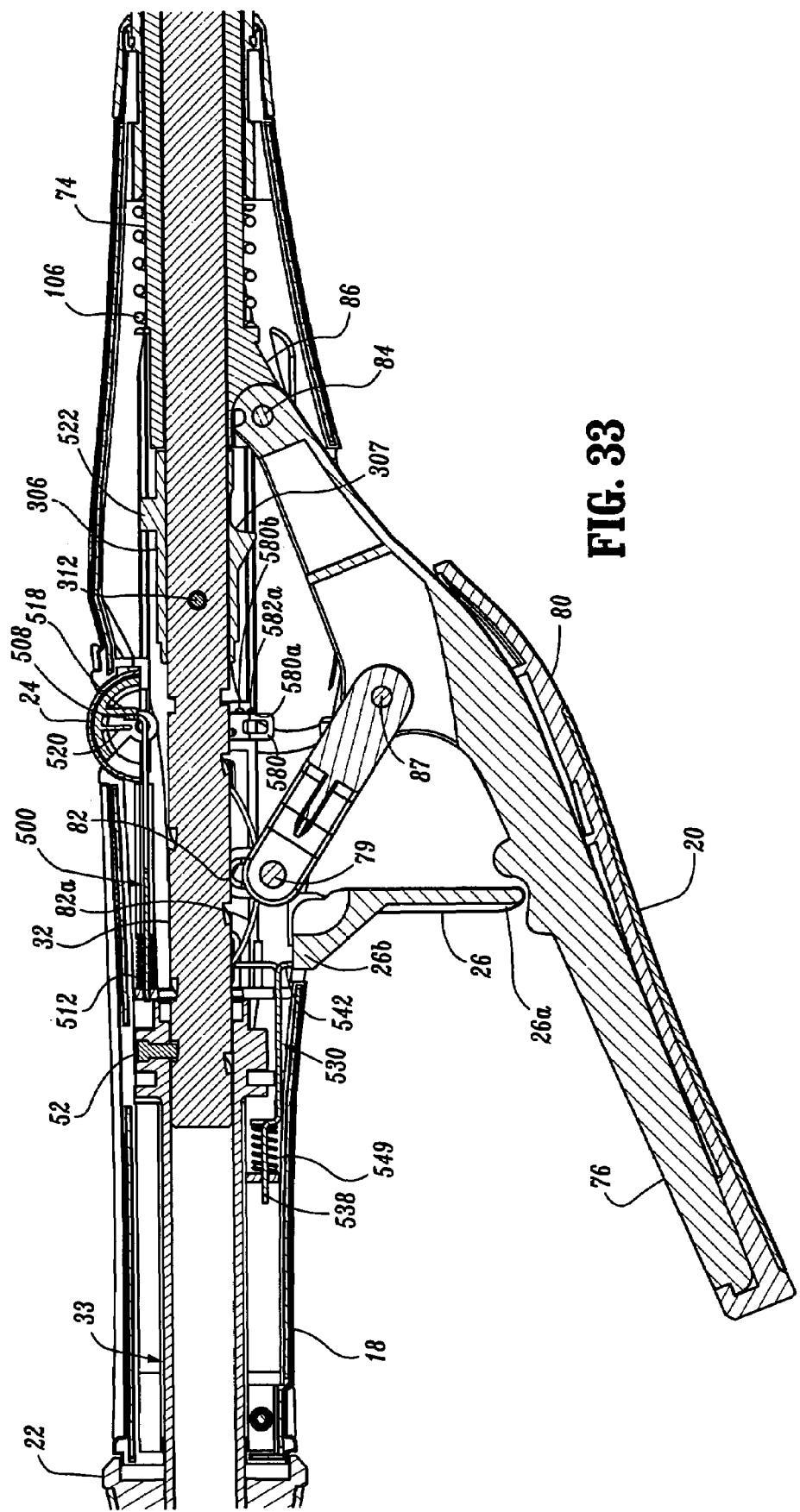
FIG. 33 is an enlarged view of the indicated area of detail shown in FIG. 31.
Figure 34:
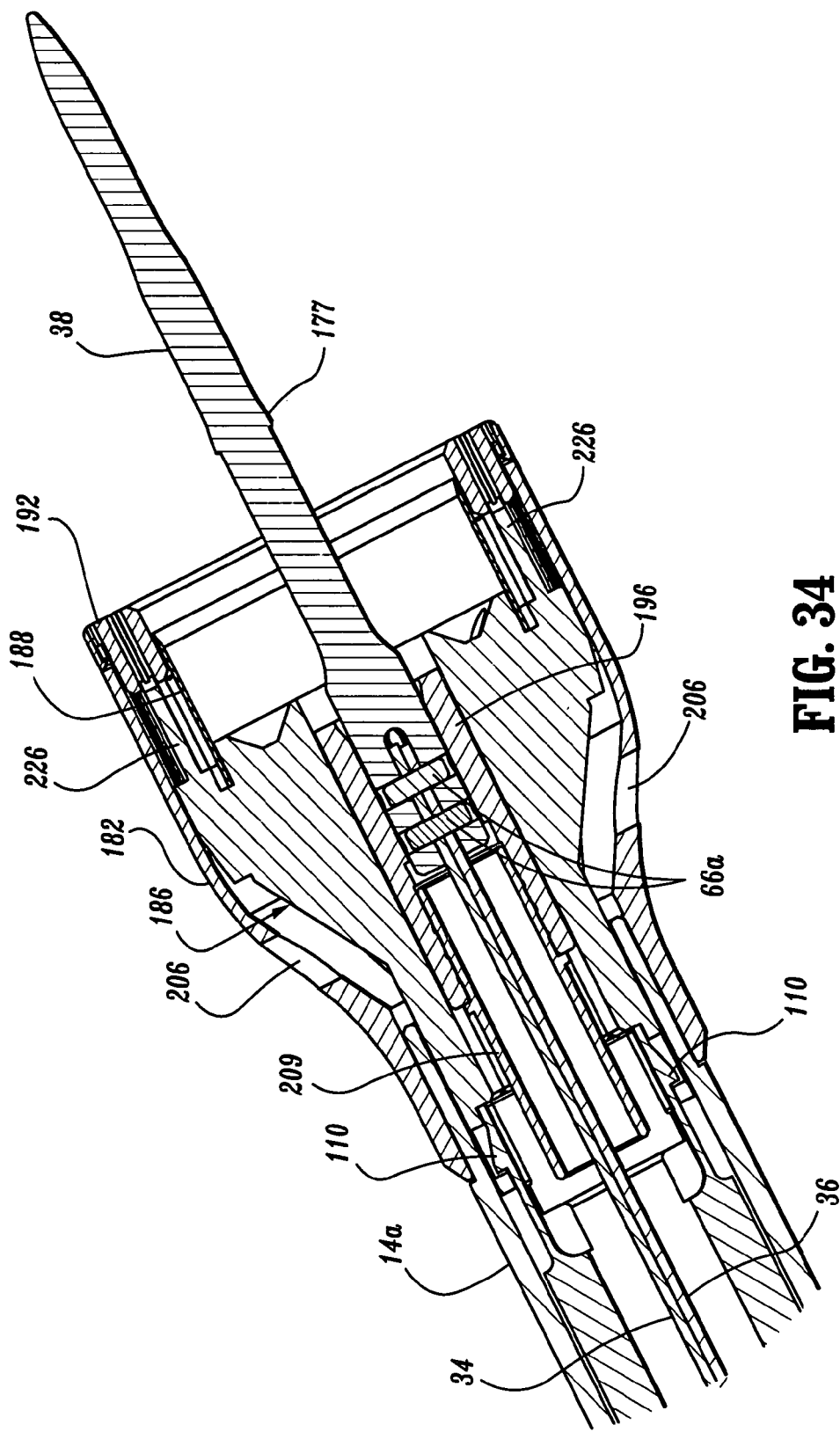
FIG. 34 is an enlarged view of the indicated area of detail shown in FIG. 31.
Figure 35:
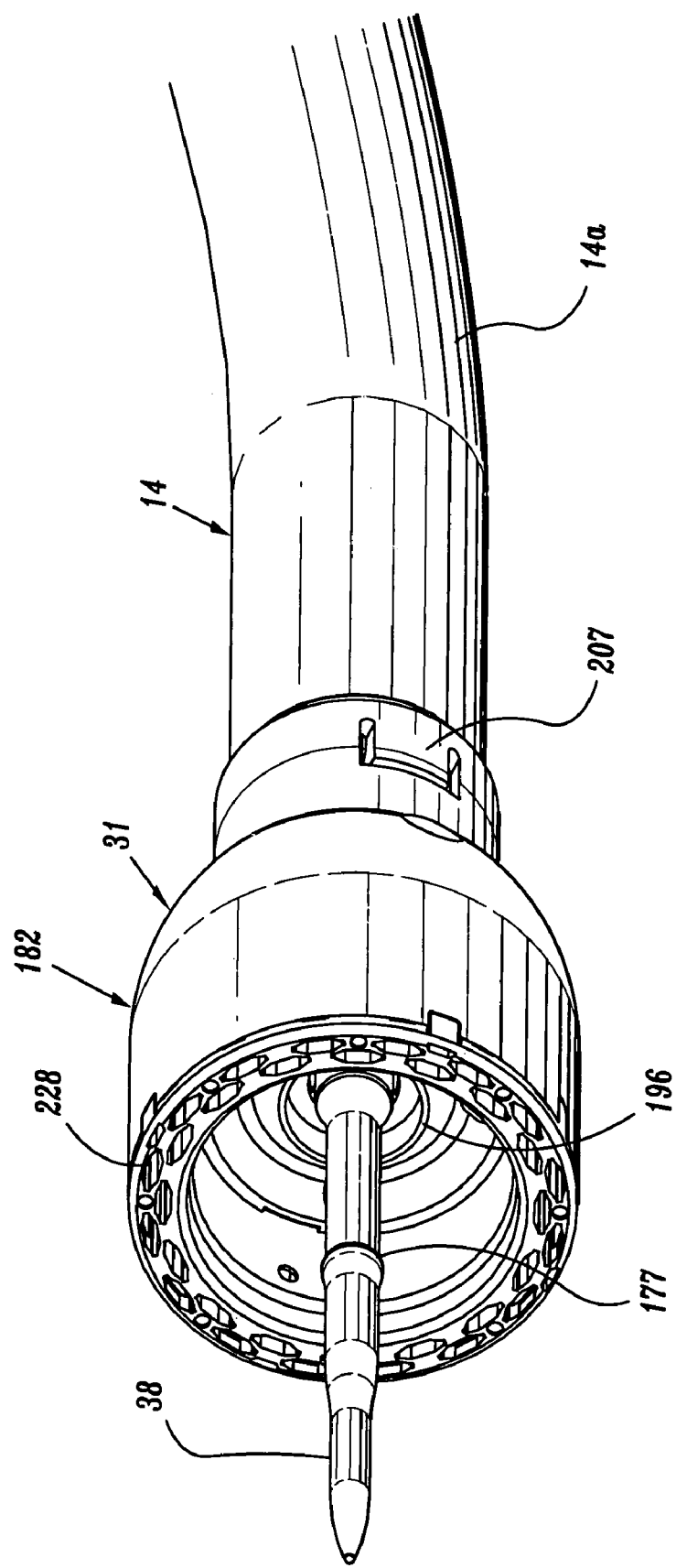
FIG. 35 is a perspective view from the front of the distal end of the surgical stapling device shown in FIG. 31 with the anvil assembly removed.

As discussed above, screw stop 306 is fixedly attached to screw 32 (FIG. 33). Screw stop 306 includes a first abutment or engagement member 522 which is positioned to travel through slot 506 of slide member 500 and engage the proximal end 506*a* (FIG. 29) of slot 506 during approximation of the device. When engagement member 522 abuts proximal end 506*a* of slot 506, further approximation of device 10 moves slide plate 500 proximally within stationary handle 18 against the bias of spring 512 such that upturned lip 508 of slide member 500 engages projection 520 of indicator 24. Engagement between projection 520 and lip 508 causes indicator 24 to pivot about pivot member 502 to a second position. In the second position, indicator 24 provides indication to a surgeon that the device has been approximated and is now in a fire-ready position. See FIG. 48.

Fire-Lockout Mechanism

Referring to FIGS. 3-5, and 30, the firing-lockout mechanism includes trigger lock 26 and a lockout member 530. Trigger lock 26 is pivotally supported within bores 532 (FIG. 3) in handle sections 18*a* and 18*b* about pivot member 534. In one embodiment, pivot member 534 is T-shaped and frictionally engages the inner wall of bores 532 to prevent free rotation of trigger lock 26. Alternately, other pivot member configurations are envisioned, e.g., circular, square, etc. Tip 26*a* of trigger lock 26 is positioned between abutments 89 and 91 on body portion 76 of firing trigger 20 to prevent actuation of trigger 20 when trigger lock 26 is in the locked position. Trigger lock 26 also includes a proximal extension 26*b* which will be discussed in further detail below.

In an alternate embodiment shown in FIG. 3B, a boot 26'*c* is secured to the end of trigger lock 26' for positioning between abutments 89 and 91. Boot 26'*c* may be formed integrally with trigger lock 26', or may be formed separately of an appropriate material such as rubber or plastic and overmolded or otherwise attached to trigger lock 26'. Boot 26'*c* frictionally retains firing lock 26' between abutments 89 and 91 to prevent trigger lock 26 from rattling back and forth between abutments 89 and 91. Trigger lock 26 also includes a proximal extension 26*b* which will be discussed in further detail below.

Lockout member 530 includes a body portion 536, a proximal extension 538, a pair of front legs 540a, a pair of rear legs 540b, and an abutment member or downturned lip portion 542. Lockout member 530 is slidably positioned between first and second stops 544 and 546 (FIG. 5) formed on an internal wall of handle sections 18a and 18b. Stop 544 is positioned to engage extension 538 rear legs 540b and stop 546 is positioned to engage front legs 540a. It is also envisioned that a single abutment member may be substituted for each pair of legs. A biasing member 549, e.g, a coil spring, is positioned between stop 544 and rear legs 540b of body 536 about proximal extension 538 to urge lockout 530 to its distal-most position with legs 540 abutting stop 546. In this position, extension 26b of trigger lock 26 is positioned beneath lip portion 542 of lockout member 530 to prevent pivotal movement of trigger lock 26 about pivot member 534, and thus, prevent firing of stapling device 10.

Figure 23:
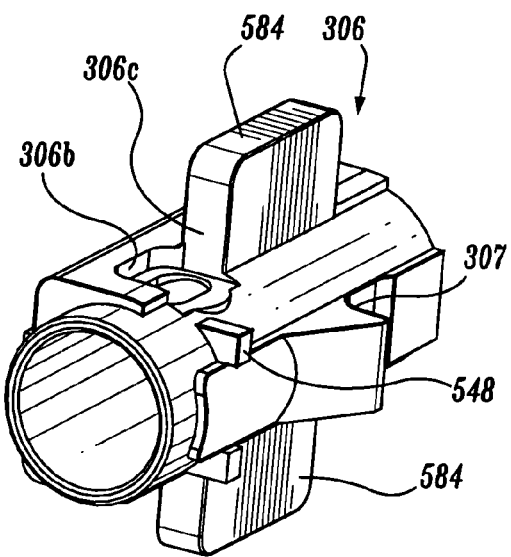
FIG. 23 is a bottom perspective view from the proximal end of the screw stop shown in FIG. 22.
Figure 24:
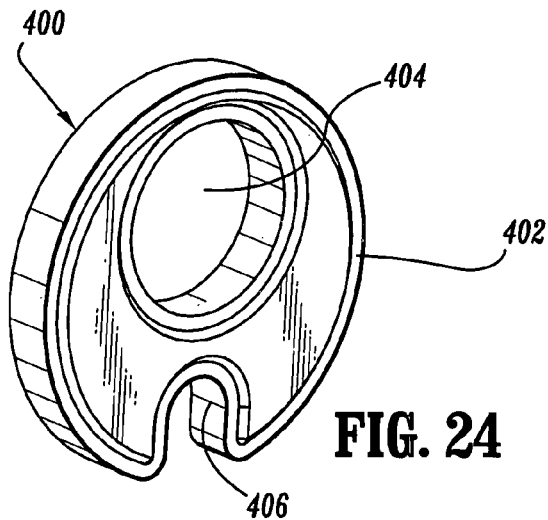
FIG. 24 is a top perspective view of the cam adjustment member of the handle assembly shown in FIG. 3.
Figure 25:
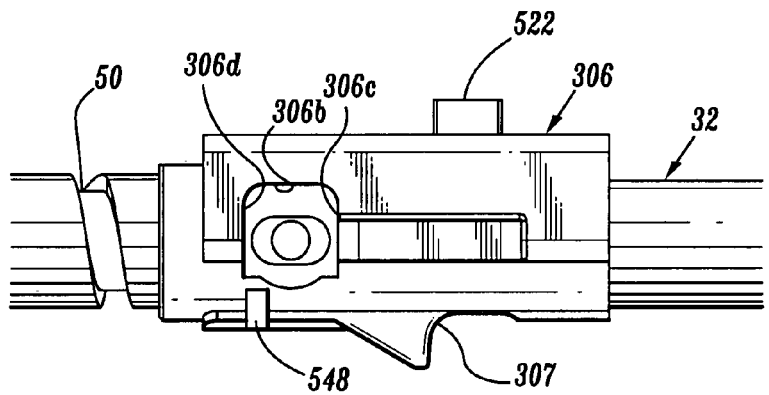
FIG. 25 is a side view of the screw and screw stop of the handle assembly shown in FIG. 3 with the set screw and the cam adjustment member removed.
Figure 26:
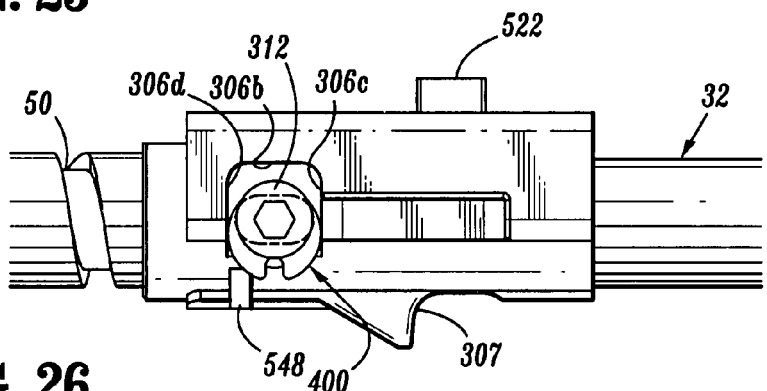
FIG. 26 is a side view of the screw and screw stop shown in FIG. 25 with the set screw and cam adjustment member attached thereto.
Figure 27:
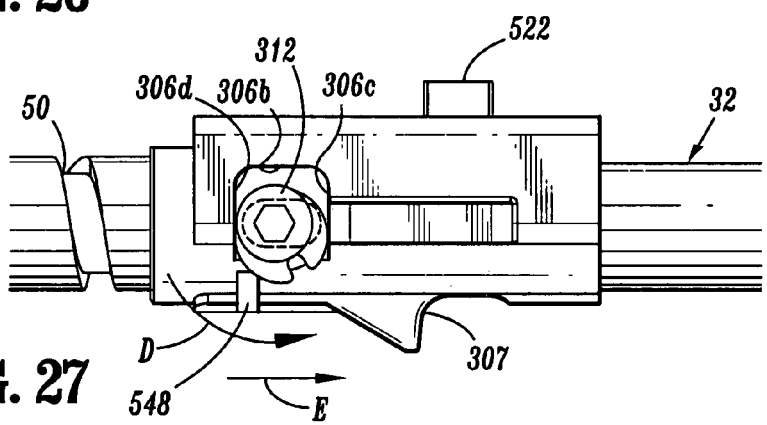
FIG. 27 is a side view of the screw and screw stop shown in FIG. 26 with the cam adjustment screw adjusted to increase the tissue gap.
Figure 28:
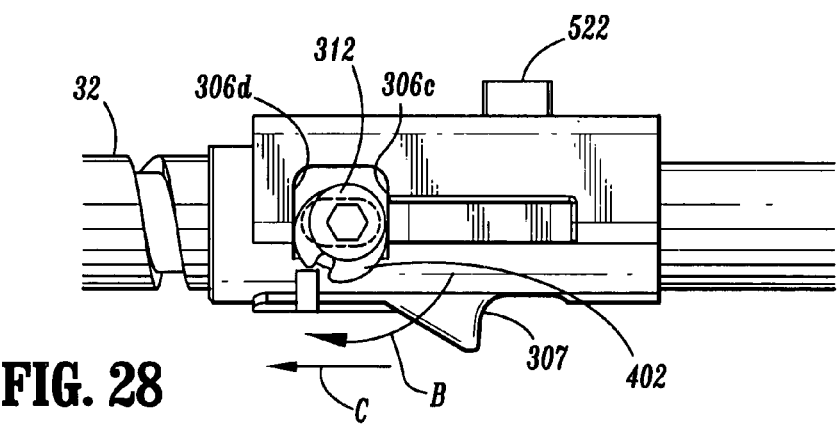
FIG. 28 is a side view of the screw and screw stop shown in FIG. 26 with the cam adjustment screw adjusted to decrease the tissue gap.
Figure 29:
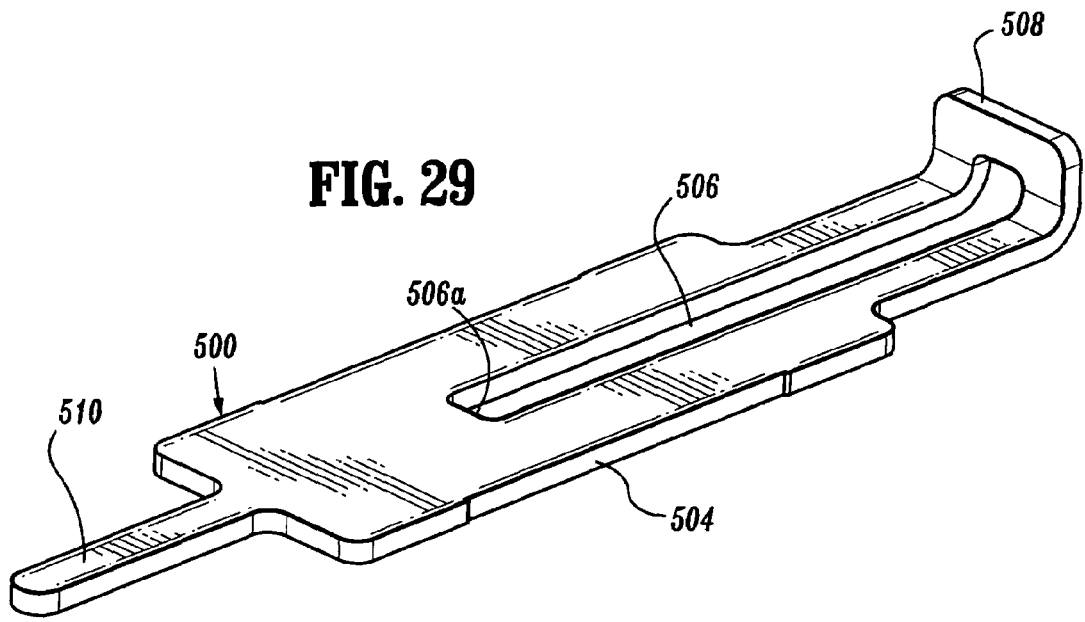
FIG. 29 is a top perspective view from the proximal end of the slide member of the indicator mechanism of the handle assembly shown in FIG. 3.
Figure 30:
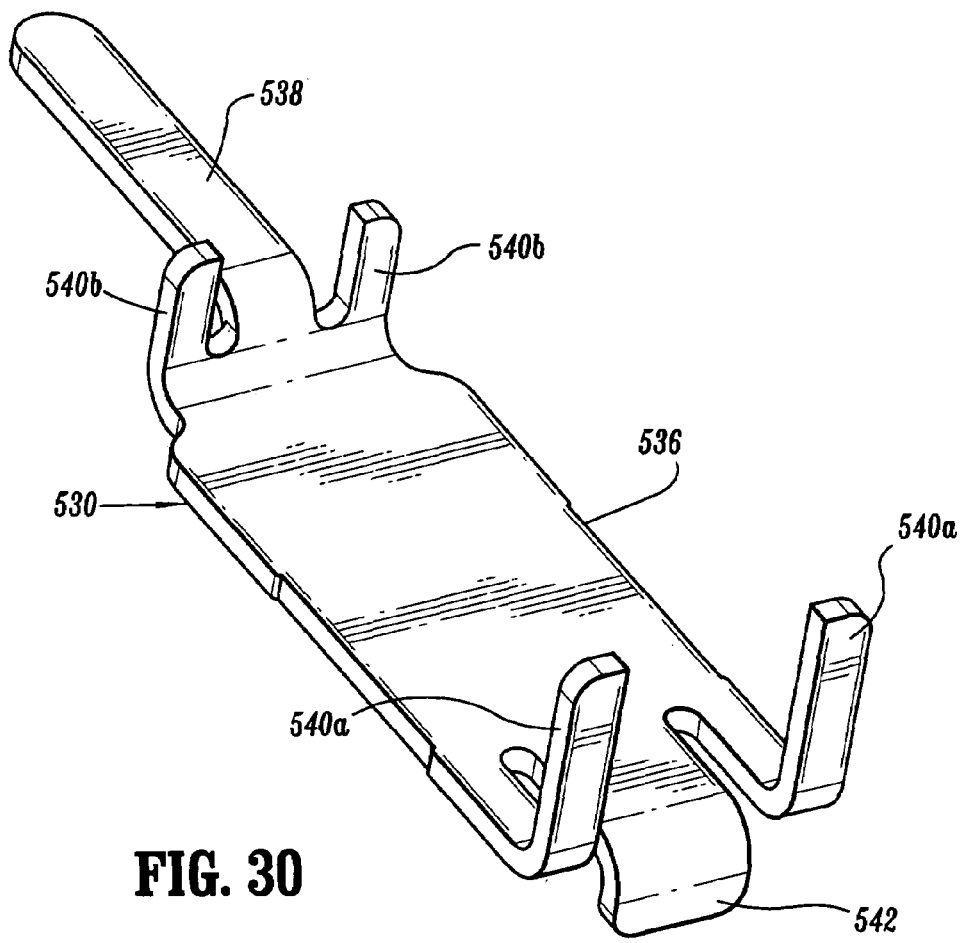
FIG. 30 is a bottom perspective view of the lockout member of the fire lockout mechanism of the handle assembly shown in FIG. 3.
Figure 31:
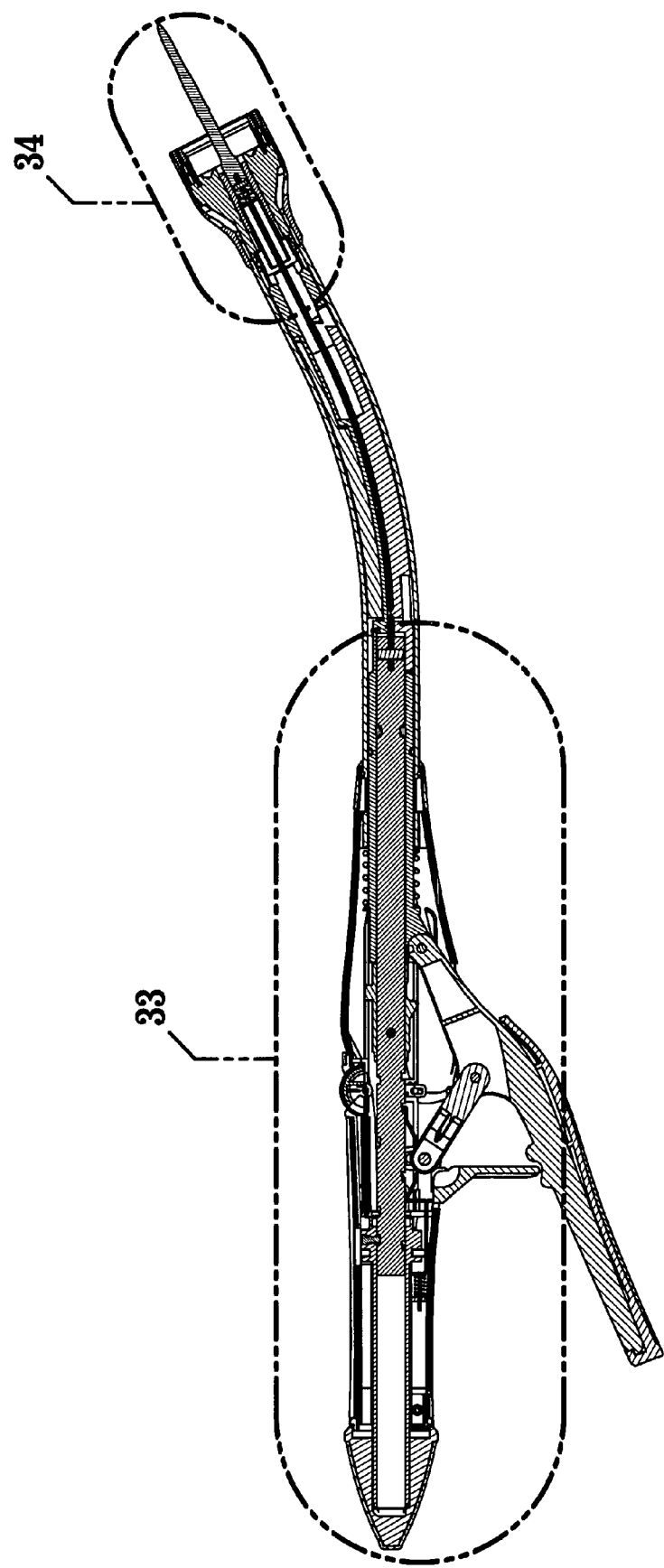
FIG. 31 is a side cross-sectional view of the surgical stapling device shown in FIG. 1 with the anvil assembly removed.

As discussed above, screw stop 306 is secured to screw 32. A second engagement member or members 548 extend downwardly from screw stop 306 (FIG. 23). When stapling device 10 is approximated and screw 32 is moved proximally within stationary handle 18, engagement member 548 abuts distal legs 540a (FIG. 47) of lockout member 530 to move lockout member 530 proximally against the bias of spring member 549 to a position in which lip portion 542 is spaced proximally of extension 26b of trigger lock 26. In this position of lockout member 530, trigger lock 526 can be pivoted about pivot member 534 to permit firing of stapling device 10.

Tactile Indicator Mechanism

Referring to FIGS. 3, 5, 9 and 9A, a tactile indicator mechanism provided in stationary handle 18 includes an abutment member 580 which is slidably positioned in a vertical slot 582 defined within handle sections 18a and 18b. Abutment member 580 includes a protuberance 580a and a guide rib 580b. Protuberance 580a is dimensioned to be received within one of two detents or recesses 582a and 582b formed along a wall of slot 582. Abutment member 580 is movable from a retracted (downward) position, wherein protuberance 580a is positioned within detent 582a, to an extended (upward) position, wherein protuberance 580a is positioned within detent 582b. Engagement between protuberance 580a and detents 582a and 582b retains abutment member 580 in its respective upward or downward position.

Prior to firing of stapling device 10, abutment member 580 is located in the retracted (downward) position. When device 10 is fired, an extension 590 (FIG. 3) of firing link 72 engages abutment member 580 and moves abutment member 580 from its retracted to its extended position. In the extended position, abutment member 580 extends into channel 111 of stationary handle 18.

Screw stop 306 includes a pair of wings 584 which are slidably positioned in channel 111 of stationary handle 18. After stapling device 10 has been fired, abutment member 580 is positioned within channel 111. During unapproximation of anvil assembly 30 and cartridge assembly 31, a wing 584 of screw stop 306 will engage abutment member 580 and urge abutment member 580 back to its retracted (downward) position. Engagement between abutment member 580 and wing 584 of screw stop 306 provides a tactile and/or an audible indication to the surgeon that the anvil and cartridge assemblies 30 and 31 have been unapproximated a predetermined amount. In one embodiment, abutment member 580 is positioned to engage wing 584 of screw stop 306 at the point when the anvil and cartridge assemblies have been separated a distance sufficient to allow the anvil head assembly to tilt. This can occur when approximation knob 22 has been turned from about two to about two and a half rotations. Thus, engagement between abutment member 580 and wing 584 of screw stop 306 provides a tactile and/or audible indication to the surgeon that the anvil head assembly 120 has tilted and stapling device 10 can be removed from a patient.

Operation

Operation of surgical stapling device 10 will now be described in detail with reference to FIGS. 31-61.

FIGS. 31-35 illustrate surgical stapling device 10 in the unapproximated or open position prior to attachment of anvil assembly 30 to anvil retainer 38. In this position, biasing member 106 (FIG. 33) is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction, as viewed in FIG. 33. Biasing member 549 is engaged with body 536 of lockout member 530 to urge lockout member 530 to its distal-most position, wherein lip portion 542 of lockout member 530 is positioned above extension 26b of trigger lock 26 to prevent movement of trigger lock 26 to the unlocked position. Biasing member 82a is also engaged with pivot member 79 (FIG. 32) to urge pivot member 79 to the base of vertical slot 82 and tactile indicator 580 is in the retracted or downward position with protrusion 580a positioned with detent 582a.

Figure 38:
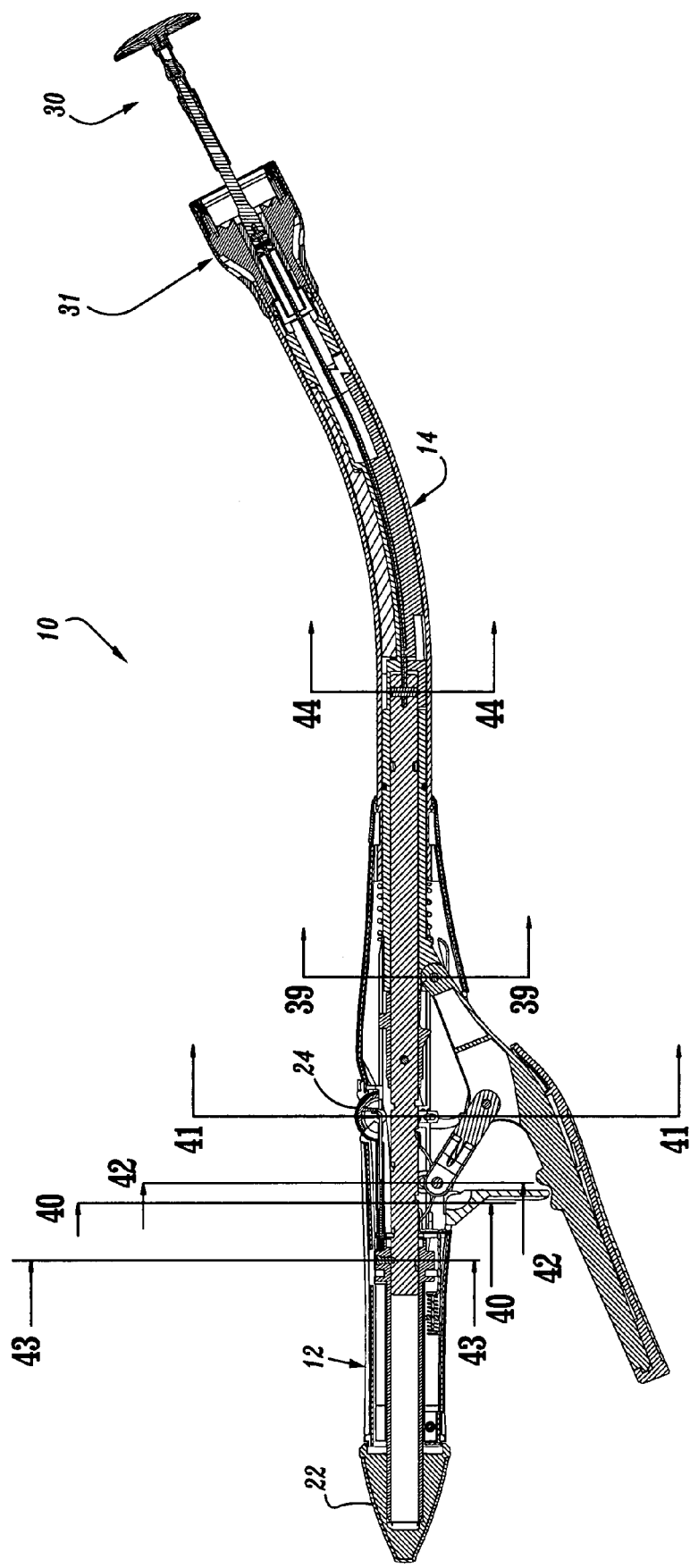
FIG. 38 is a side cross-sectional view of the surgical stapling device shown in FIG. 31 with the anvil assembly attached thereto.
Figure 45:
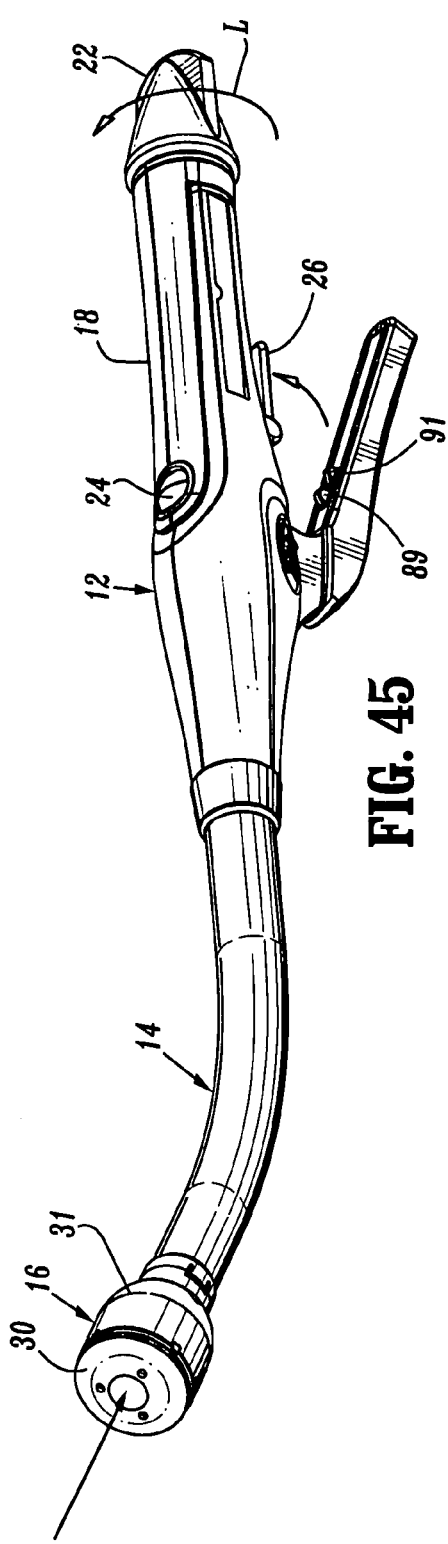
FIG. 45 is a side perspective view of the surgical stapling device shown in FIG. 38 with the anvil assembly in an approximated position.

FIGS. 36-44 illustrate surgical stapling device 10 with anvil assembly 30 attached to anvil retainer 38 and anvil assembly 30 in the unapproximated or open position in relation to shell assembly 31. Referring to FIGS. 37 and 38, during attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K" in FIG. 37 until internal shoulder 155b of flexible arms 155 passes over annular protrusion 177 formed on a central portion of anvil retainer 38. At this point, resilient legs 155 releasably engage the anvil retainer. The position of the remaining components of stapling device are not affected by attachment of anvil assembly 30 to anvil retainer 38 and remain as described above and shown in FIGS. 31-35.

Figure 46:
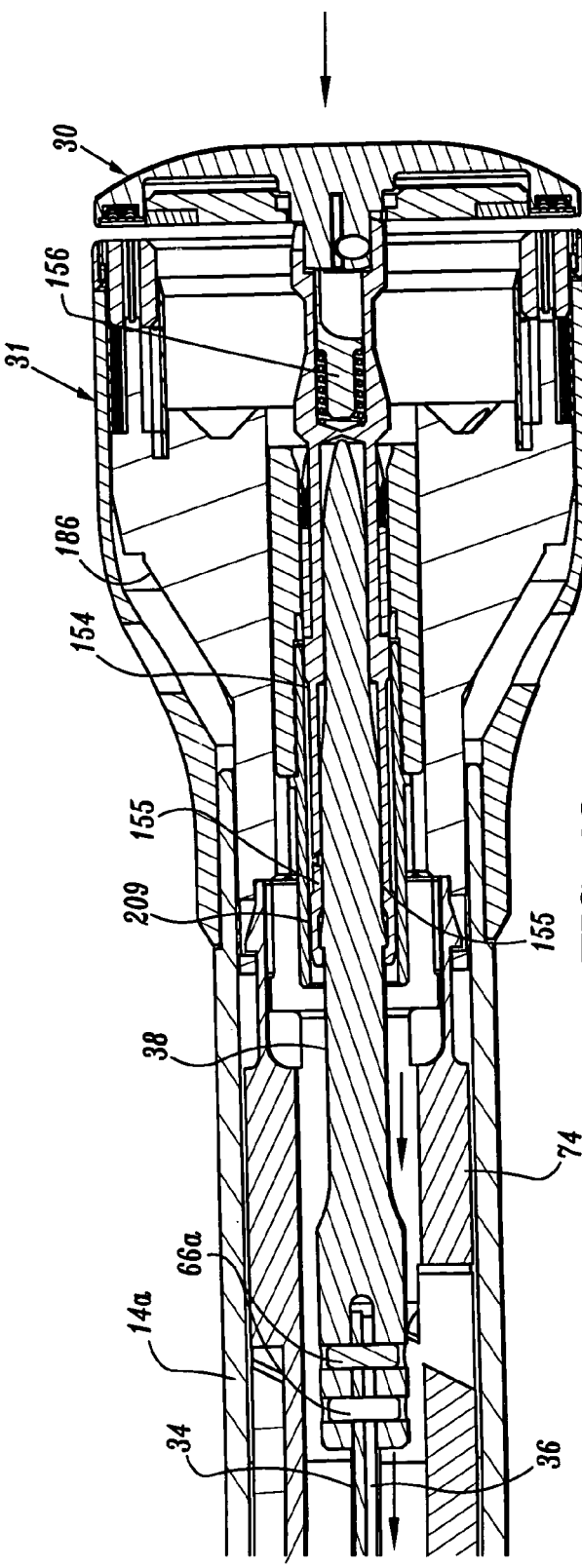
FIG. 46 is a side cross-sectional view of the distal end of the surgical stapling device shown in FIG. 45.

FIGS. 45-50 illustrate surgical stapling device 10 during movement of anvil assembly 30 and cartridge assembly 31 to the approximated or closed position. As discussed above, anvil assembly 30 is moved to the approximated or closed position by rotating rotation knob 22 in the direction indicated by arrow "L" in FIG. 45. Rotation of knob 22 causes cylindrical sleeve 33 to rotate to move pin 52 along helical channel 50 of screw 32. See FIG. 48. Movement of pin 52 along helical channel 50 causes screw 32 to translate proximally within sleeve 33. The distal end of screw 32 is connected to screw extensions 34 and 36 which are fastened at their distal ends to anvil retainer 38 (FIG. 46). As such, retraction of screw 32 within sleeve 33 is translated into proximal movement of anvil retainer 38 and anvil assembly 30. It is noted that when anvil assembly 30 is approximated, flexible legs 155 of center rod 154 are drawn into bushing 209 to lock legs 155 onto anvil retainer 38.

Figure 47:
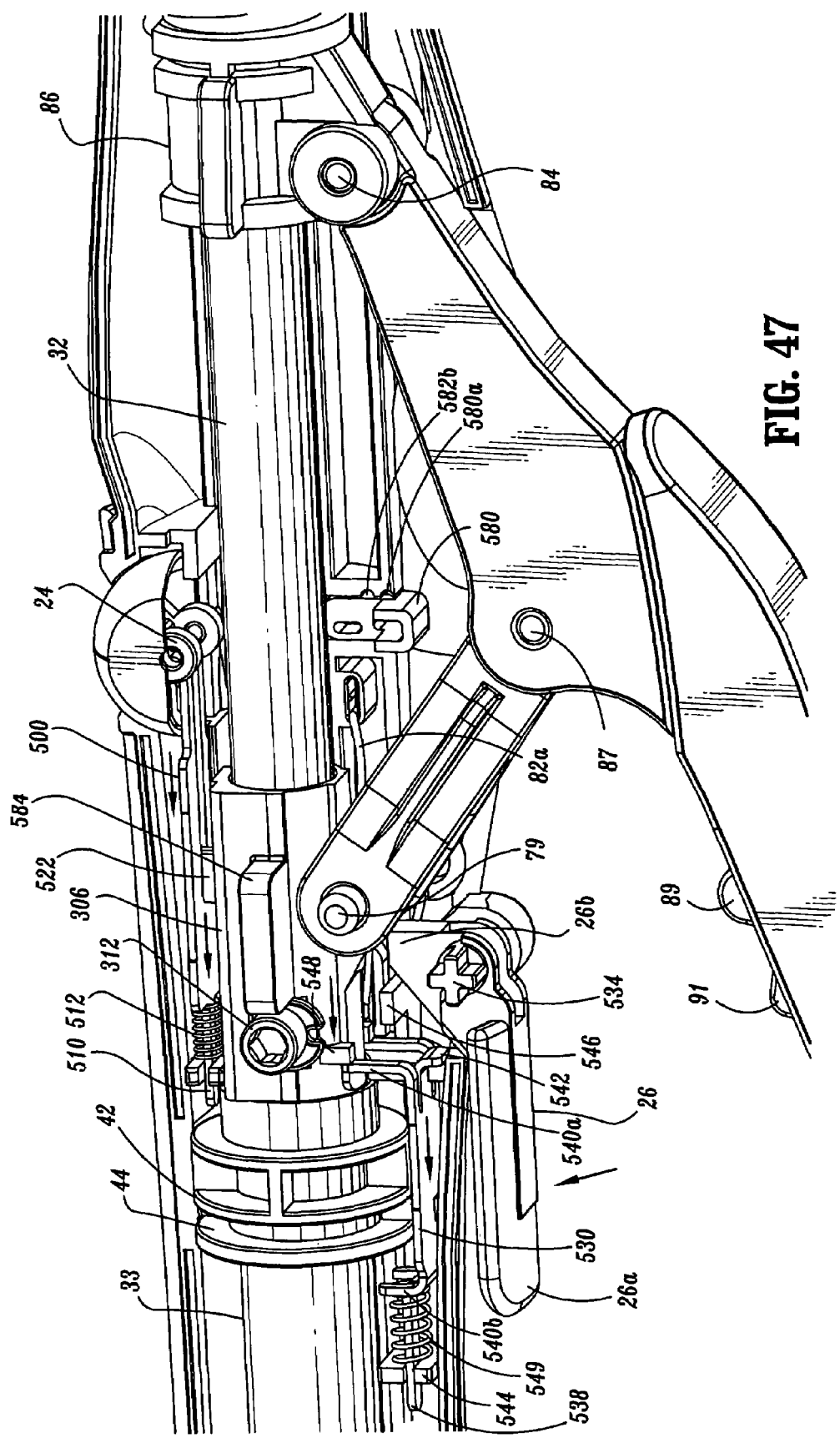
FIG. 47 is a side enlarged view of the handle assembly of the surgical stapling device shown in FIG. 45 with a handle section removed.
Figure 50:
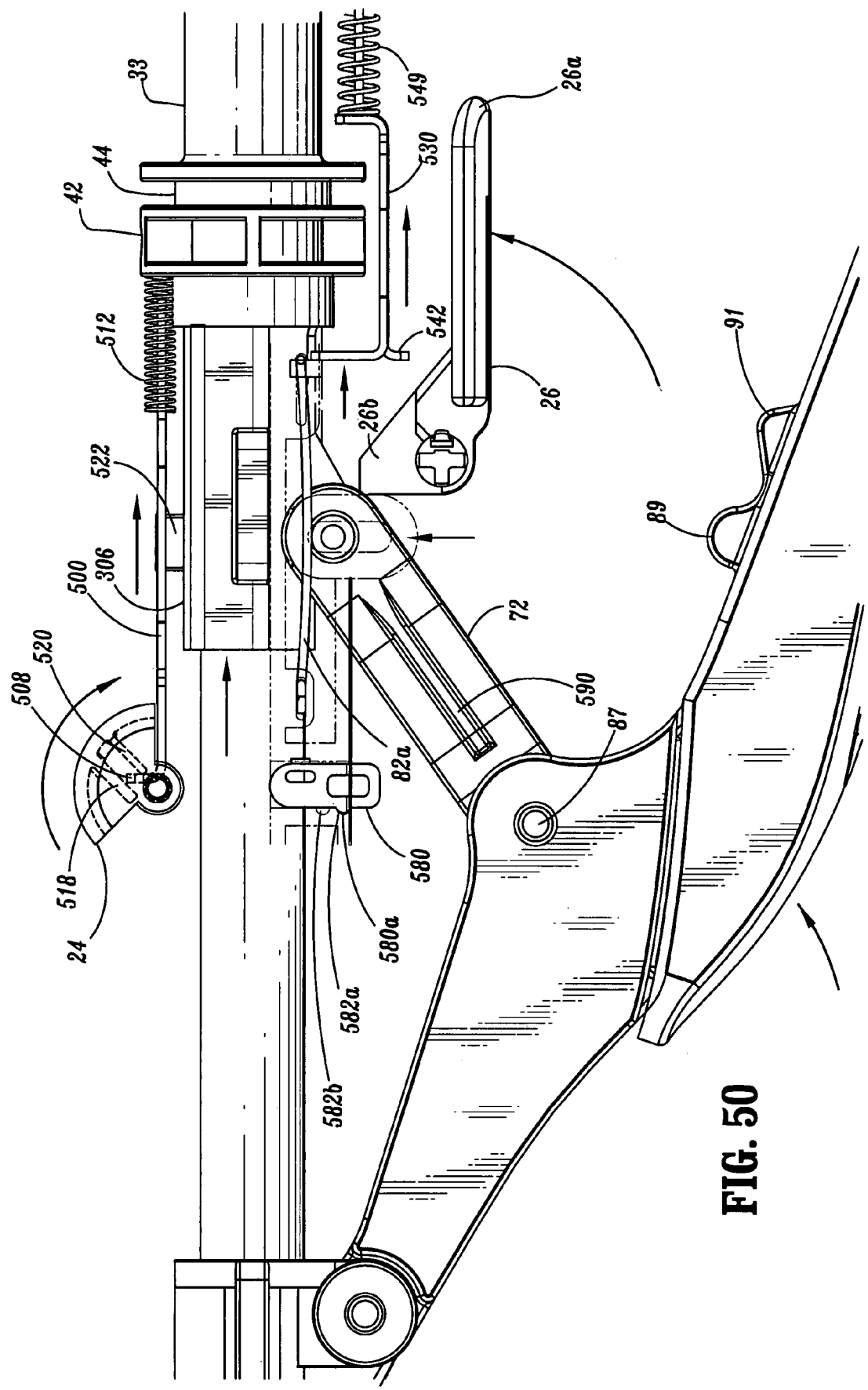
FIG. 50 is a side view of a portion of the handle assembly of the surgical stapler shown in FIG. 45 with the handle sections removed.

Referring to FIGS. 47-49, screw stop 306 is axially fixed to screw 32 by set screw 312. Thus, as screw 32 is retracted within sleeve 33, screw stop 306 is moved from a distal position within stationary handle 18 to a proximal position.

As screw stop 306 moves from the distal position to the proximal position, first engagement member 522 formed on screw stop 306 abuts proximal end 506a of slot 506 of slide plate 500 (FIG. 29) and moves slide plate 500 proximally against the bias of spring 512. As slide plate 500 moves proximally, lip 508 (FIG. 48) of slide plate 500 engages projection 520 of indicator 24 to pivot indicator 24 in a counter-clockwise direction as viewed in FIG. 48.

Screw stop 306 also includes a second engagement member 548 (FIG. 47). As screw stop 306 is moved from the distal position to the proximal position during approximation of anvil assembly 30, second engagement member 548 engages distal legs 540a of lockout member 530 to move lockout member 530 proximally to a position in which lip portion 542 is spaced proximally of extension 26b of trigger lock 26. In this position, trigger lock 26 can be pivoted to an unlocked position to permit firing of stapling device 10.

Movement of screw stop 306 to its proximal-most position within stationary handle 18 positions abutment surface 307 of screw stop 306 in position to engage pivot member 79 of firing link 72. Abutment surface 307 comprises a substantially concave surface which is positioned to partially capture and act as a backstop for pivot 79 during firing of stapling device 10.

FIGS. 51-56 illustrate surgical stapling device 10 during the firing stroke of firing trigger 20. As trigger 20 is compressed towards stationary handle 18 in the direction indicated by arrow "M" in FIG. 52, pivot member 79 engages abutment surface 307 on screw stop 306 and firing trigger 20 is pushed distally. As discussed above, the distal end of firing trigger 22 is connected through coupling member 86 to the proximal end of pusher link 74. Accordingly, as firing trigger 20 is moved distally, pusher link 74 is moved distally in the direction indicated by arrow "N" in FIG. 52 to effect advancement of pusher back 186 within shell assembly 31 (FIG. 52). Fingers 190 of pusher back 186 engage and eject staples 230 from staple guide 192.

Figure 56:
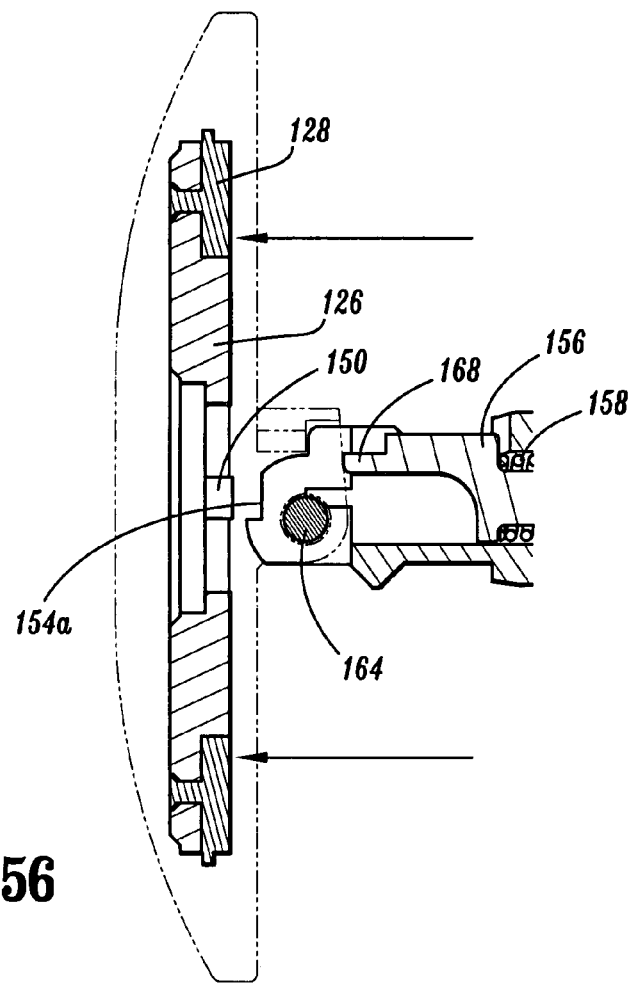
FIG. 56 is a side cross-sectional view of the distal portion of the anvil assembly shown in FIG. 55 with a portion of the anvil head assembly in phantom.
Figure 57:
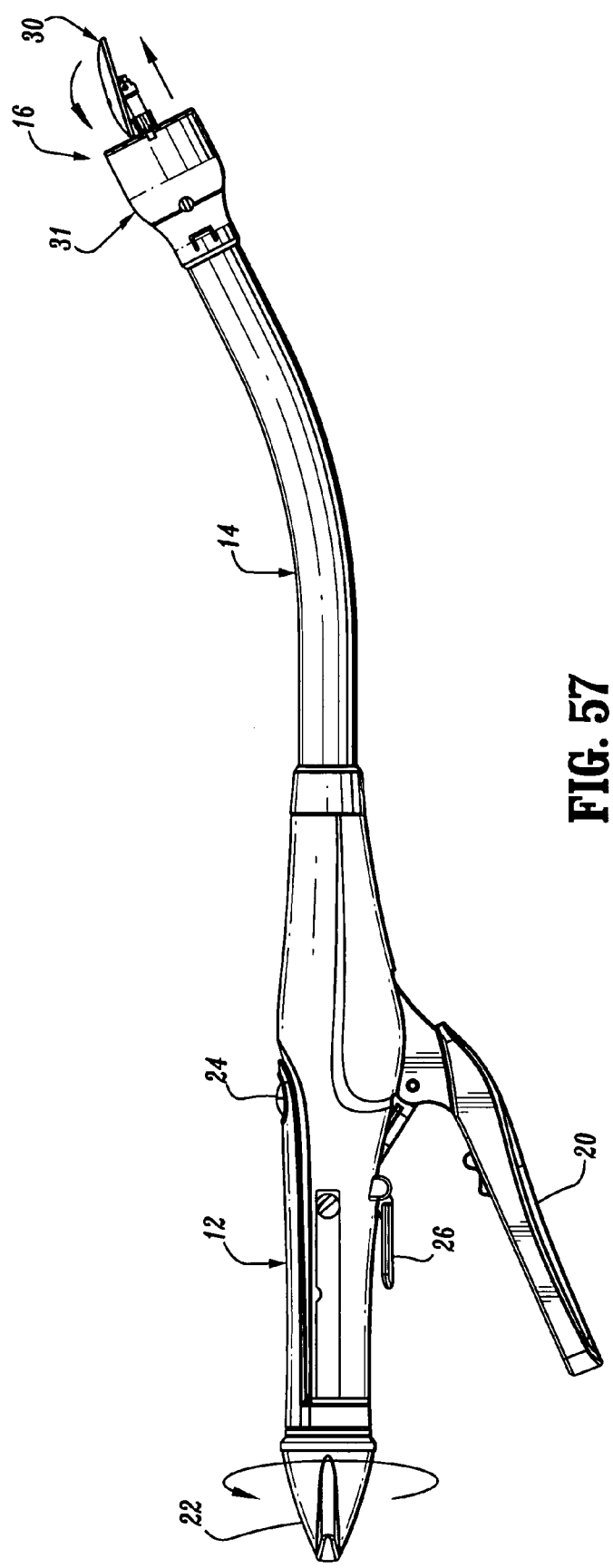
FIG. 57 is a side view of the surgical stapling device shown in FIG. 45 after the anvil assembly and cartridge assembly have been unapproximated a distance sufficient to permit the anvil head assembly to pivot on the anvil center rod.
Figure 59:
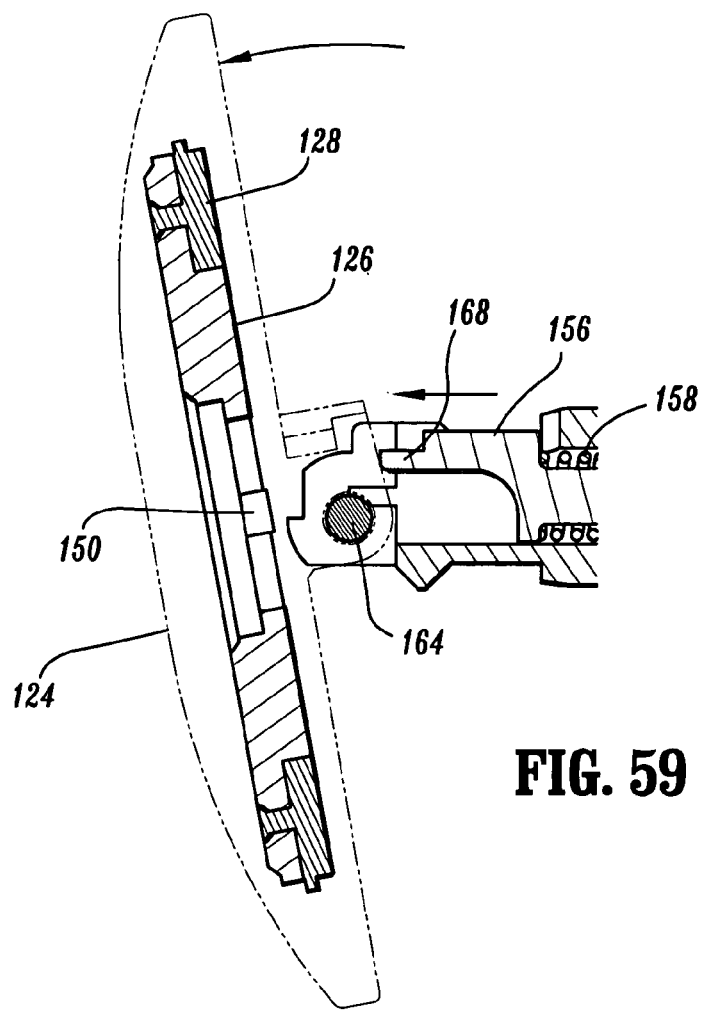
FIG. 59 is a side cross-sectional view of the anvil assembly shown in FIG. 56 as the anvil head assembly begins to tilt.
Figure 60:
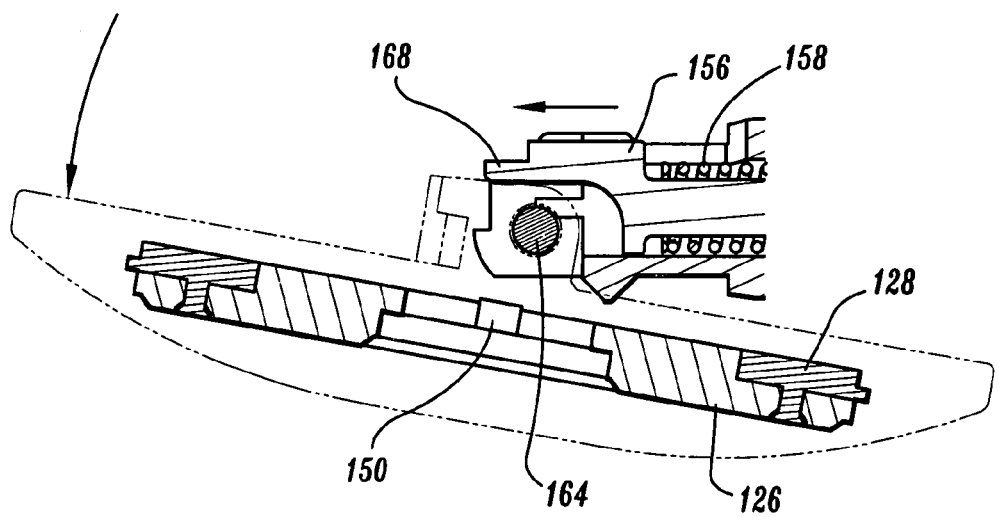
FIG. 60 is a side cross-sectional view of the anvil assembly shown in FIG. 59 with the anvil assembly tilted.
Figure 61:
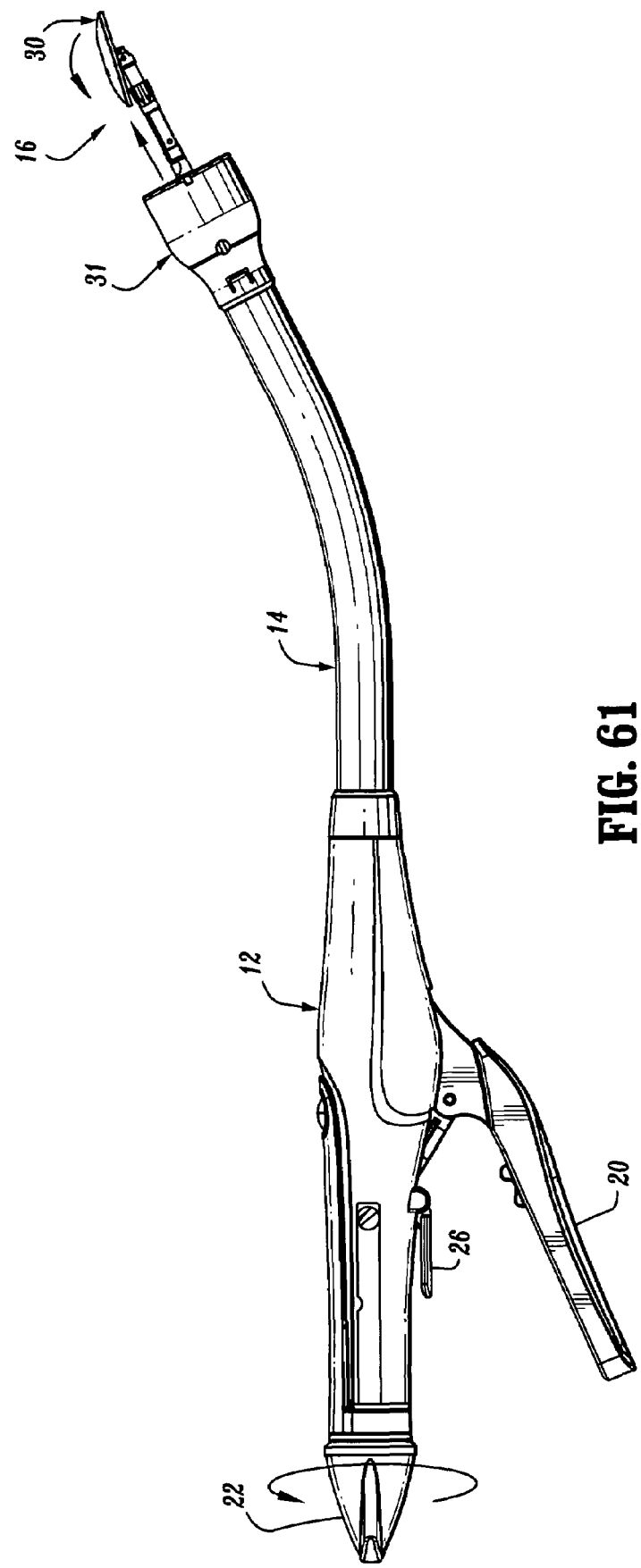
FIG. 61 is a side view of the surgical stapling device shown in FIG. 45 with the anvil head assembly unapproximated and tilted.

Cylindrical knife 188 is moved concurrently with pusher back 186 such that knife 188 moves into engagement with cutting ring 128 and backup plate 126. As discussed above, cutting ring 128 can be formed from polyethylene and backup plate 126 can be formed from metal. When knife 188 engages cutting ring 128, it cuts into cutting ring 128 and pushes backup plate 126 deeper into anvil head 124 to move tabs 150 (FIG. 56) from engagement with top surface 154a of center rod 154 (FIG. 56). Anvil head 124 is now free to pivot about member 164 and is urged to do so by plunger 156. It is noted that because the anvil assembly is in juxtaposed alignment with shell assembly 31, the anvil head 14 will not pivot fully until the anvil and shell assemblies have been unapproximated a distance sufficient to allow the anvil head to fully pivot. When backup plate 126 moves into anvil head 124, flexible arms 127a and 127b of retainer clip 127 (FIG. 55) spring outwardly to a position in front of backup plate 126 blocking movement of backup plate 126 out of anvil head 124. As discussed above, arms 127a and 127b prevent backup plate 126 from sticking to knife 188 when anvil assembly 30 is returned to the unapproximated position.

Figure 53:
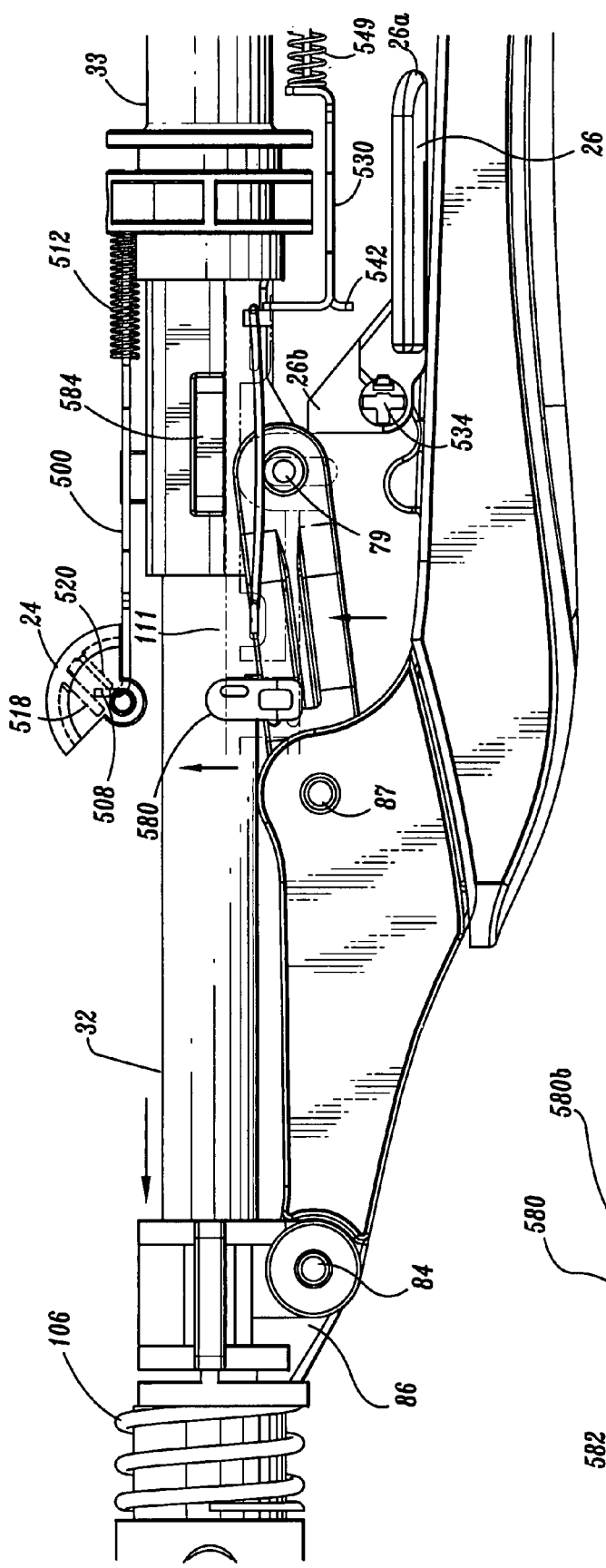
FIG. 53 is a side view of the handle assembly shown in FIG. 51 with the handle sections removed.
Figure 58:
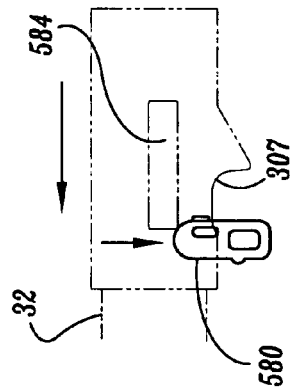
FIG. 58 is an enlarged view of the abutment member of the tactile indicator mechanism of the handle assembly shown in FIG. 53 (during unapproximation of the anvil and cartridge assemblies) with the wing of the screw stop, shown in phantom, in engagement with the abutment member.
Figure 54:
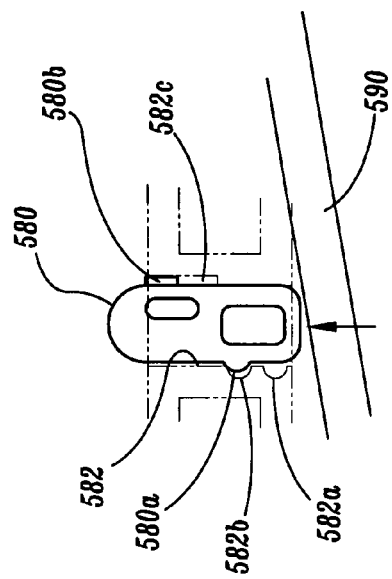
FIG. 54 is an enlarged view of the firing link extension engaging the abutment member of the tactile indicator mechanism of the handle assembly shown in FIG. 53.
Figure 55:
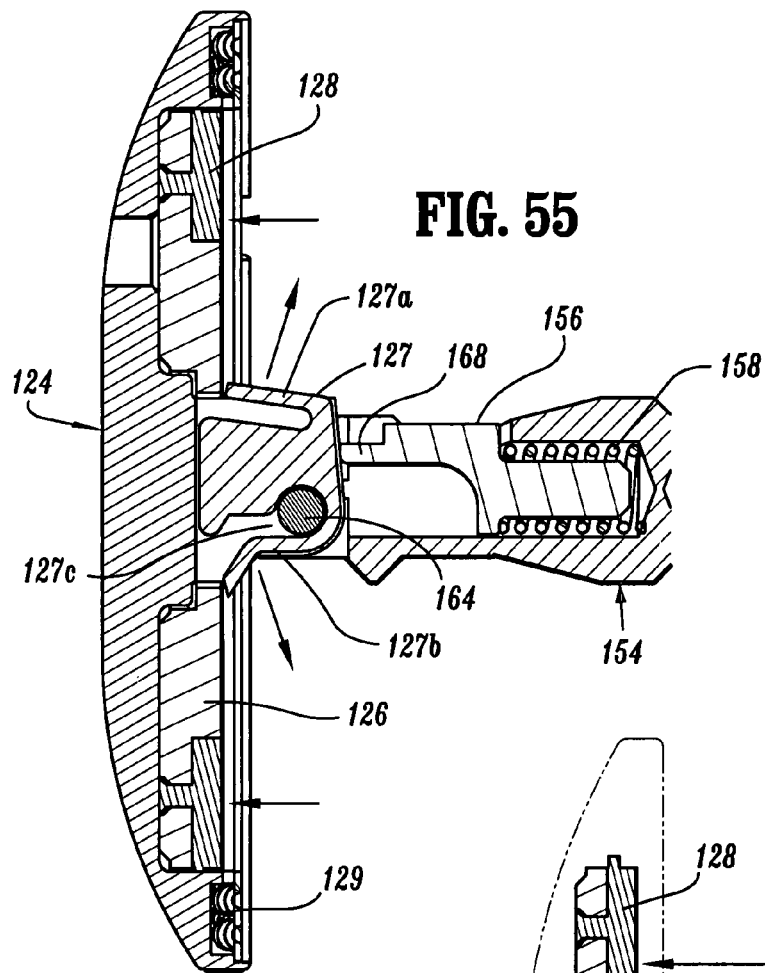
FIG. 55 is a side cross-sectional view of the distal portion of the anvil assembly of the surgical stapling device shown in FIG. 52.

Referring to FIGS. 53 and 54, as trigger 20 is actuated, i.e., compressed towards stationary handle 18, extension 590 of firing link 72 is pivoted towards and engages abutment member 580 to move abutment member 580 from its retracted to its extended position. In its extended position, abutment member 580 obstructs channel 111 of stationary handle 18.

Referring to FIGS. 57-60, during unapproximation of stapling device 10 after device 10 has been fired, wing 584 of screw stop 306 engages abutment member 580 of the tactile indicator mechanism (FIG. 58) at the point of unapproximation at which anvil head 124 is able to pivot to the tilted reduced profile position. Contact between wing 584 and abutment member 580 provides a tactile and/or audible indication that anvil head 124 has tilted. If additional force is provided to approximation knob 22, wing 584 of screw stop 306 will force abutment member 580 to the retracted position to allow stapling device 10 to move to the fully open position. In this position, flexible arms 155 are positioned distally of bushing 209 and anvil assembly 30 can be disengaged from anvil retainer 28.

FIGS. 62-74 illustrate another embodiment of the presently disclosed surgical stapling device shown generally as 600. Stapling device 600 is particularly suited for use in minimally invasive gastric bypass procedures. Such a procedure is described in PCT application Ser. No. PCT/US01/07105, filed Mar. 5, 2001, which is incorporated herein by reference in its entirety. Alternately, surgical stapling device 600 may be used in other surgical procedures, especially those procedures in which a reduced profile anvil assembly is required or desired.

Figure 62:
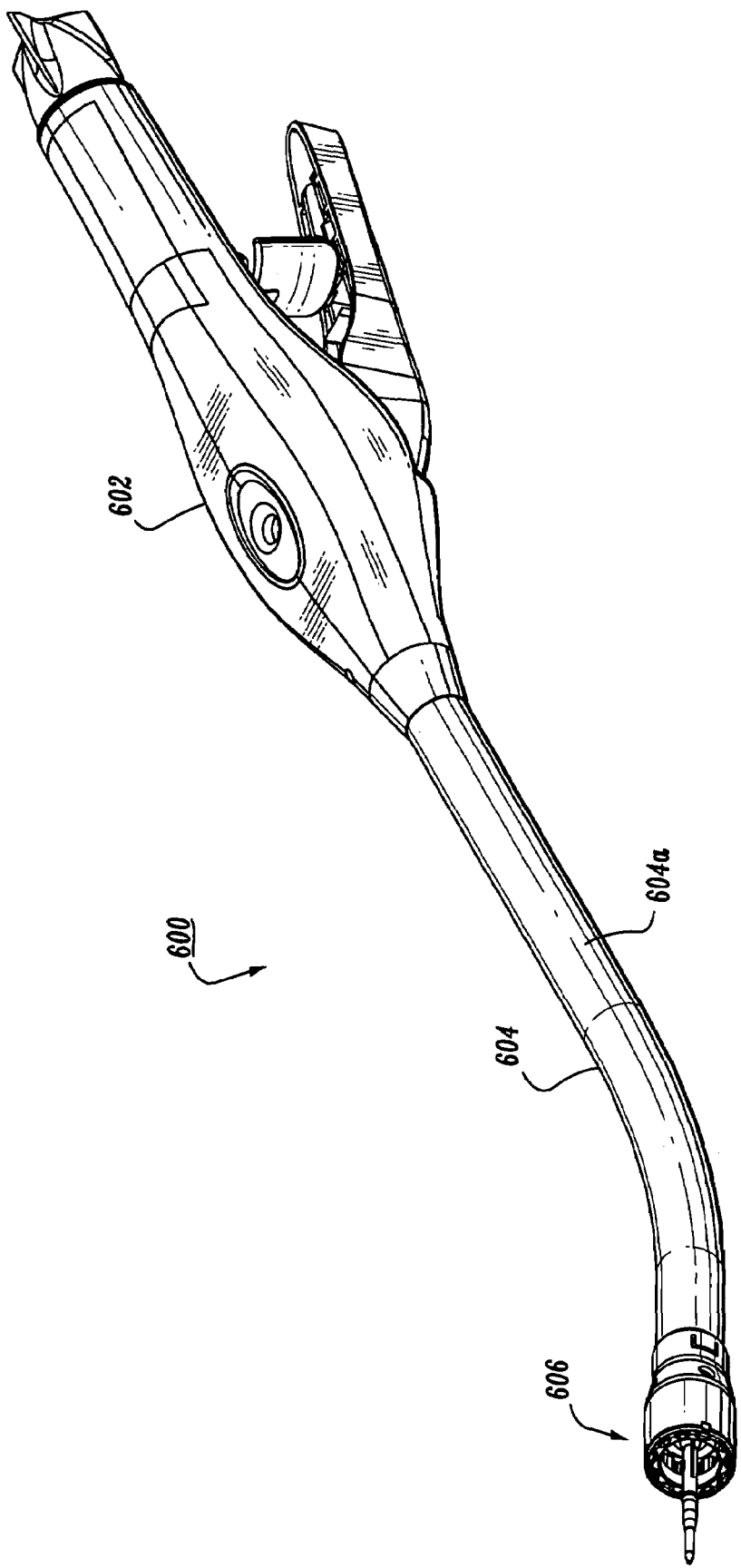
FIG. 62 is a side perspective view from the distal end of an alternate embodiment of the presently disclosed surgical stapling device with the anvil assembly removed from the device.

Referring to FIG. 62, surgical stapling device 600 includes a proximal handle assembly 602, an elongated body portion 604 including curved outer tube 604a, and a distal head portion 606. Since the components of handle assembly 602 and body portion 604 are substantially similar to handle assembly 12 and body portion 14 discussed above, these portions of surgical stapling device 600 will not be discussed in further detail herein.

Figure 65:
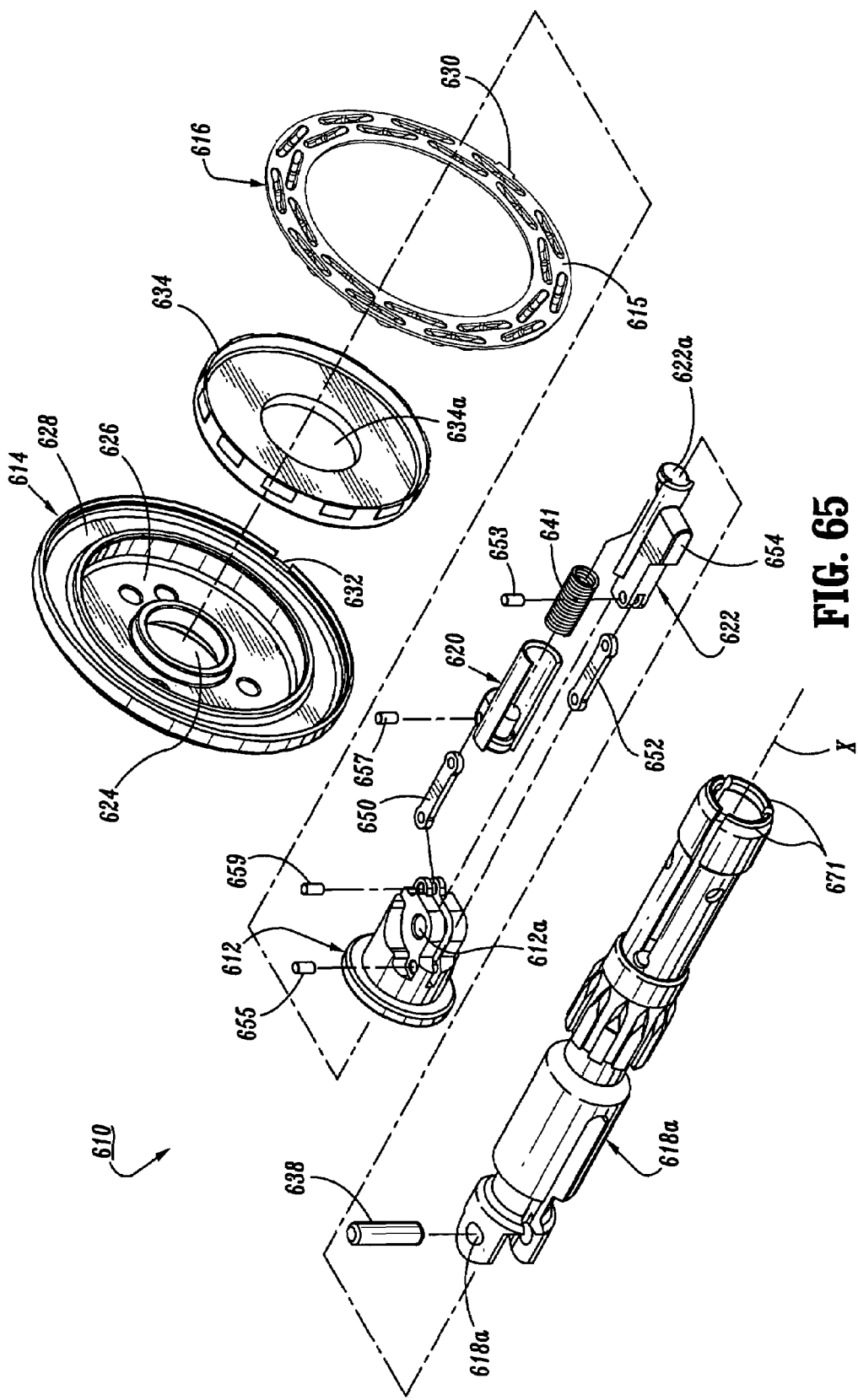
FIG. 65 is a side exploded perspective view of the anvil assembly shown in FIG. 63.

Referring to FIGS. 63-65, an anvil assembly 610 is provided for releasable attachment to surgical stapling device 600. Anvil assembly 610 includes an anvil post 612, an anvil head 614, an anvil plate 616, a center rod 618, a first slide member 620 and a second slide member 622. Anvil head 614 includes a centrally located through bore 624 (FIG. 65) dimensioned to receive anvil post 612, an inner annular recess 626 and an outer annular recess 628. Outer annular recess 628 is configured to receive anvil plate 616. Anvil plate 616 includes a tab 630 (FIG. 65) which is dimensioned to be received within a slot 632 formed in anvil head 614. Tab 630 and slot 632 cooperate to position anvil plate 616 in the proper orientation within outer recess 628. Inner annular recess 626 is configured to receive a cutting ring 634 which includes a central opening 634a which is dimensioned to be positioned about anvil post 612 and a portion of anvil head 614 defining an inner boundary of annular recess 626.

Anvil post 612 includes a transverse bore 612a for receiving a pivot member 638. Pivot member 638 pivotally connects anvil post 612 to one end of center rod 618 via cooperating bore 618a formed in center rod 618. In one embodiment, pivot member 638 includes a pin or post which defines a transverse axis which is spaced laterally from the longitudinal axis "x" (FIG. 65) defined by center rod 618 such that anvil head 614 can pivot approximately 90 degrees from an operative position (FIG. 68) in which a plane defined by tissue contact surface 615 of the anvil head 614 is substantially perpendicular to the longitudinal axis "x" of center rod 618 to a tilted reduced profile position (FIG. 63) in which anvil head 614 is substantially parallel to longitudinal axis "x" of center rod 618. Alternately, other types of pivot members at a variety of locations in relation to longitudinal axis "x" of center rod 618 may be incorporated into anvil assembly 610. For example, as illustrated in FIGS. 64A and 64B, pivot member 638' for anvil head 614' may be positioned on the longitudinal axis of center rod 618'.

Center rod 618 includes a throughbore 640 (FIG. 64) having a first end 642 and a second end 644. In one embodiment, second end 644 includes at least one opening 646 dimensioned to receive a suture or the like to facilitate positioning of anvil assembly 610 within a hollow organ. First end 642 of throughbore 640 is dimensioned to slidably receive at least a portion of first and second slide members 620 and 622 which are movable in relation to each other. A spring or biasing member, e.g., coil spring 641, is positioned between first and second slide members 620 and 622 to urge the slide members apart or away from each other. A drive link 652 is pivotally connected at one end to second slide member 622 and at the other end to anvil post 612 by pivot members 653 and 655, respectively. A return link 650 is pivotally connected at one end to first slide member 620 and at the other end to anvil post 612 by pivot members 657 and 659, respectively. Links 650 and 652 are connected to slide members 620 and 622 and anvil post 612 in such a manner that when biasing member 641 urges first and second slide members 620 and 622 apart, anvil head 614 pivots about pivot member 638 to its tilted reduced profile position (FIG. 63).

Center rod 618 includes a plurality of flexible arms 671 which define a second end 644 of throughbore 640 which is dimensioned to releasably engage a removable trocar, adaptor or anvil retainer as discussed above with respect to stapling device 10. A plurality of splines 673 are formed about center rod 618. Splines 673 mesh with grooves (not shown) formed in stapling device 600 as described above to properly align anvil assembly 610 in relation to shell assembly 700 of surgical stapling device 600 during approximation of the anvil and shell assemblies.

Figure 66:
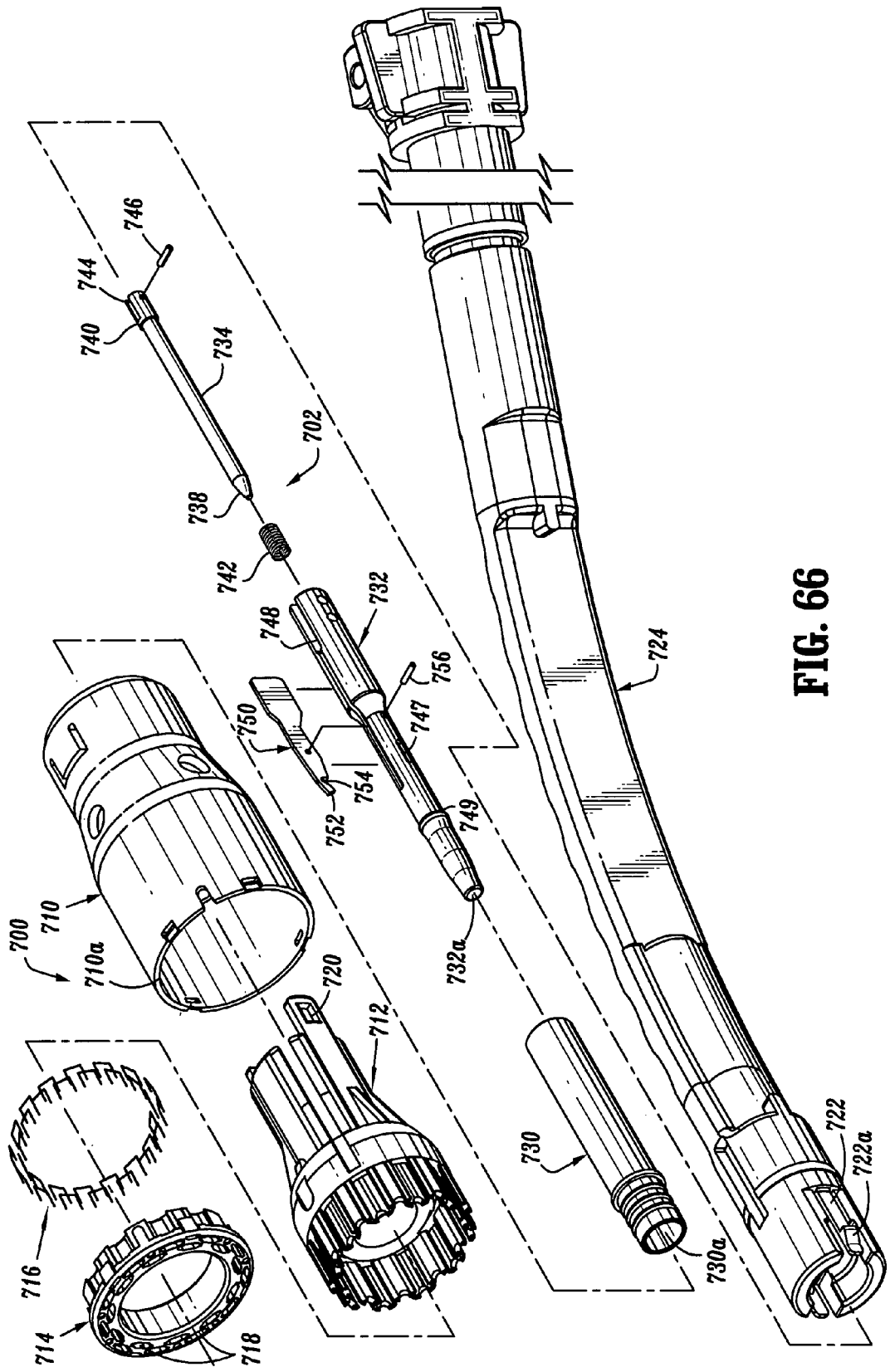
FIG. 66 is a side exploded perspective view of the distal head portion, anvil retainer assembly and pusher back of the surgical stapling device shown in FIG. 62.
Figure 67:
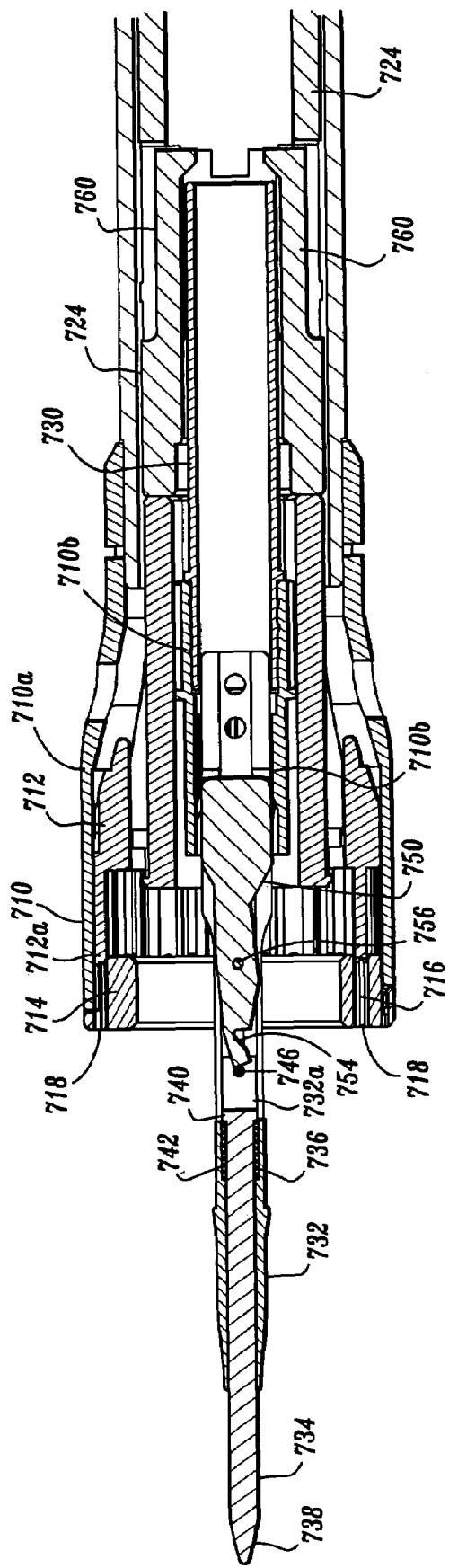
FIG. 67 is a side cross-sectional view of the distal end of the central body portion and distal head portion of the surgical stapling device shown in FIG. 62 with the anvil assembly removed.

FIGS. 66 and 67 illustrate the shell assembly 700 and anvil retainer assembly 702 of surgical stapling device 600 (FIG. 62). FIGS. 66 and 67 also illustrate the pusher 724 of the firing mechanism of stapling device 600. Although not shown in this figure, anvil retainer assembly 702 is connected to an approximation mechanism, such as screw extensions 34 and 36 (FIG. 6) disclosed above, and pusher 724 is connected to the firing mechanism of a stapling device, such as firing trigger 20, disclosed above.

Shell assembly 700 includes a shell or housing 710, a pusher back 712, a cylindrical knife (not shown), a staple guide 714 and a plurality of staples 716. Shell 710 includes an outer housing portion 710a and an inner housing portion 710b (FIG. 67). Staple guide 714 is supported in the distal end of outer housing portion 710a and includes an annular array of staple receiving pockets 718 for housing staples 716. Pusher back 712 is slidably supported in shell 710 between outer housing portion 710a and inner housing portion 710b between retracted and advanced positions. Pusher back 712 includes a plurality of fingers 712a which are each slidably received in respective staple pockets 718 in staple guide 714. Pusher back 712 includes a pair of recesses 720 which receive detents 722a formed on flexible fingers 722 of a pusher 724 to secure pusher 724 to pusher back 712. Pusher back 712 is movable from its retracted position to its advanced position, in the manner discussed above with respect to pusher back 186, to eject staples 716 from staple guide 714.

An elongated hollow bushing 730 is fixedly retained in inner housing portion 710b of shell 710 using screw threads, a friction fitting, or the like. Bushing 730 defines a channel 730a through which anvil retainer assembly 702 reciprocates during approximation and unapproximation of anvil and shell assemblies 610 and 700, respectively.

Anvil retainer assembly 702 includes a two-part assembly having a body portion 732 defining a longitudinal throughbore 732a and a trocar or locking member 734 slidably received within the longitudinal throughbore. Longitudinal throughbore 732a includes a stepped portion or shoulder 736.

Trocar 734 includes a blunt tip 738 at one end thereof and an annular flange or shoulder 740 at the other end thereof. Alternately, a less blunt, i.e., sharper, or more blunt trocar may be provided. Tip 738 of trocar 734 extends from a distal end of body portion 732 of the trocar assembly 702 and is movable within throughbore 732a from an advanced position to a retracted position. A biasing member, e.g., a coil spring 742, is positioned between annular flange 740 and shoulder 736 (FIG. 67) and urges trocar 734 to its retracted position. The proximal end of trocar 734 includes a transverse slot 744 having a pin or rod 746 extending therethrough. Pin 746 is slidably positioned within longitudinal slots 747 formed in body portion 732. The distal and proximal ends of slots 747 define the advanced and retracted positions of trocar 734, respectively.

Body portion 732 of assembly 702 includes an annular protrusion 749 a longitudinal slot 748. Annular protrusion 749 facilitates attachment of anvil assembly as discussed above. A cam member 750 is pivotally supported about a pivot member 756 in slot 748 at a position proximal of pin 746. Cam member 750 includes a distal finger 752 having an angled face and a recess 754 positioned proximally of finger 752 for receiving pin 746 of trocar 734. Pin 746 is urged by coil spring 742 towards finger 752. Engagement between the angled face of finger 752 and pin 746 urges cam member 750 to pivot about pivot member 756 to allow pin 746 to move into recess 754.

Figure 66A:
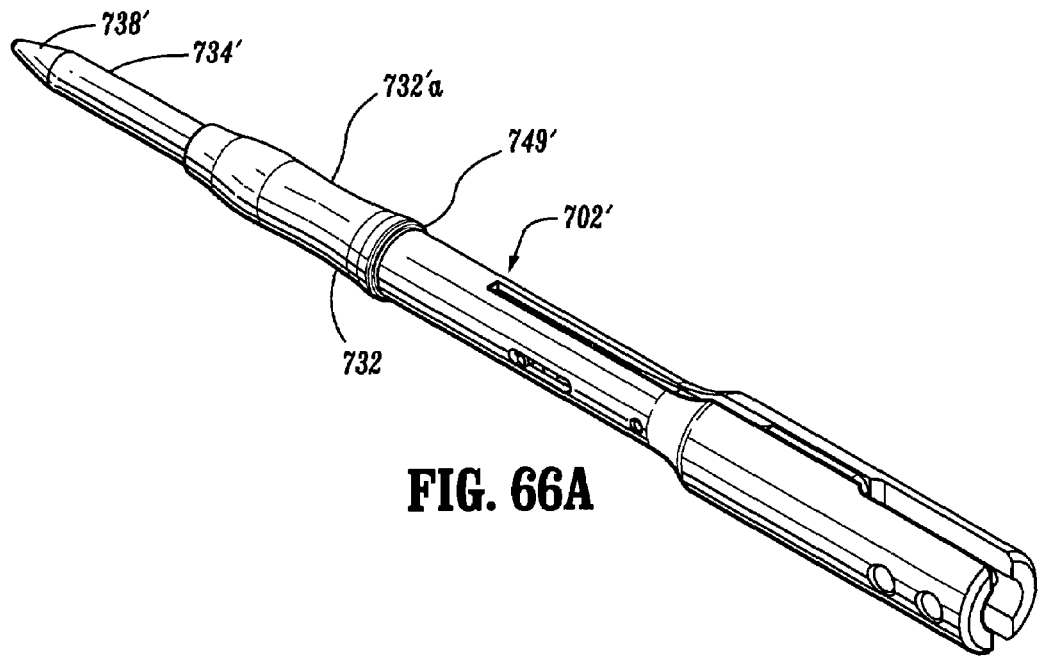
FIG. 66A is a side perspective view from the proximal end of another embodiment of the anvil retainer assembly shown in FIG. 66.
Figure 66B:
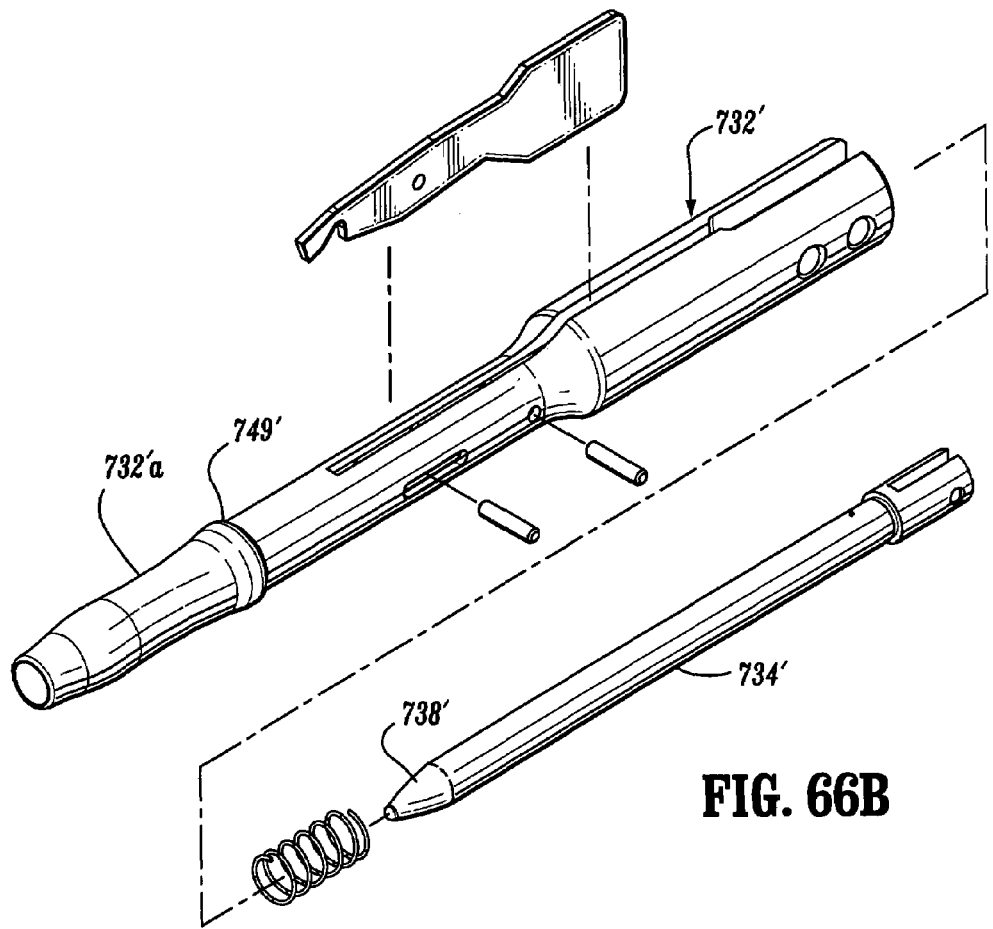
FIG. 66B is a side exploded perspective view from the distal end of the anvil retainer assembly shown in FIG. 66A.

FIGS. 66A and 66B illustrate an alternate embodiment of anvil retainer assembly 702 shown generally as 702'. Anvil retainer assembly 702' includes a trocar or locking member 734' having a blunt tip 738' and a body portion 732'. Anvil retainer assembly 702' is substantially identical to anvil retainer 702 with the exception that the shape of body portion 732' has been changed to define a smooth concavity 732'a or coke bottle shape between annular protrusion 749' and the distal end of body portion 732'. The shape permits tissue to slide smoothly over the body portion 732' of anvil retainer assembly 702 prior to attachment of an anvil assembly thereto.

Figure 72:
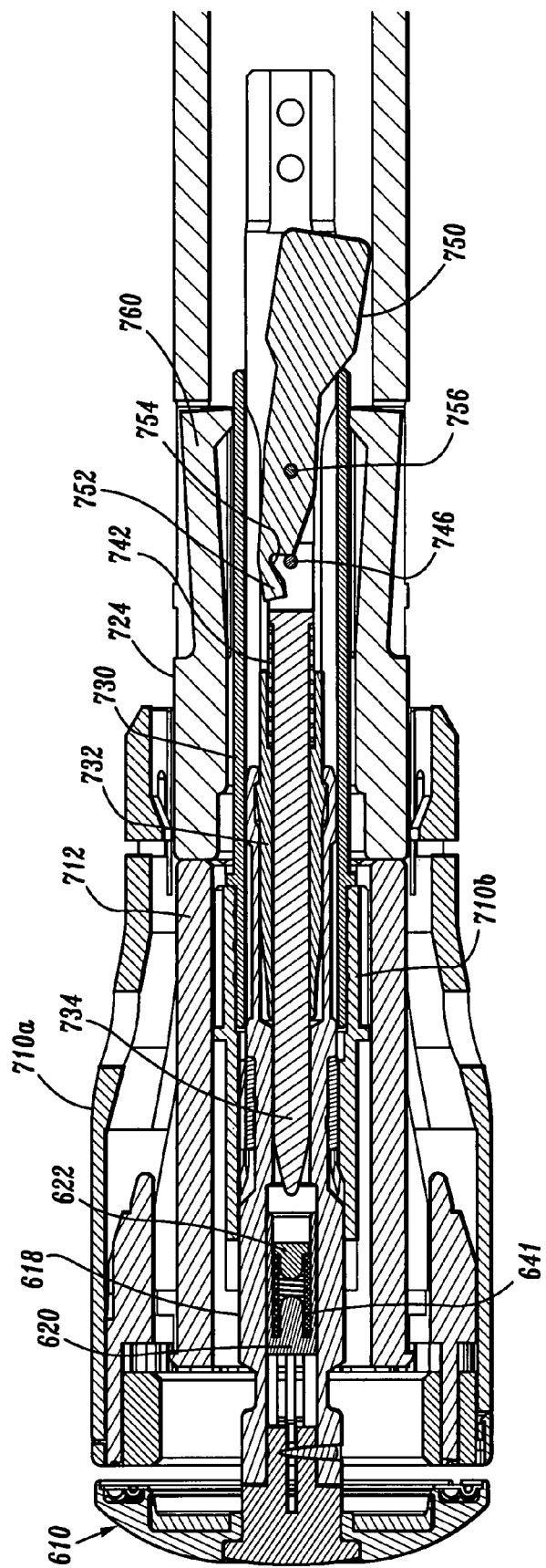
FIG. 72 is a cross-sectional view of the distal end of the central body portion and distal head portion shown in FIG. 70 after the stapling device has been fired.

When assembly 702 is positioned within bushing 730 (when surgical stapling device 600 is not fully approximated), cam member 750, which is urged by trocar pin 746 to a pivoted position, is prevented from pivoting by engagement with the inner walls of bushing 730. In its non-pivoted position (FIG. 67), cam member finger 752 engages pin 746 of trocar 734 to lock trocar 734 in its distal or advanced position. When anvil retainer 702 is withdrawn from bushing 730 a distance sufficient to withdraw cam member 750 from bushing 730, engagement between pin 746 of trocar 734 and the angled face of finger 752 of cam member 750 moves cam member 750 to a pivoted position (FIG. 72). In the pivoted position, pin 746 moves proximally past the angled face of finger 752 into recess 754 and trocar 734 is moved from its advanced position to its retracted position by biasing member 742.

Figure 70:
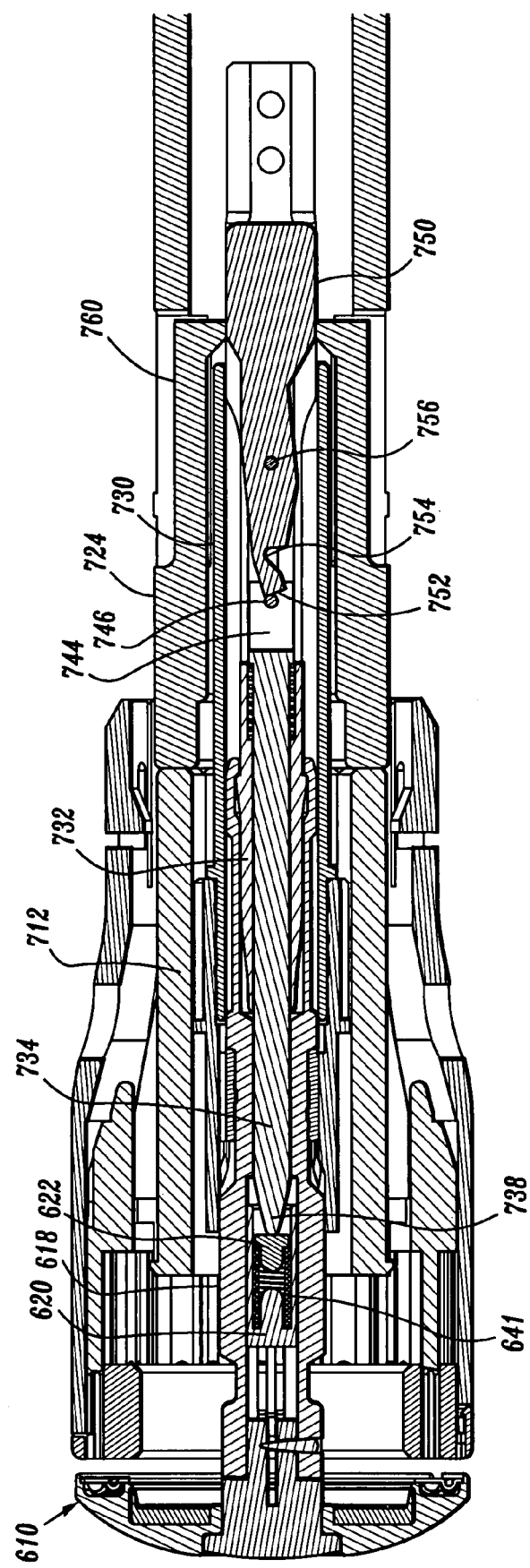
FIG. 70 is a cross-sectional view of the distal end of the central body portion and distal head portion shown in FIG. 68 with the anvil head moved to the approximated position.

As illustrated in FIG. 67, pusher 724 extends about the proximal end of bushing 730. In one embodiment, pusher 724 includes a pair of flexible arms 760 which extend radially inwardly adjacent the proximal end of bushing 730. Arms 760 are positioned to prevent cam member 750 from pivoting to a position to allow retraction of trocar 734 even when the device has been approximated (FIG. 70). However, when the surgical stapling device is fired, pusher 724 is moved distally and arms 760 deform over bushing 730 to permit pivoting of cam member 750 and facilitate retraction of trocar 734 (FIG.

72). Thus, when pusher 724 is provided with arms 760, trocar 734 will not move to its retracted position until device 600 has been approximated and fired.

Figure 68:
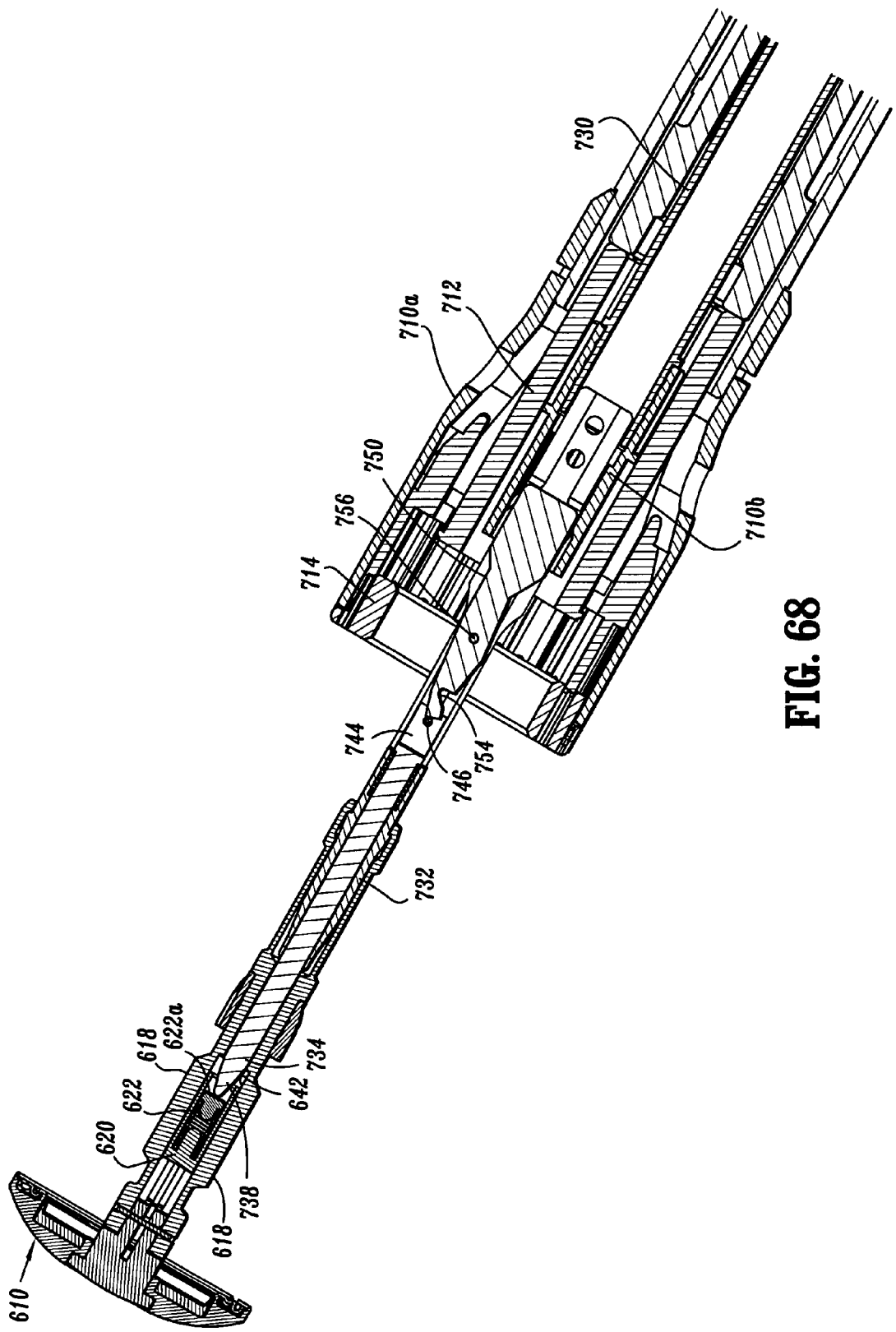
FIG. 68 is side cross-sectional view of the distal end of the central body portion and distal head portion shown in FIG. 67 with the anvil assembly shown in FIG. 63 secured to the anvil retainer assembly, the anvil assembly in its unapproximated position and the anvil head in the operative position.
Figure 69:
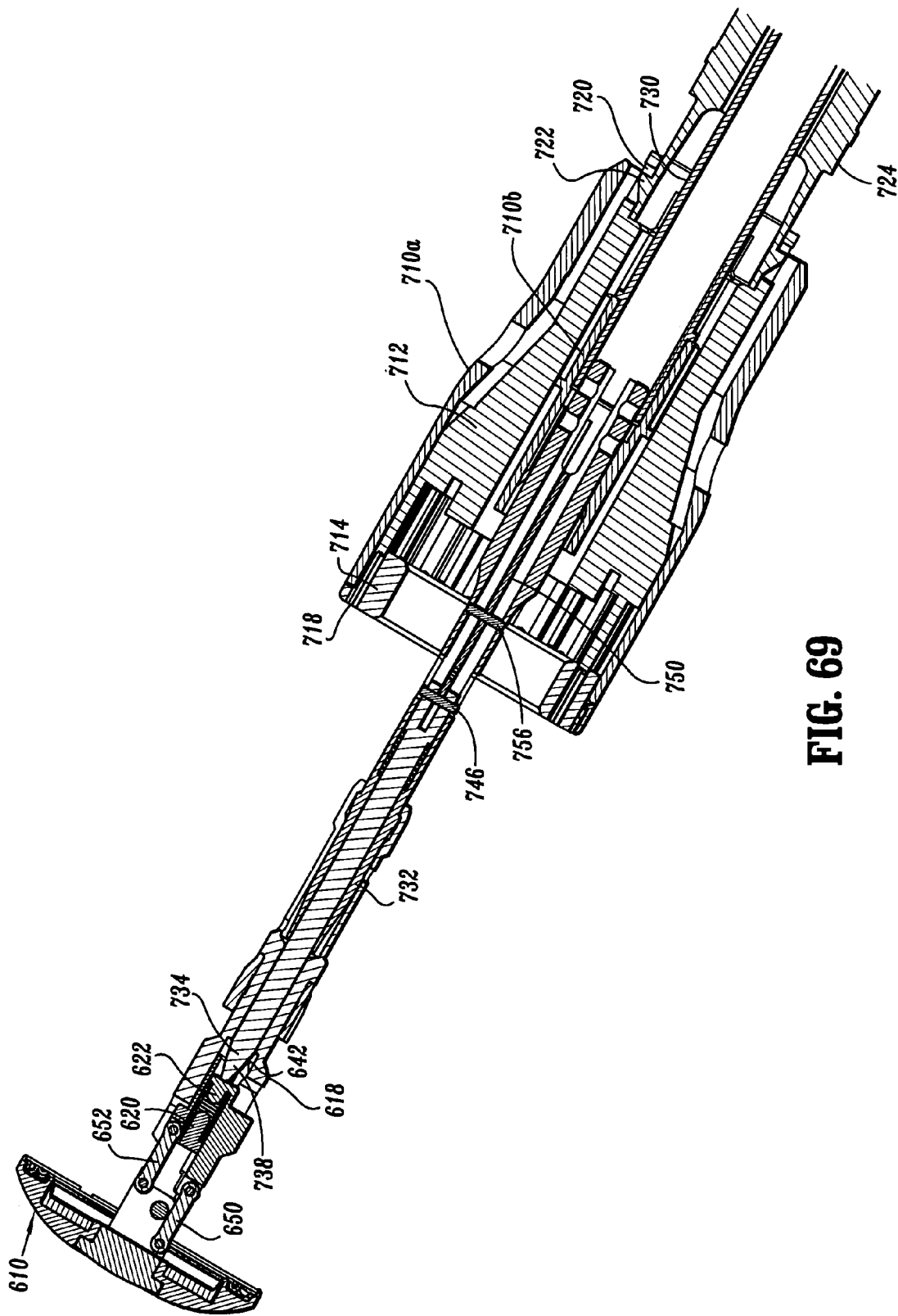
FIG. 69 is a cross-sectional view of the distal end of the central body portion and distal head portion shown in FIG. 68 taken along section lines ninety-degrees offset from the section lines of FIG. 68.

Referring to FIGS. 68 and 69, anvil assembly 610 is secured to anvil retainer assembly 702 by inserting retractable trocar 734 into bore 642 of center rod 618 of anvil assembly 610. Because the anvil retainer assembly 702 is unapproximated when anvil assembly 610 is attached and device 600 has yet to be fired, trocar 734 is in its advanced position. When trocar 734, in its advanced position, is inserted into center rod bore 642, tip 738 of trocar 732 engages a base portion 622a of second slide member 622 and moves second slide member 622 towards first slide member 620 to move anvil head 614 from its tilted position to its approximated position via links 650 and 652.

Figure 71:
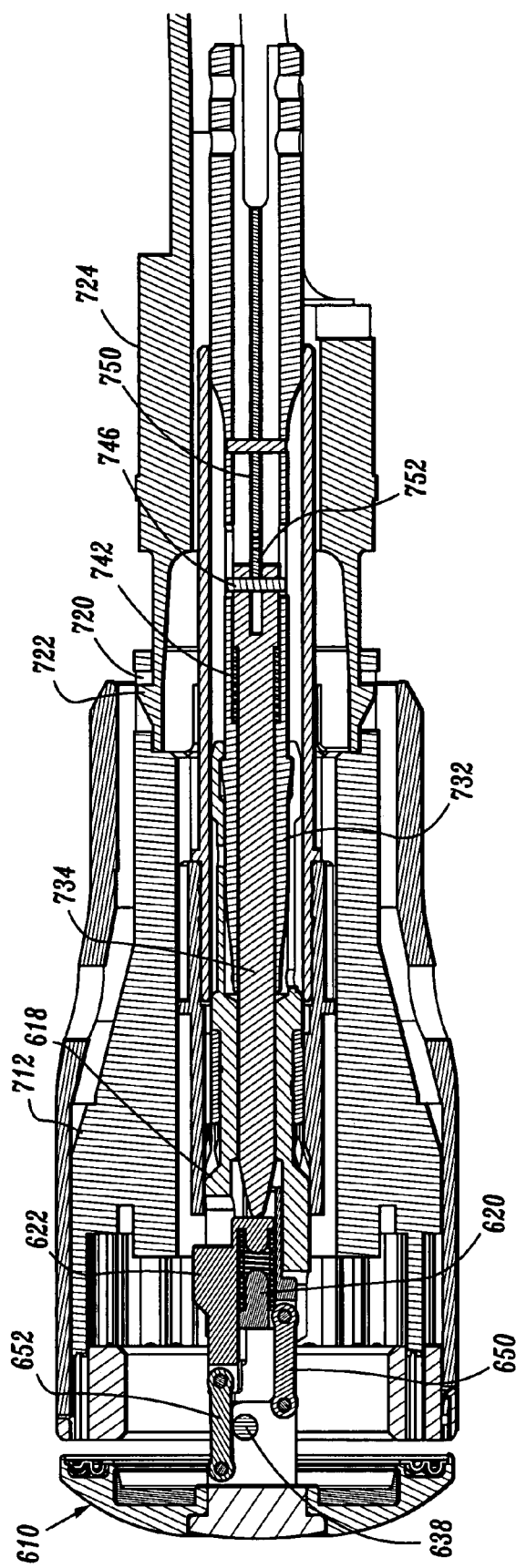
FIG. 71 is a cross-sectional view of the distal end of the central body portion and distal head portion shown in FIG. 69 with the anvil head moved to the approximated position.

Referring to FIGS. 70 and 71, when the anvil assembly 610 and shell assembly 700 are approximated, cam member 750 is prevented from pivoting by bushing 730 and arms 760 of pusher 724. Since cam member 750 is not free to pivot, finger 752 is positioned to prevent pin 746 from moving proximally within body portion 732 of assembly 702 to prevent retraction of trocar 734. As such, trocar tip 738 engages second slide member 622 to retain second slide member 622 in its advanced position. As such, anvil head 614 is retained in the operative, non-tilted position.

Figure 73:
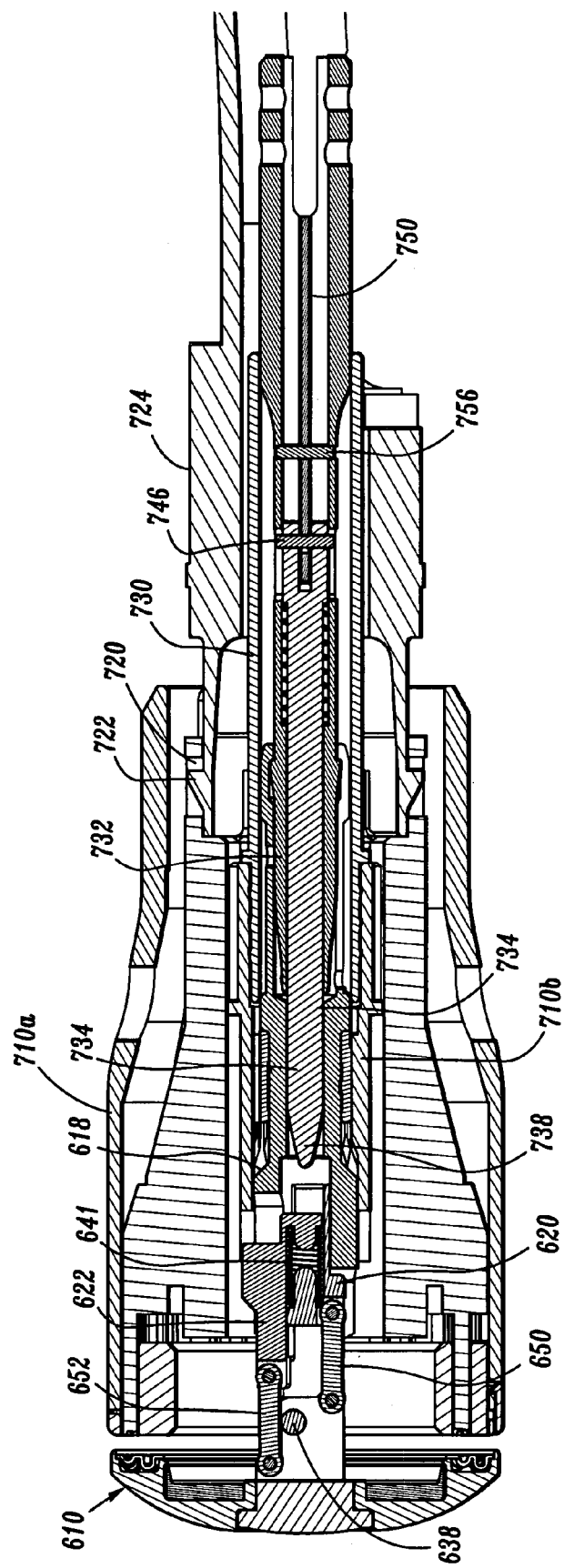
FIG. 73 is a cross-sectional view of the distal end of the central body portion and distal head portion shown in FIG. 71 after the stapling device has been fired.
Figure 74:
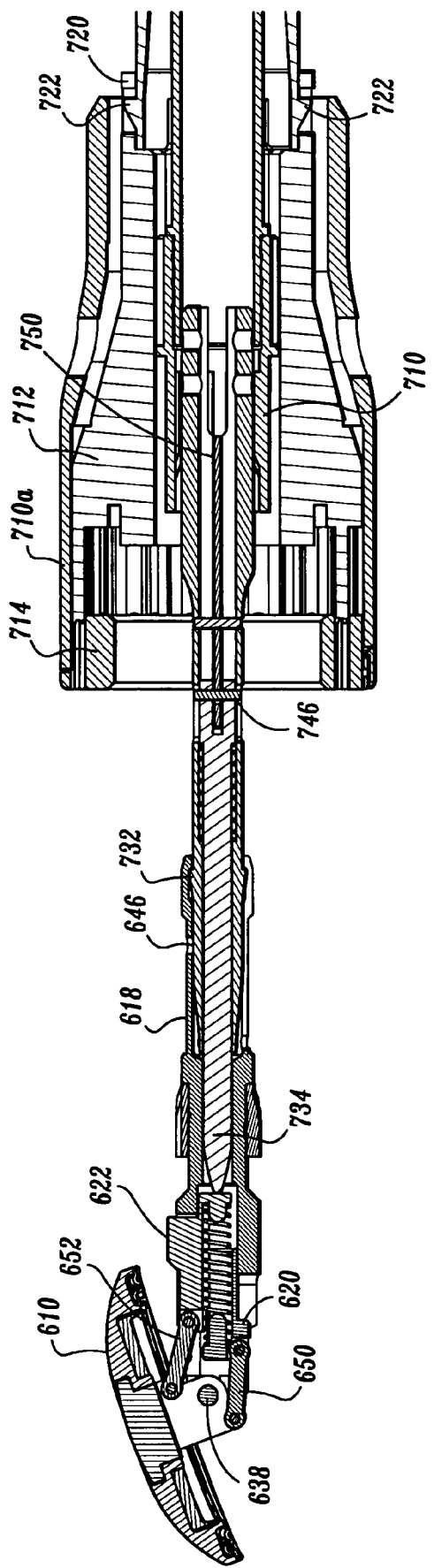
FIG. 74 is a cross-sectional view of the distal end of the central body portion and distal head portion shown in FIG. 73 after the anvil head has been unapproximated and pivoted to the tilted position.
Figure 74A:
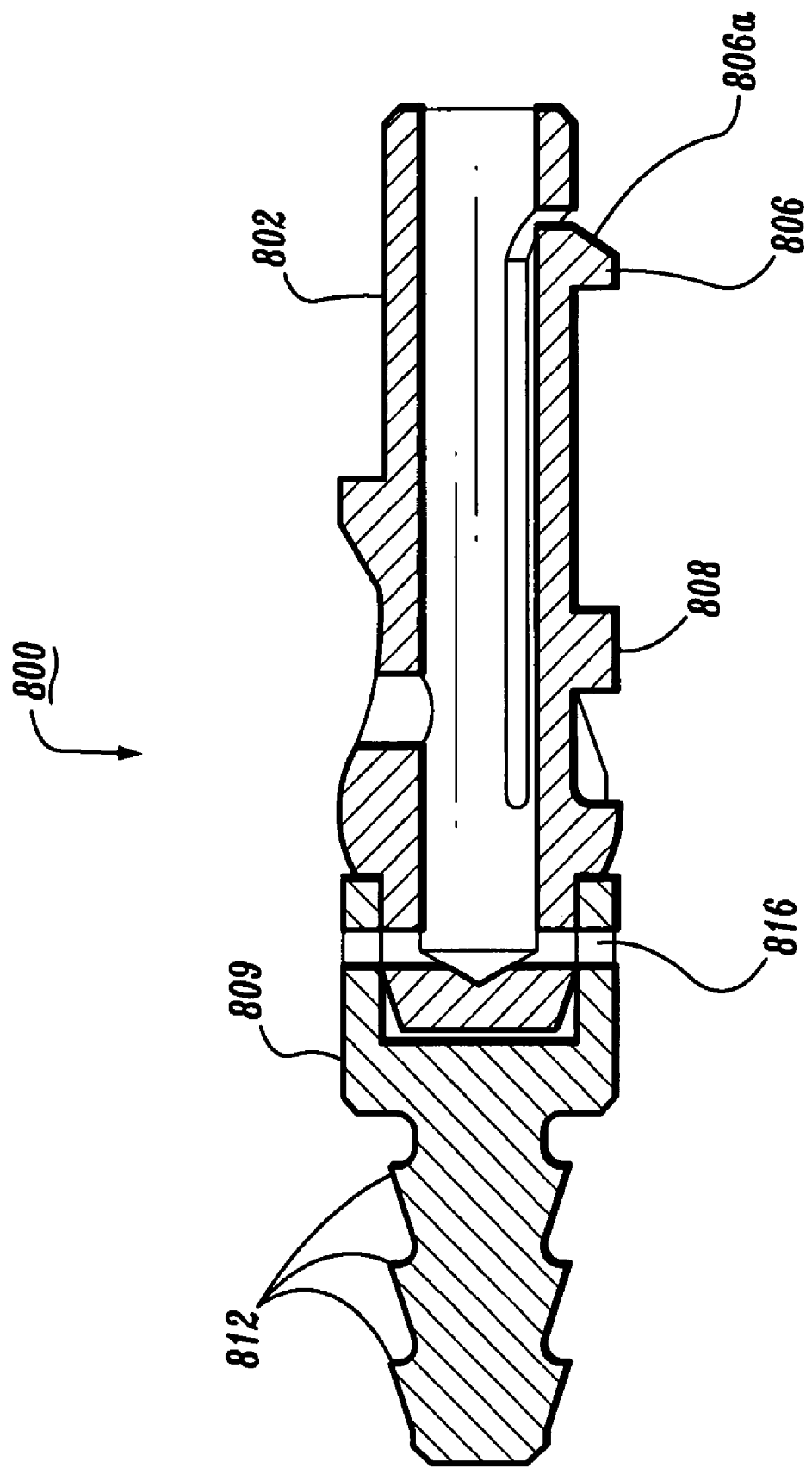
FIG. 74A is a side cross-sectional view of an anvil adaptor suitable for use during a gastric bypass procedure.

Referring to FIGS. 72 and 73, when stapling device 600 is fired and pusher 724 is moved distally about bushing 730, arms 760 are deformed outwardly away from cam member 750. Engagement between pin 746 and the angled face of finger 752 causes cam member 750 to pivot. When cam member 750 pivots, pin 746 moves proximally into recess 754 of cam member 750 and trocar 734 moves to the retracted position under the bias of spring 742. As trocar 734 moves to its retracted position, biasing member 641 urges first and second slide members 620 and 622 apart to urge anvil head 614 to its tilted reduced profile position (see FIG. 74). Because of the proximity of anvil head 614 to shell assembly 700, anvil head 614 will only move to its tilted reduced profile position during unapproximation of the anvil and shell assemblies 610 and 700, respectively.

Figure 75:
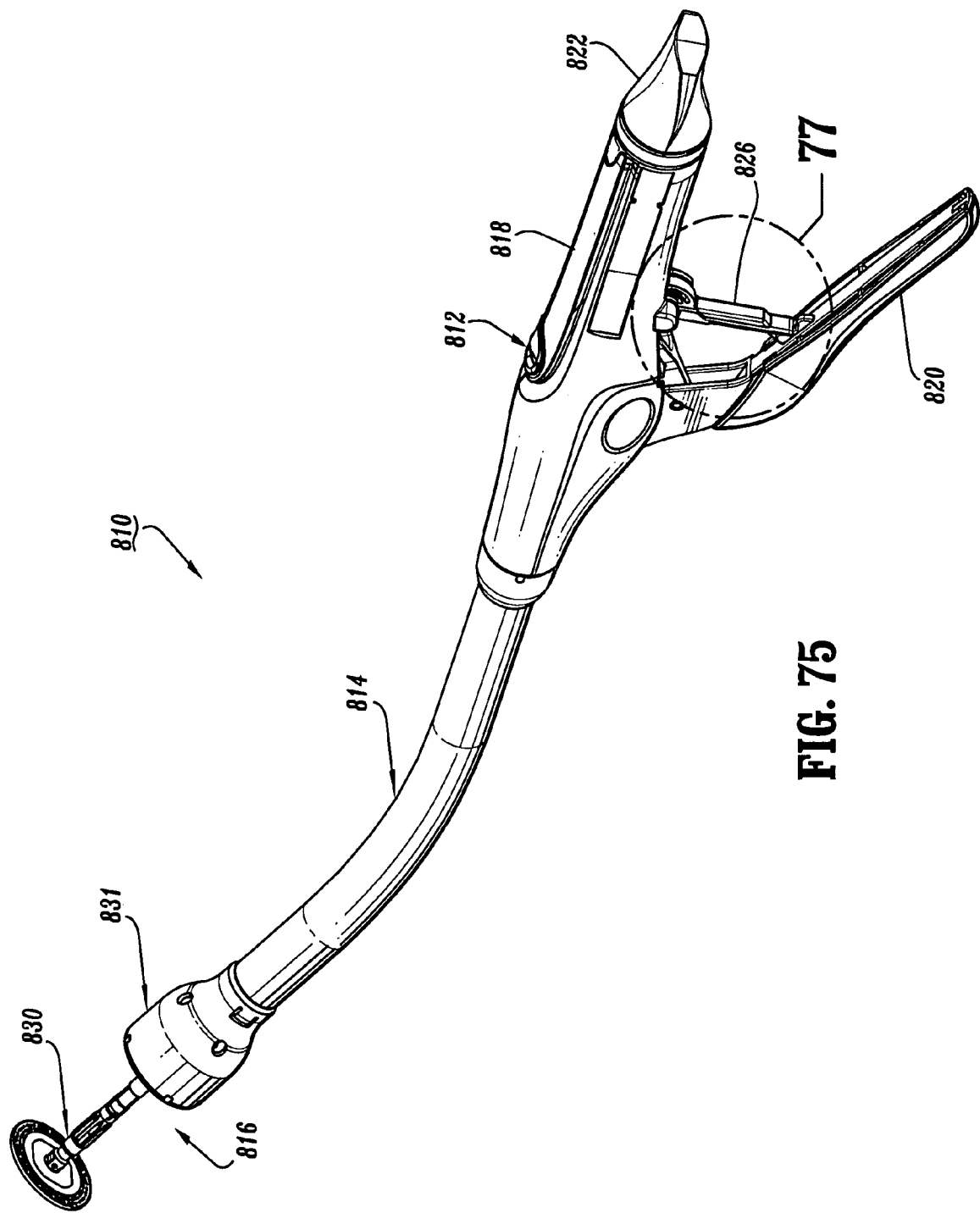
FIG. 75 is a side perspective view from the proximal end of another embodiment of the surgical stapling device with the anvil head in its unapproximated position.

As discussed above, the surgical stapler is particularly suited for use in minimally invasive gastric bypass procedures. In one method of performing a minimally invasive gastric bypass procedure, anvil assembly 610 (FIG. 64) of stapling device 600 is provided in its tilted reduced profile position. The distal end of anvil center rod 618 is secured to a hollow flexible tube (not shown). An adaptor 800 as illustrated in FIG. 75 is used to secure anvil center rod 618 to the flexible tube. Adaptor 800 includes a first end 802 having a flexible arm 804 formed thereon. Flexible arm 804 includes a distal protrusion 806 having a tapered face 806a which is dimensioned to be received, or snap-fit, into opening 646 (FIG. 63) of anvil center rod 618. A release button 808 is provided on flexible arm 804 to be pressed to disengage protrusion 806 from opening 646 of anvil center rod 618. A second end 809 of adaptor 800 includes cylindrical member 810 having a series of tapered ridges 812. Second end 809 is dimensioned to be received within the flexible tube (not shown) to secure adaptor 800 to the flexible tube. Second end 809 may be formed as a separate part from first end 802 and secured thereto using, for example, a suture (not shown) tied through opening 816. Alternately, first and second ends 802 and 808 can be integrally or monolithically formed.

To perform the gastric bypass procedure, ridged second end 809 of adaptor 800 is inserted into one end of the flexible tube. Adaptor 800 is secured to anvil center rod 618 (FIG. 1) by inserting first end 802 of adaptor 800 into bore 644 (FIG. 64) of center rod 618 such that protrusion 806 is snap-fit into opening 646. Next, the distal free end of the flexible tube is inserted into the mouth and snaked down the esophagus to the surgical site, e.g., stomach. A small incision is made at the surgical site to allow the leading end of the tube to be pulled through the incision to position anvil assembly 614 at the surgical site. As the tube is pulled through the incision, the anvil center rod 618 is pulled through the incision. Adaptor 800 is disengaged from center rod 618 by pressing on release button 808 to disengage protrusion 806 from opening 646 in center rod 618 and pulling on the tube to remove both the tube and adaptor 800. Anvil center rod 618 is then mounted on stapling device 600. Stapling device 600 can now be operated in its normal manner to perform the desired surgical procedure.

FIGS. 75-94 disclose another embodiment of the presently disclosed surgical stapling device shown generally as 810 including a passive lockout mechanism. Surgical stapling device 810 is substantially identical to stapling device 10 with the exception that proximal handle assembly 12 has been modified to include a passive lockout mechanism which operates in association with trigger lock 826 to prevent unclamping of a clamped or approximated stapling device after the trigger lock has been pivoted to its unlocked position but prior to firing of the stapling device. Only the passive lockout mechanism and those elements of surgical stapling device 810 which operate in association with the passive lockout mechanism will be described in detail below.

Figure 76:
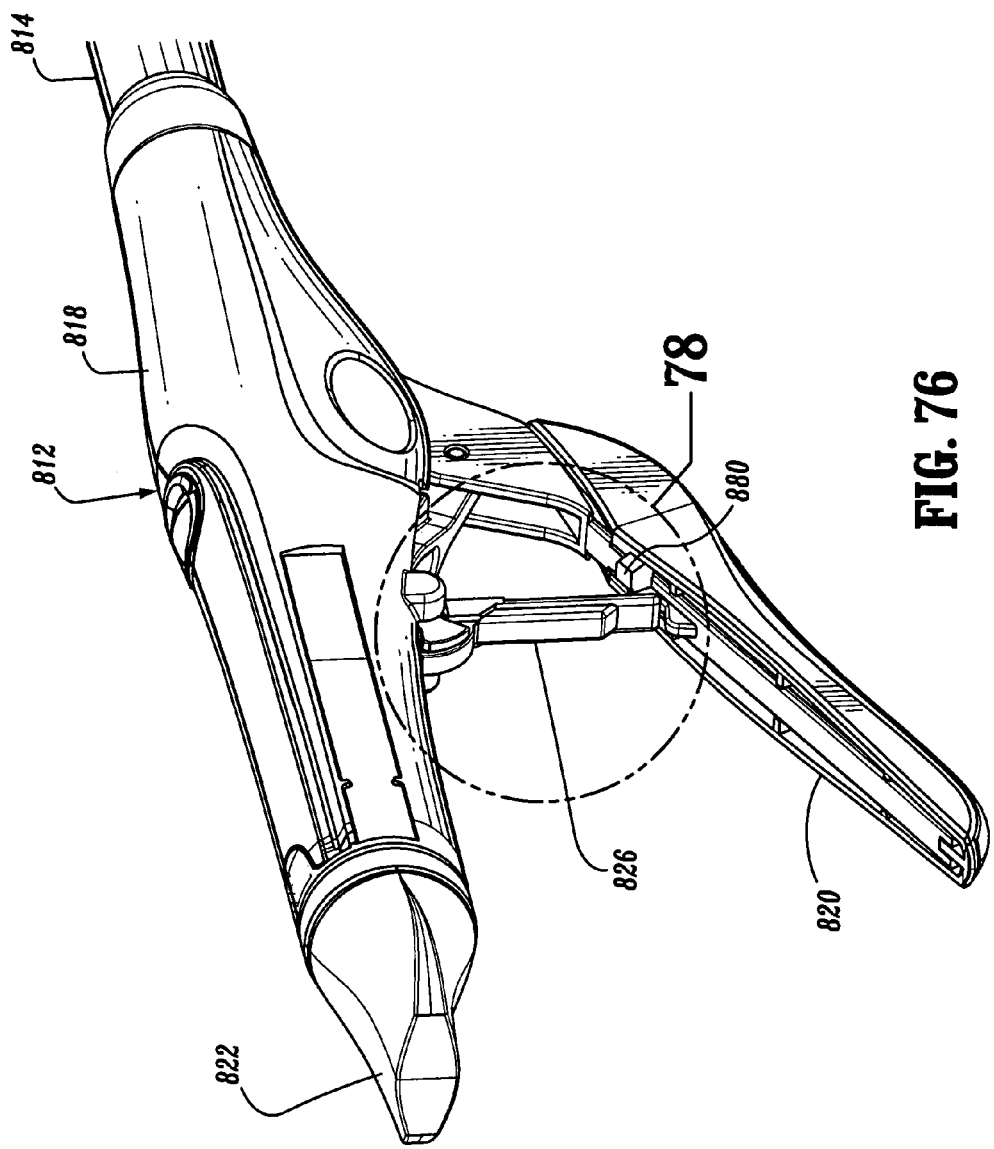
FIG. 76 is a side perspective view from the proximal end of the handle assembly of the stapling device shown in FIG. 75.
Figure 78:
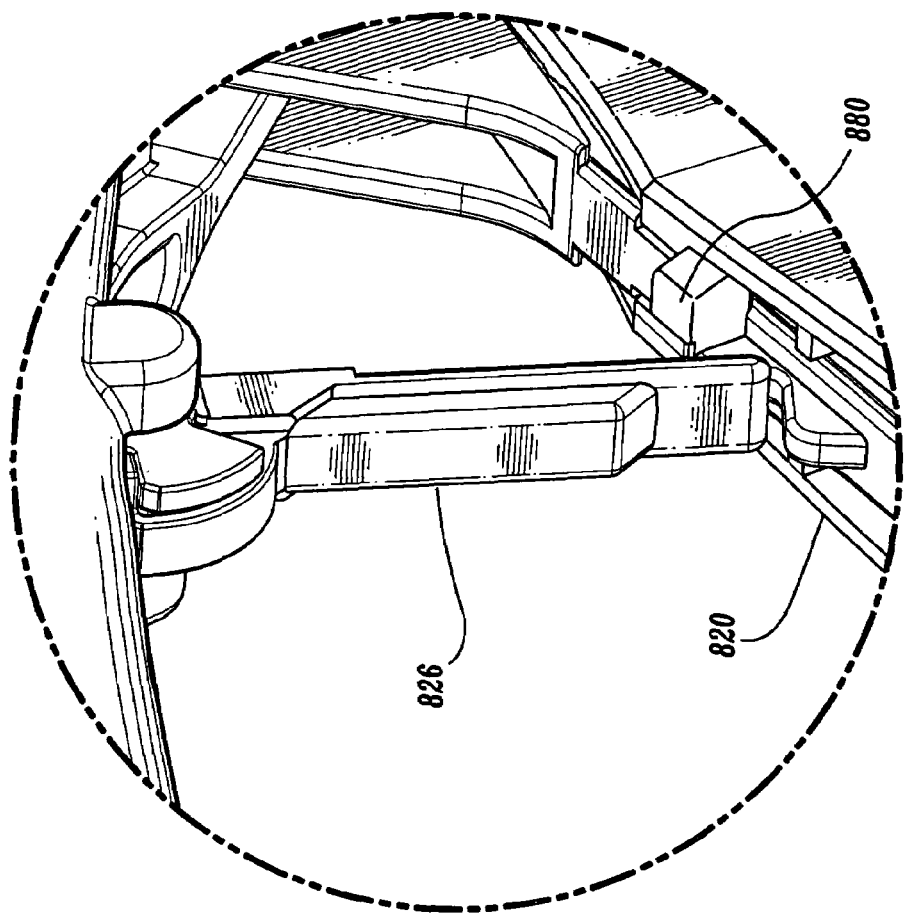
FIG. 78 is an enlarged view of the indicated area of detail shown in FIG. 76.
Figure 77:
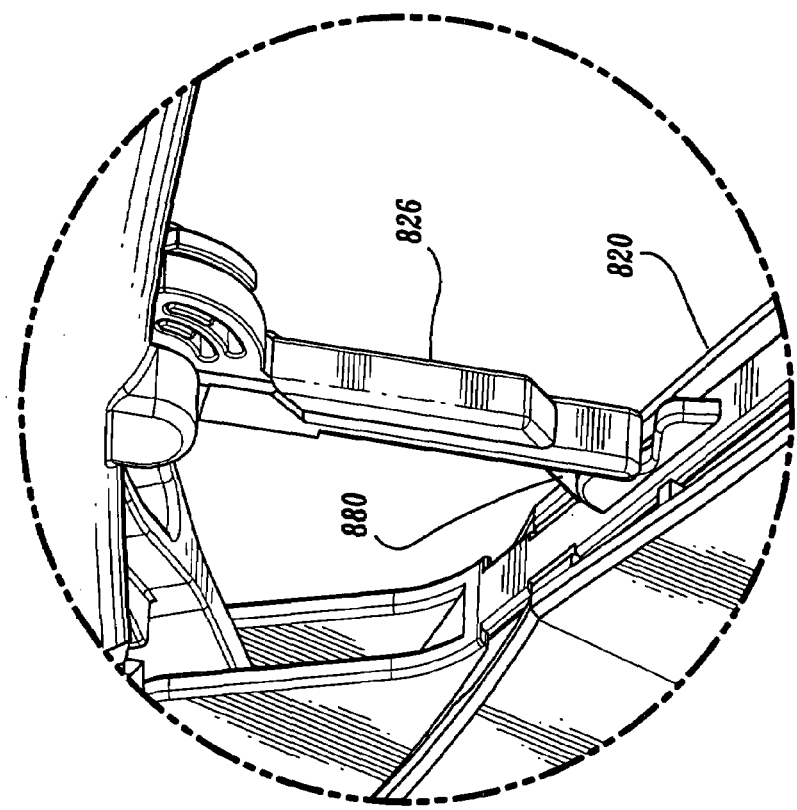
FIG. 77 is an enlarged view of the indicated area of detail shown in FIG. 75.

Referring to FIGS. 75 and 76, surgical stapling device 810 includes a proximal handle assembly 812, an elongated curved central body portion 814 and a distal head portion 816. Alternately, elongated central body portion may include a straight shaft more suitable for other surgical procedures, e.g., hemorrhoidectomies, mucosectomies, etc. Handle assembly 812 includes a stationary handle 818, a firing trigger 820, a rotatable approximation knob 822 and a pivotally mounted trigger lock 826. Distal head portion 816 includes an anvil assembly 830 and a shell assembly 831. As discussed above, anvil assembly 830 is movably supported in relation to shell assembly 831 between spaced and clamped or approximated positions.

Referring to 77-79, the passive lockout mechanism includes a locking plate 834 and a biasing member 836. Locking plate 834 includes a body 838 defining a cylindrical bore 840, a release tab 842 and a locking tab 843 having a pair of lateral extensions 844. In one embodiment, each of lateral extensions 844 is arc-shaped. Cylindrical bore 840 is dimensioned to be positioned about one of two pivot members 846 formed on trigger lock 826 such that locking plate 834 is rotatable independently of trigger lock 826 about the pivot member 846. Trigger lock 826 includes a pair of slots 848 dimensioned to slidably receive lateral extensions 844. In one embodiment, slots 848 are arc-shaped and have a radius of curvature substantially equal to the radius of curvature of lateral extensions 844. Trigger lock 826 also includes an abutment member 853 which will be discussed in further detail below.

Referring also to FIGS. 81 and 82, in one embodiment, a recess 849 is positioned between lateral extensions 844 and a pair of spaced upper and lower protrusions 850a and 850b are positioned between slots 848 of trigger lock 826. Each protrusion 850a and 850b is dimensioned to be releasably received in recess 849, each protrusion functioning to index the movement of interlock plate 834 with that of the trigger lock 826 and to retain locking plate 834 at one of two positions in relation to trigger lock 826.

Figure 79:
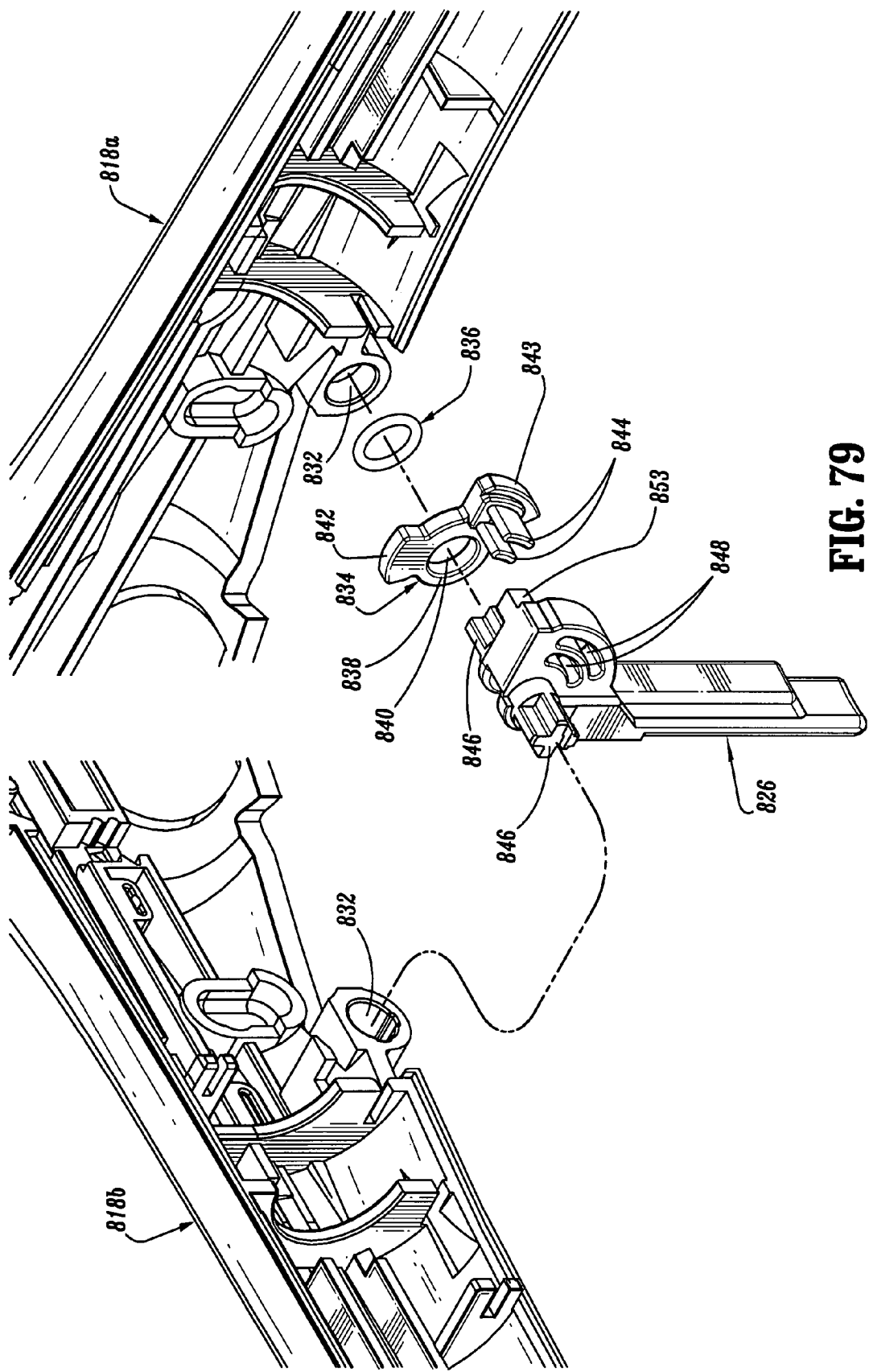
FIG. 79 is an exploded side perspective view of the handle half-sections, trigger lock and passive lockout mechanism of the stapling device shown in FIG. 75.

Referring specifically to FIG. 79, pivot members 846 of trigger lock 826 are dimensioned to be received within bores 832 of handle sections 818a and 818b. As discussed above with respect to trigger lock 26, pivot members 846 can be T-shaped and dimensioned to frictionally engage an inner wall defining bore 832 to prevent free rotation of trigger lock 826 between handle sections 818a and 818b. Alternately, use of other pivot member configurations as described above is envisioned.

In use, locking plate 834 is rotatably supported about one of pivot members 846 of trigger lock 826 by positioning pivot member 846 through cylindrical bore 840 of locking plate 834 and positioning extensions 844 through respective slots 848 formed in trigger lock 826. In the assembled condition, locking plate 834 is positioned between trigger lock 826 and handle half-section 818a. Slots 848 have a length which is greater than the length of extensions 844 such that extensions 844 are able to slide along slots 848 and locking plate 834 can rotate in relation to trigger lock 826. Biasing member 836 is positioned about pivot member 846 between locking plate 834 and handle half-section 818a to urge locking plate 834 into engagement with trigger lock 826, i.e., one of protrusions 850 is urged into recess 849.

Referring to FIG. 80, screw stop 860 is substantially identical to screw stop 306 as disclosed above with the exception that screw stop 860 includes a tab or third engagement member 862. Third engagement member 862 is positioned to engage locking tab 843 of locking plate 834 after trigger lock 826 has been unlocked if an attempt is made to unclamp device 810 prior to firing of device 810 as will be described in detail below.

Operation of the passive lockout mechanism will now be described in detail with reference to FIGS. 83-94.

Figures 83, 84:
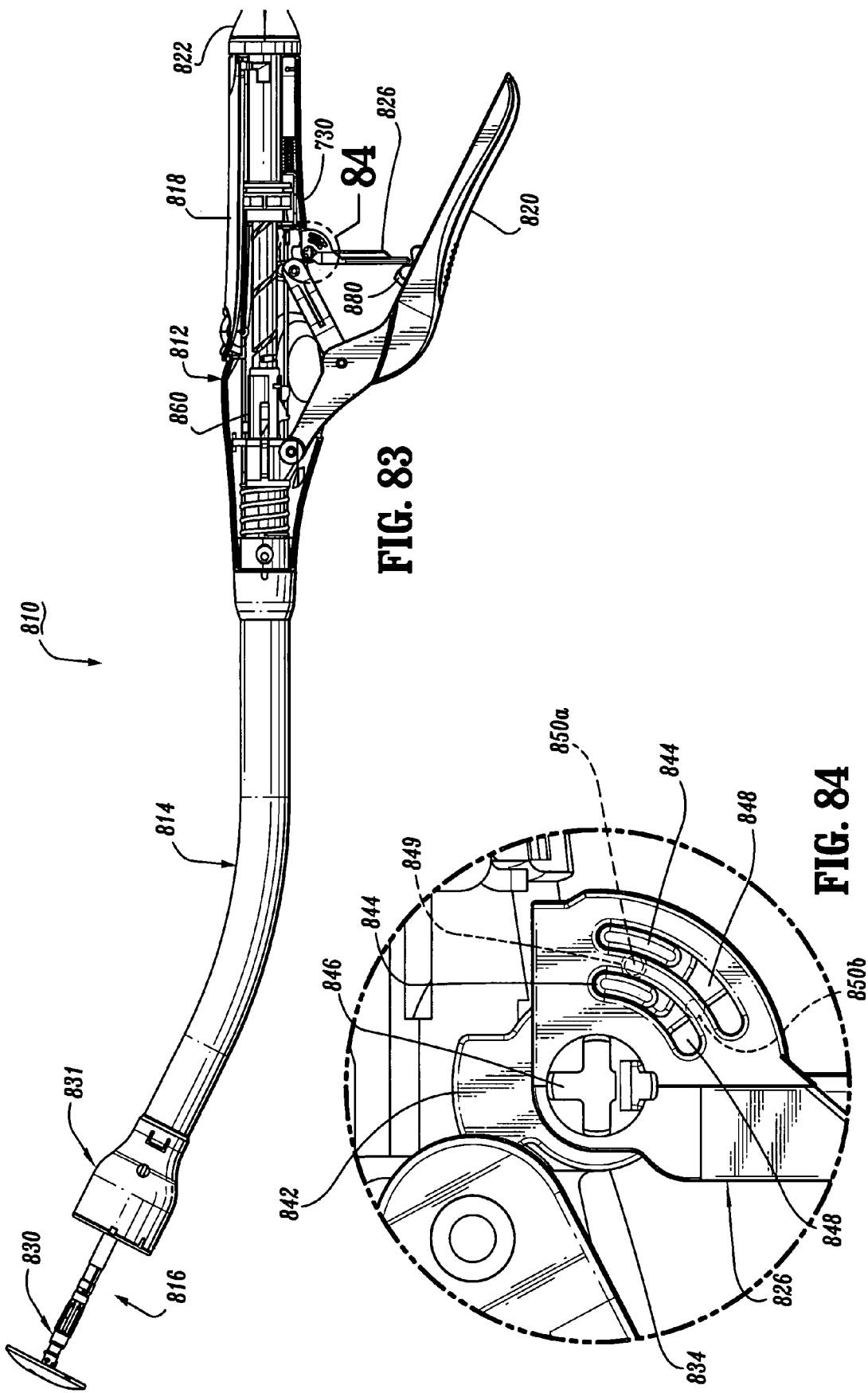
FIG. 83 is a side view of the surgical stapling device shown in FIG. 75 with a handle half-section removed and the anvil head in its approximated position.
FIG. 84 is an enlarged view of the indicated area of detail shown in FIG. 83.
Figure 85:
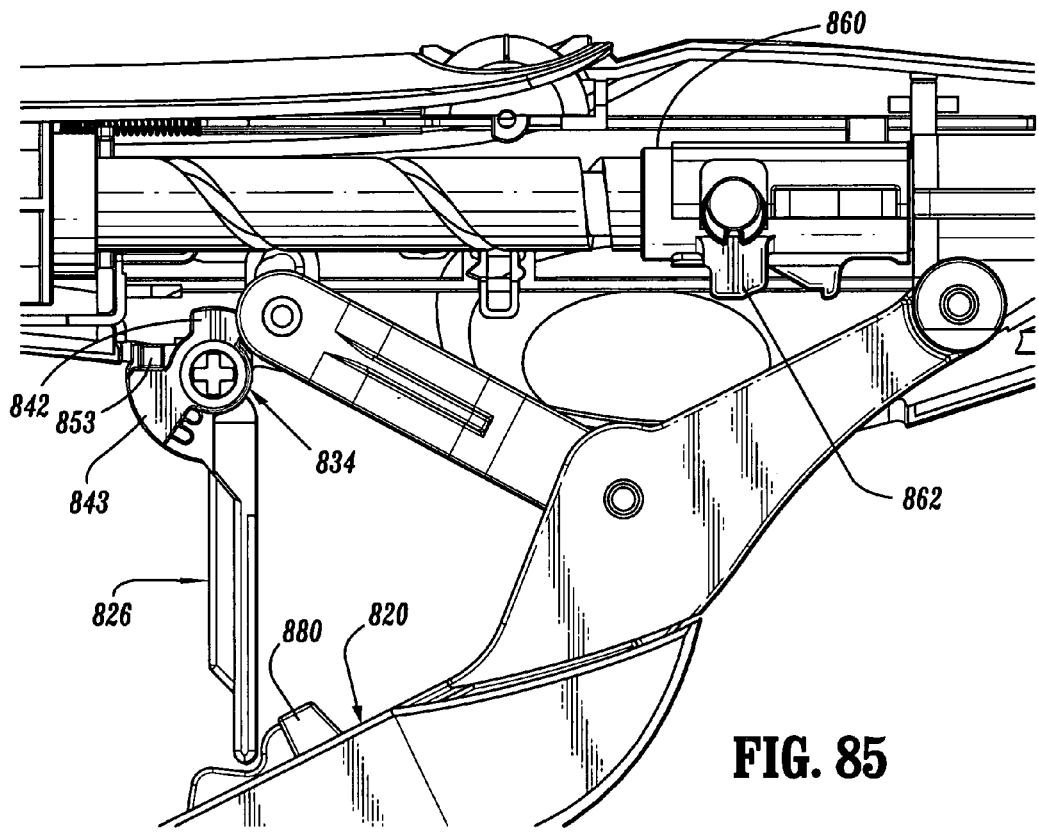
FIG. 85 is a side view of the handle assembly of the surgical stapling device shown in FIG. 83 with a handle half-section removed.
Figure 86:
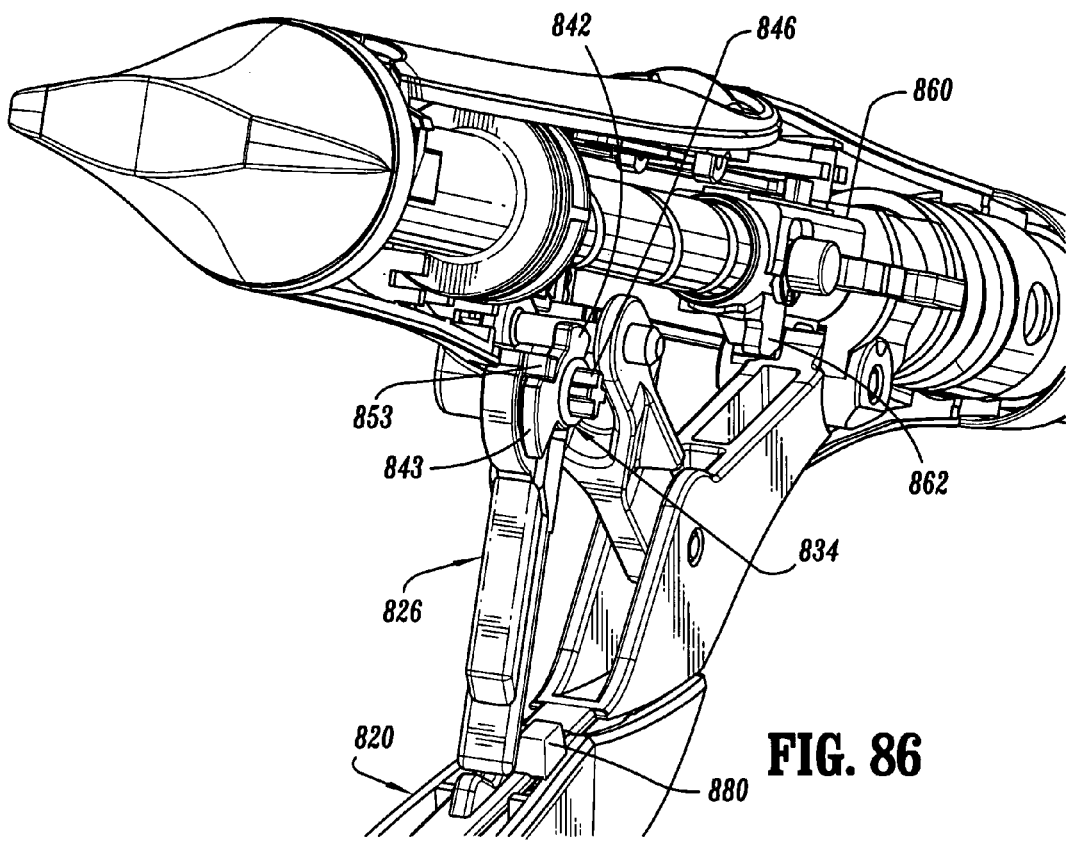
FIG. 86 is a side perspective view from the proximal end of the handle assembly shown in FIG. 85.

Referring to FIGS. 83-86, when stapling device 810 is in its unapproximated, unfired condition, anvil assembly 830 is spaced from shell assembly 831 and screw stop 860 is positioned in a distal end of handle assembly 812 (FIG. 83). As illustrated in FIG. 84, lateral extensions 844 of locking plate 834 are positioned adjacent an upper end of slots 848. As shown in phantom, upper protrusion 850a is positioned within recess 849 to releasably secure locking plate 834 to trigger lock 826.

Referring to FIGS. 87-90, when surgical stapling device 810 is approximated by rotating approximation knob 822 to move anvil assembly 830 into juxtaposed alignment with shell assembly 831, screw stop 860 is moved toward the proximal end of handle assembly 812 (FIG. 87). When this occurs, lockout member 530 is moved to a position to unlock trigger lock 826 as discussed above with respect to surgical stapling device 10. As such, trigger lock 826 can be pivoted in a direction indicated by arrow "V" in FIG. 87 from a position preventing operation of firing trigger 820 (FIG. 83) to an unlocked position substantially aligned with stationary handle 818.

Figure 89:
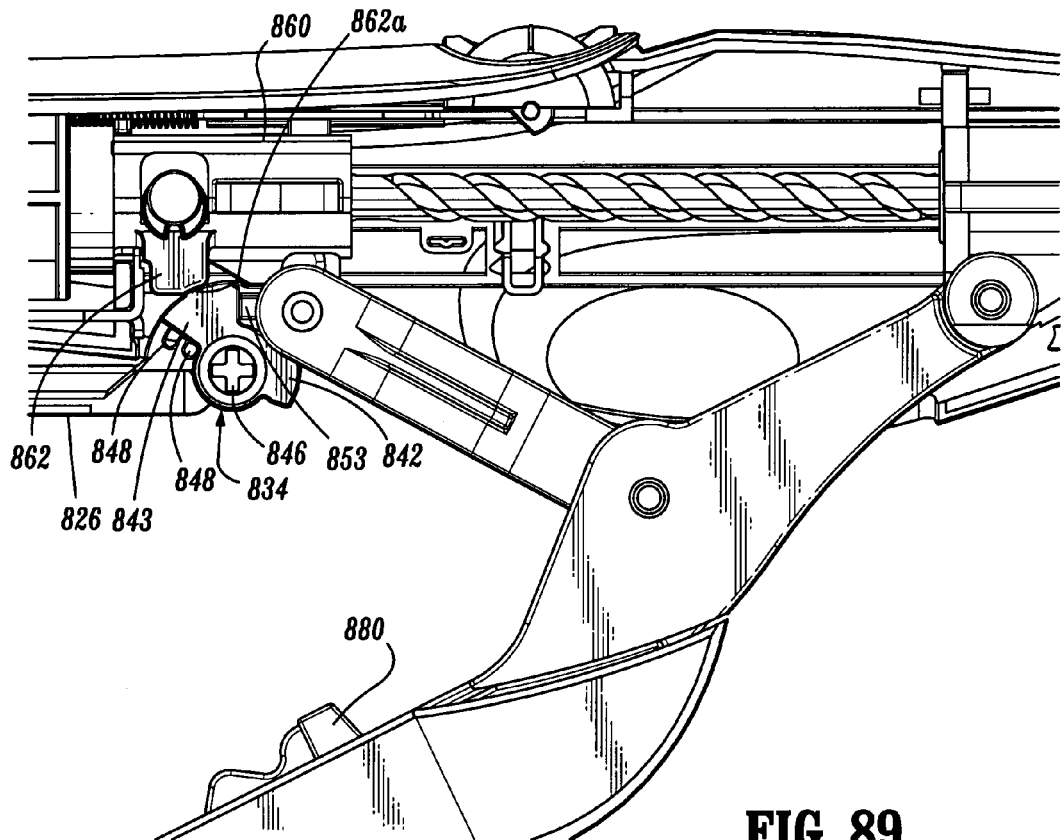
FIG. 89 is a side view of the handle assembly of the surgical stapling device shown in FIG. 87 with a handle half-section removed and the trigger lock in its unlocked position.
Figure 90:
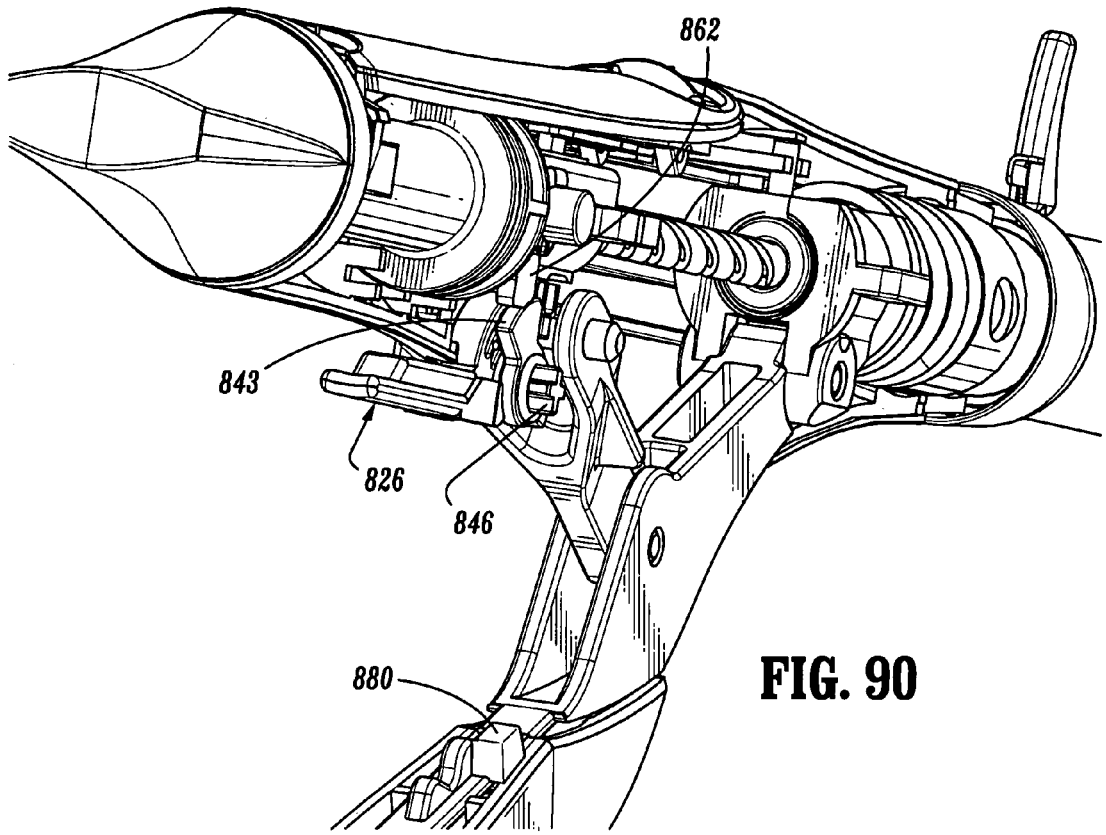
FIG. 90 is a side perspective view from the proximal end of the handle assembly shown in FIG. 89.

As trigger lock 826 is pivoted to the unlocked position, locking plate 834 is pivoted with trigger lock 826 in the direction indicated by arrow "W" in FIG. 88. This occurs because locking plate 834 is frictionally held against trigger lock 826 by biasing member 836 and by engagement of trigger lock protrusion 850a in recess 849 of locking plate 834. In this position, locking tab 843 of interlock plate 834 is positioned to abut engagement member 862 to obstruct advancement of screw stop 860 (FIG. 89). As illustrated, engagement member 822 may include a concavity 862a for receiving a curved upper surface of second tab 843. Abutment member 853 of trigger lock 826 is also positioned to engage locking tab 843 to prevent further clockwise pivoting of locking plate 834. In this position of trigger lock 826 and locking plate 834, surgical stapling device 810 is prevented from being unclamped or unapproximated. More specifically, if rotation knob 822 is rotated to unapproximate anvil assembly 830 from shell assembly 831, screw stop 860, in the manner discussed above with respect to screw stop 306, will be moved distally within handle assembly 812. As screw stop begins to move distally, however, third engagement member 862 formed on screw stop 860 abuts locking tab 843 of locking plate 834 to prevent distal movement of screw stop 860 within handle assembly 812 (See FIGS. 89 and 90). As seen in FIG. 89, abutment member 853 on trigger lock 826 acts as a stop to prevent engagement member 862 of screw stop 860 from pushing second tab 843 of locking plate 834 out of the path of screw stop 860. As such, locking plate 834 prevents an operator of a surgical stapling device 810 from unapproximating or unclamping tissue from between anvil assembly 830 and shell assembly 831 after the surgical stapling device 810 has been approximated and the trigger lock 826 has been moved to an unlocked position.

Figures 91, 92:
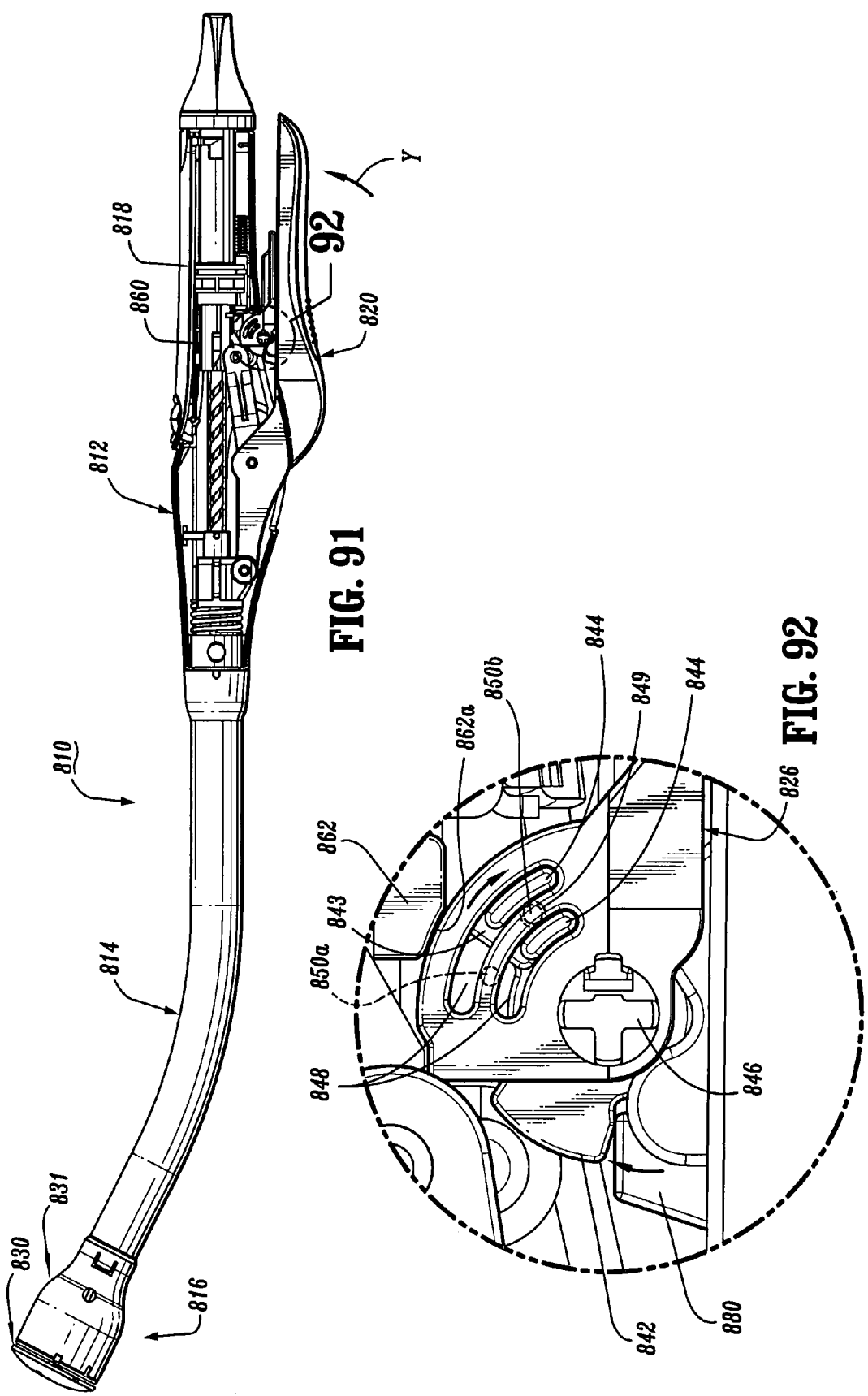
FIG. 91 is a side view of the surgical stapling device shown in FIG. 87 with a handle half-section removed and the firing trigger actuated.
FIG. 92 is an enlarged view of the indicated area of detail shown in FIG. 91.
Figure 93:
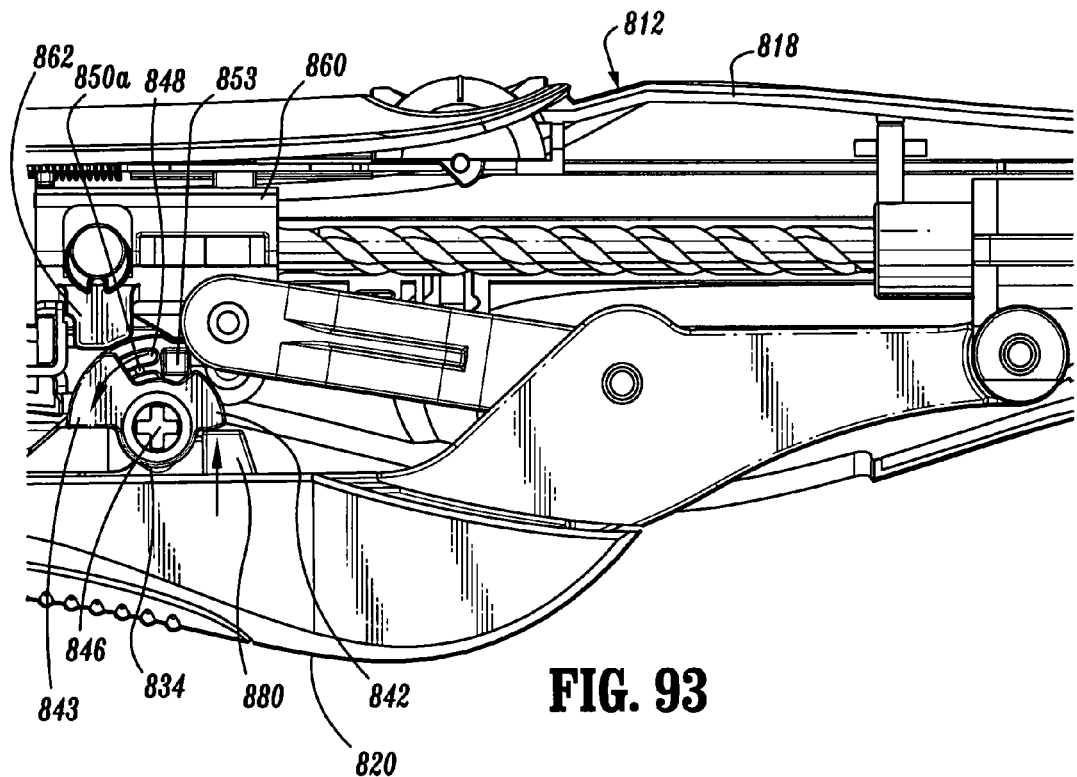
FIG. 93 is a side view of the handle assembly of the surgical stapling device shown in FIG. 91 with a handle half-section removed and the firing trigger actuated.
Figure 94:
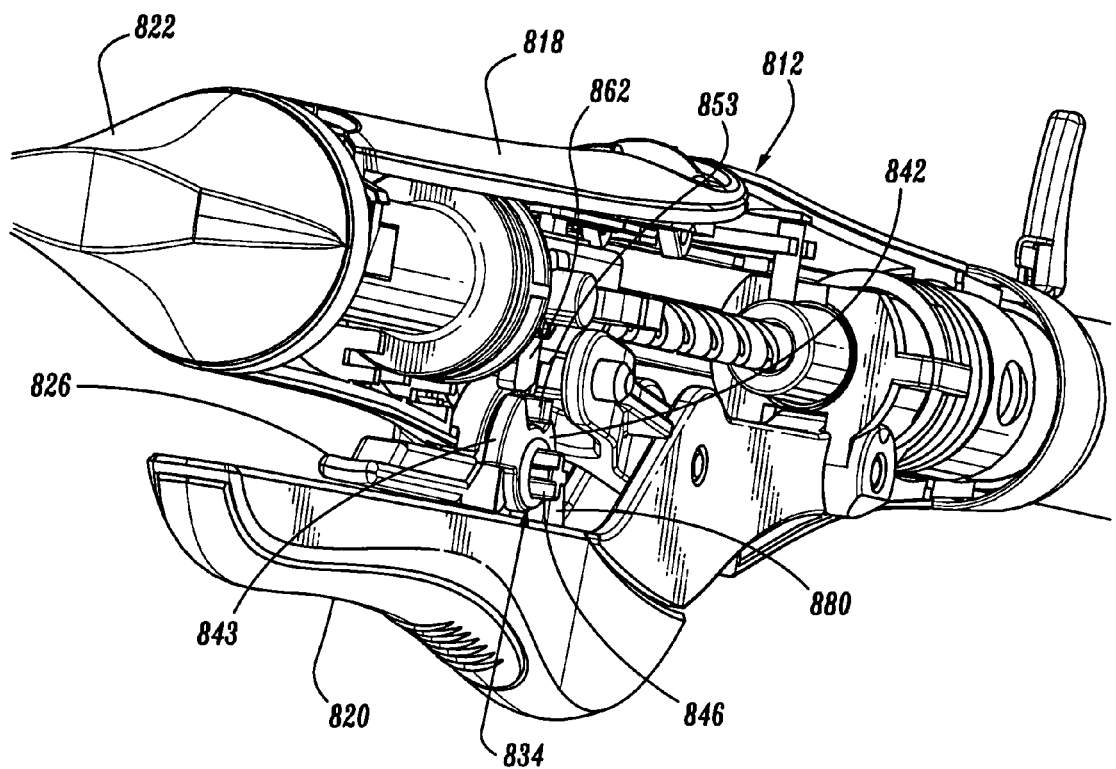
FIG. 94 is a side perspective view from the proximal end of the handle assembly shown in FIG. 93.

Referring to FIGS. 91-94, when firing trigger 820 is actuated to fire surgical stapling device 810, firing trigger 820 is moved in the direction indicated by arrow "Y" in FIG. 91 towards stationary handle 818. As firing trigger 820 moves towards stationary handle 818, a release member 880 supported on firing trigger 820 engages release tab 842 of locking plate 834 to pivot locking plate 834 in the direction indicated by arrow "X" in FIG. 92. Since firing trigger 820 engages trigger lock 826 as it is moved towards stationary handle 818 and prevents trigger lock 826 from pivoting, locking plate 834 pivots independently of trigger lock 826. As such, protrusion 850a is disengaged from recess 849 and protrusion 850b moves into recess 849. Simultaneously, lateral extensions 844 of locking plate 834 move to an opposite end of respective slots 848 of trigger lock 826. As locking plate 834 pivots, locking tab 843 of locking plate 834 is moved to a position which no longer obstructs advancement of screw stop 860 within handle assembly 812. As a result, after stapling device 810 has been fired, rotatable knob 822 can be actuated to unapproximate anvil assembly 830 in relation to shell assembly 831.

FIGS. 95 and 96 illustrate the handle assembly 912 of another embodiment of the presently disclosed surgical stapling device 900. Handle assembly 912 is substantially the same as handle assembly 812 disclosed above with the exception that firing trigger 920 has been lengthened and widened. As illustrated in FIG. 95, the proximal end 920a of firing trigger 920 is positioned proximally of the distal end of approximation knob 922. As illustrated in FIG. 96, the width of firing trigger 920 adjacent its gripping surface is about seventy-five percent of the width of stationary handle 918. By increasing the length of firing trigger 920, the moment arm is increased and the firing forces required to fire surgical stapling device 900 are substantially reduced. Further, by increasing the width of firing trigger 920, the force applied by a surgeons hand on firing trigger 920 are evenly distributed over a larger surface area of the surgeons hand. As a result, a surgeon is able to more comfortably fire the stapling device.

It will be understood that various modifications may be made to the embodiments disclosed herein. For example, although the description refers exclusively to staples, it is envisioned that staples may include different types of tissue fasteners including two-part fasteners. In a stapling device for applying two-part fastener, the anvil assembly of the stapling device would support one part of each two-part fastener while the shell assembly would support the other part of each two part fastener. Further, although the improvements disclosed herein are disclosed in association with a particular surgical stapling device, these improvements may be incorporated into any known surgical stapling device including those devices disclosed in the following U.S. patents: U.S. Pat. Nos. 5,915,616, 5,836,503, 5,588,579, 5,350,104, 5,333,773 and 5,312,024. Therefore, the above description should not be construed as limiting, but merely as exemplifications of embodiments. Those skilled in the art will envision other modifications within the scope and spirit of the claims appended hereto.

What is claimed is:

1. A surgical stapling device comprising:
a handle assembly including an approximation knob and a firing trigger;
an elongated body portion extending distally from the handle assembly;
a head portion including an anvil assembly and a shell assembly, the shell assembly housing a plurality of staples and the anvil assembly including an anvil head and an anvil center rod, the anvil head being pivotally secured to the anvil center rod about a pivot axis and being movable between an operative position and a tilted position;
an anvil retainer assembly extending from the elongated body portion through the shell assembly, the anvil retainer assembly being configured to releasably engage the anvil assembly and including a locking member which is movable from a first position in which the anvil head is moved to or retained in the operative position to a second position in which the anvil head is able to pivot from the operative position to the tilted position.

2. A surgical stapling device according to claim 1, wherein the anvil head is urged towards the tilted position by a biasing member.

3. A surgical stapling device according to claim 2, wherein the biasing member is a coil spring.

4. A surgical stapling device according to claim 1, wherein the anvil retainer assembly includes a body portion defining a longitudinal bore having an open distal end and a trocar, the trocar extending from the open distal end of the body portion and forming the locking member, the trocar being movable along the longitudinal bore between an advanced position and a retracted position, the advanced position defining the first position of the locking member and the retracted position defining the second position of the locking member.

5. A surgical stapling device according to claim 4, wherein the trocar includes a trocar tip.

6. A surgical stapling device according to claim 5, wherein the trocar tip is substantially blunt.

7. A surgical stapling device according to claim 1, wherein the body portion of the anvil retainer includes a portion having a substantially cola-bottle configuration.

8. A surgical stapling device according to claim 1, wherein the approximation knob is operably connected to a drive screw and the drive screw is operably connected to the anvil retainer assembly, wherein the approximation knob is rotatable from about two to about two and a half turns to move the anvil assembly from its approximated position to a position spaced from the shell assembly a distance sufficient to allow the anvil head to move to its tilted position.

9. A surgical stapling device comprising:
a handle assembly including an approximation knob and a firing trigger;
an elongated body portion extending distally from the handle assembly;
a head portion including an anvil assembly and a shell assembly, the shell assembly housing a plurality of staples and the anvil assembly including an anvil head and an anvil center rod, the anvil head being pivotally secured to the anvil center rod about a pivot axis and being movable between an operative position and a tilted position;
an anvil retainer assembly extending from the elongated body portion and configured to releasably engage the anvil assembly, the anvil retainer assembly including a locking member which is movable from a first position in which the anvil head is moved to or retained in the operative position to a second position in which the anvil head is able to pivot from the operative position to the tilted position;
wherein the anvil assembly includes first and second slide members movably supported by the anvil center rod, the first slide member being pivotally connected to the anvil head on one side of the pivot axis by a first drive link and the second slide member being connected to the anvil head on the other side of the pivot axis by a second drive link, the first slide member being movable in relation to the second slide member to effect movement of the anvil head between the operative position and the tilted position.

10. A surgical stapling device according to claim 9, further including a biasing member for urging the first and second slide members in relation to each other to position the anvil head in the tilted position.

11. A surgical stapling device comprising:
a handle assembly;
an approximation assembly;
an elongated body portion extending distally from the handle assembly;
an anvil retainer assembly extending from the elongated body portion;
a shell assembly housing a plurality of staples, the shell assembly supported on a distal end of the elongated body portion, the anvil retainer assembly extending through the shell assembly;
an anvil assembly releasably mounted to the anvil retainer assembly, the anvil assembly including an anvil head, the anvil head being pivotal between an operative position aligned with the shell assembly and a tilted reduced profile position;
at least a portion of the anvil retainer assembly being movable from a first position in which the anvil head is moved to or retained in the operative position to a second position in which the anvil head is able to pivot from the operative position to the tilted position, wherein the anvil head is movable to the operative position upon attachment of the anvil assembly to the anvil retainer assembly prior to approximation of the anvil and shell assemblies.

12. A surgical stapling device according to claim 11, wherein the anvil retainer assembly comprises a trocar slidably mounted within a body portion.

13. A surgical stapling device according to claim 11, further comprising a link connected to a post of the anvil assembly, the sliding member pivoting the link when engaged by the anvil retainer assembly.

14. A surgical stapling device comprising:
a handle assembly;
an approximation assembly;
an elongated body portion extending distally from the handle assembly;
an anvil retainer assembly extending from the elongated body portion;
a shell assembly housing a plurality of staples;

an anvil assembly releasably mounted to the anvil retainer assembly, the anvil assembly including an anvil head, the anvil head being pivotal between an operative position aligned with the staples for forming the staples and a tilted reduced profile position;

at least a portion of the anvil retainer assembly being movable from a first position in which the anvil head is moved to the operative position to a second position which the anvil head is able to pivot from the operative position to the tilted position, wherein the anvil is movable to the operative position prior to approximation of the anvil and shell assemblies; and wherein the anvil retainer assembly comprises a trocar slidably mounted within a body portion and the trocar is biased to a distal position to move the anvil head to the operative position.

15. A surgical stapling device according to claim 14, wherein the anvil assembly includes a slide member engageable by the anvil retainer assembly to move the anvil head to the operative position.

16. A surgical stapling device comprising:

a handle assembly including an approximation knob;

an elongated body portion extending distally from the handle assembly;

an anvil assembly;

an anvil retainer assembly movable with respect to the elongated body portion;

a shell assembly supported on a distal end of the elongated body portion and housing a plurality of staples, the anvil retainer assembly extending through the shell assembly;

an anvil assembly releasably mounted to the anvil retainer assembly, the anvil assembly including an anvil head, wherein the anvil retainer assembly is configured to move the anvil head from a tilted reduced profile position to an operative position aligned with the shell assembly upon mounting the anvil assembly to the anvil retainer assembly.

17. A surgical stapling device according to claim 16, wherein the anvil retainer assembly includes a trocar which is moveable from an extended position to move or retain the anvil head in the operative position to a retracted position and a cam member which is movable from a first position retaining the trocar in the extended position to a release position; wherein upon firing of the staples, the cam member moves to moves to the release position to enable the anvil head to move to the tiled position upon unapproximation of the anvil assembly.

18. A surgical stapling device according to claim 17, further comprising an approximation member operatively connected to the anvil retainer assembly, wherein the approximation knob moves the anvil retainer assembly.

19. A surgical stapling device according to claim 16, wherein the anvil retainer assembly comprises a trocar slidably mounted within a body portion.

* * * * *

UNITED STATES PATENT AND TRADEMARK OFFICE
CERTIFICATE OF CORRECTION

PATENT NO.         : 7,431,191 B2  
APPLICATION NO. : 11/788671  
DATED              : October 7, 2008  
INVENTOR(S)      : Keith L. Milliman Page 1 of 1

It is certified that error appears in the above-identified patent and that said Letters Patent is hereby corrected as shown below:

TITLE PAGE:  
Item (63) Continuation of application No. 10/968,722, filed on "Jan. 27, 2005" should read --October 18, 2004--.

Signed and Sealed this

Twenty-second Day of December, 2009

David J. Kappos  
*Director of the United States Patent and Trademark Office*